(12) United States Patent
Ellinger et al.

(10) Patent No.: US 12,344,654 B2
(45) Date of Patent: Jul. 1, 2025

(54) MAGE A4 T CELL RECEPTORS

(71) Applicants: MEDIGENE IMMUNOTHERAPIES GMBH, Planegg-Martinsried (DE); Regeneron Pharmaceuticals, Inc., Tarrytown, NY (US)

(72) Inventors: Christian Ellinger, Munich (DE); Daniel Sommermeyer, Munich (DE); Geoffrey Parsons, Jamaica Plain, MA (US); Jasdeep Mann, Lake Forest Park, WA (US)

(73) Assignees: MEDIGENE IMMUNOTHERAPIES GMBH, Planegg-Martinsried (DE); Regeneron Pharmaceuticals, Inc., Tarrytown, NY (US)

( * ) Notice: Subject to any disclaimer, the term of this patent is extended or adjusted under 35 U.S.C. 154(b) by 917 days.

(21) Appl. No.: 17/441,861

(22) PCT Filed: Mar. 27, 2020

(86) PCT No.: PCT/EP2020/058779
§ 371 (c)(1),
(2) Date: Sep. 22, 2021

(87) PCT Pub. No.: WO2020/193767
PCT Pub. Date: Oct. 1, 2020

(65) Prior Publication Data
US 2023/0159612 A1 May 25, 2023

(30) Foreign Application Priority Data
Mar. 27, 2019 (EP) ..................... 19165387

(51) Int. Cl.
| | |
|---|---|
| C12N 5/02 | (2006.01) |
| A61K 35/17 | (2015.01) |
| A61P 35/00 | (2006.01) |
| C07K 14/725 | (2006.01) |
| C12N 5/0783 | (2010.01) |
| A61K 38/00 | (2006.01) |

(52) U.S. Cl.
CPC .......... *C07K 14/7051* (2013.01); *A61K 35/17* (2013.01); *A61P 35/00* (2018.01); *C12N 5/0636* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | |
|---|---|---|
| 7,157,091 B1 | 1/2007 | Van Snick et al. |
| 7,311,914 B2 | 12/2007 | Zhang et al. |
| 11,654,158 B2 | 5/2023 | Boyerinas |
| 2015/0246959 A1 | 9/2015 | Robbins et al. |
| 2015/0307585 A1 | 10/2015 | Blankenstein et al. |
| 2017/0267737 A1 | 9/2017 | Protzer et al. |
| 2017/0360913 A1 | 12/2017 | Zhao et al. |
| 2018/0244797 A1 | 8/2018 | Puléet al. |
| 2023/0044580 A1 | 2/2023 | Mann et al. |
| 2023/0159612 A1 | 5/2023 | Ellinger et al. |

FOREIGN PATENT DOCUMENTS

| | | |
|---|---|---|
| WO | WO 03/020763 | 3/2003 |
| WO | WO 2017/158103 | 9/2017 |
| WO | WO 2017/174824 | 10/2017 |
| WO | WO 2017/175006 | 10/2017 |
| WO | WO 2018/067618 | 4/2018 |
| WO | WO 2019/036688 | 2/2019 |
| WO | WO-2020/193767 A1 | 10/2020 |
| WO | WO-2020/227483 A1 | 11/2020 |

OTHER PUBLICATIONS

Dotto et al., "Squamous cell cancers: a unified perspective on biology and genetics." Cancer Cell 29(5) (2016): 622-637.
Wang et al., "Detection of RNA Interference (RNAi) Mediated mRNA Cleavage in Fresh Injected Tumor Tissue from Patients in a Phase I Trial of pbi-shRNA (TM) Lipoplex Targeting Stathmin-1", Molecular Therapy. vol. 22. Nature Publishing Group, (2014).
Yang et al., "T-cell lineage determination." Immunol Rev. Nov. 2010;238(1): 12-22.
Yang et al., "Development of optimal bicistronic lentiviral vectors facilitates high-level TCR gene expression and robust tumor cell recognition." Gene Ther. Nov. 2008;15(21): 1411-23.
International Preliminary Report on Patentability for International Application No. PCT/EP20/58779 dated Sep. 28, 2021.
International Preliminary Report on Patentability for International Application No. PCT/US2020/031796 dated Nov. 2, 2021.
Asao et al., "Cutting Edge: The Common γ-Chain Is an Indispensable Subunit of the IL-21 Receptor Complex," The Journal of Immunology, 2001, 167, 1-5.
Bhan et al., "MAGEA4 induces growth in normal oral keratinocytes by inhibiting growth arrest and apoptosis," Oncol Rep. Oct. 2012;28(4):1498-502.
Bird, Robert E., et al. "Single-chain antigen-binding proteins." Science (1988); 242.4877: 423-427.
Brichard et al., "Cancer regression and neurological toxicity cases after anti-MAGE-A3 TCR gene therapy," J Immunother. Feb. 2013;36(2):79-81.

(Continued)

*Primary Examiner* — Maher M Haddad
(74) *Attorney, Agent, or Firm* — Foley Hoag LLP; Amy E. Mandragouras; Ariana D. Harris

(57) ABSTRACT

The present invention relates to an isolated T cell receptor (TCR) specific for MAGE-A4 and a polypeptide comprising a functional portion of the TCR. Further implicated are a multivalent TCR complex, a nucleic acid encoding a TCR, a cell expressing the TCR and a pharmaceutical composition comprising the TCR. The invention also refers to the TCR for use as a medicament, in particular to the TCR for use in the treatment of cancer.

26 Claims, 17 Drawing Sheets

Specification includes a Sequence Listing.

(56) References Cited

OTHER PUBLICATIONS

Cameron et al., "Identification of a Titin-derived HLA-A1-presented peptide as a cross-reactive target for engineered MAGE A3-directed T cells," Sci Transl Med. Aug. 7, 2013;5(197):197ra103.

Challita, P. et al., "Multiple modifications in cis elements of the long terminal repeat of retroviral vectors lead to increased expression and decreased DNA methylation in embryonic carcinoma cells." J Virol. (1995); 69(2): 748-755.

Chaudhary, Vijay K., et al. "A rapid method of cloning functional variable-region antibody genes in *Escherichia coli* as single-chain immunotoxins." Proceedings of the National Academy of Sciences (1990); 87.3: 1066-1070 (and correction).

Cooper, Laurence JN, et al. "T-cell clones can be rendered specific for CD19: Toward the selective augmentation of the graft-versus-B-lineage leukemia effect." Blood (2003); 101.4: 1637-1644.

Cribbs et al., "Simplified production and concentration of lentiviral vectors to achieve high transduction in primary human T cells," BMC Biotechnol. Nov. 12, 2013;13:98.

Cullen, B.R., "Human Immunodeficiency Virus as a Prototypic Complex Retrovirus", Journal of Virology (1991); 65(3): 1053-1056.

Cullen et al., "Regulatory Pathways Governing HIV-1 Replication", Cell (1989); 58: 423-426.

Daudi et al., "Expression and immune responses to MAGE antigens predict survival in epithelial ovarian cancer," PLoS One. Aug. 7, 2014;9(8):e104099.

De Felipe et al., "Targeting of proteins derived from self-processing polyproteins containing multiple signal sequences." Traffic (2004); 5.8: 616-626.

Donnelly, M. et al., "The 'cleavage' activities of foot-and-mouth disease virus 2A site-directed mutants and naturally occurring '2A-like' sequences." J Gen Virol. (2001); 82 (Pt 5): 1027-1041.

Duffour et al., "A MAGE-A4 peptide presented by HLA-A2 is recognized by cytolytic T lymphocytes," Eur. J. Immunol. Oct. 1999; 29(10):3329-37.

Dull et al., "A third-generation lentivirus vector with a conditional packaging system", Journal of Virology (1998); 72(11): 8463-8471.

Engels et al., "Relapse or eradication of cancer is predicted by peptide-major histocompatibility complex affinity," Cancer Cell. Apr. 15, 2013;23(4):516-26.

Flynn et al., "Stem memory T cells (TSCM)-their role in cancer and HIV immunotherapies," Clin Transl Immunology. Jul. 18, 2014;3(7):e20.

Fukuo, "Interleukin 2, IL-2," The Journal of Japan Atherosclerosis Society, 1996, 24, 4-5, 155-161.

Gattinoni et al., "A human memory T cell subset with stem cell-like properties," Nat Med. Sep. 18, 2011;17(10):1290-1297.

Giudicelli et al., "IMGT/LIGM-DB, the IMGT comprehensive database of immunoglobulin and T cell receptor nucleotide sequences," Nucleic Acids Res. Jan. 1, 2006;34(Database issue):D781-4.

Gure et al., "Cancer-testis genes are coordinately expressed and are markers of poor outcome in non-small cell lung cancer," Clin Cancer Res. Nov. 15, 2005;11(22):8055-62.

International Search Report and Written Opinion mailed on Jul. 7, 2020, for International Application No. PCT/EP2020/058779, 12 pages.

Haga-Friedman et al., "Incorporation of transmembrane hydrophobic mutations in the TCR enhance its surface expression and T cell functional avidity," J Immunol. Jun. 1, 2012;188(11):5538-46.

Jena et al., "Driving CAR-Based T-Cell Therapy to Success," Curr Hematol Malig Rep. Mar. 2014; 9(1): 50-56.

Kageyama et al., "Adoptive Transfer of MAGE-A4 T-cell Receptor Gene-Transduced Lymphocytes in Patients with Recurrent Esophageal Cancer," Clin Cancer Res. May 15, 2015;21(10):2268-77.

Kim et al., "Pattern of cancer/testis antigen expression in lung cancer patients," Int J Mol Med. Apr. 2012;29(4):656-62.

Kutner, et al., "Simplified production andconcentration of HIV-1-based lentiviral vectors usingHYPERFlask vessels and anion exchange membrane chromatography", BMC Biotechnol. (2009); 9:10. p. 1-7.

Kutner et al., "Production, concentration and titration of pseudotyped HIV-1-based lentiviral vectors", Nature Protocols (2009); 4: 495-505.

Li et al., "Expression Profile of Cancer-Testis Genes in 121 Human Colorectal Cancer Tissue and Adjacent Normal Tissue," Clin Cancer Res (2005) 11 (5): 1809-1814.

Linette et al., "Cardiovascular toxicity and titin cross-reactivity of affinity-enhanced T cells in myeloma and melanoma," Blood. Aug. 8, 2013;122(6):863-71.

Liu, X. et al. (2016). "A chimeric switch-receptor targeting PD1 augments the efficacy of second-generation CAR T cells in advanced solid tumors," Cancer Res. 76:1578-1590.

Lugli et al., "Identification, isolation and in vitro expansion of human and nonhuman primate T stem cell memory cells," Nat Protoc. Jan. 2013;8(1):33-42.

Morgan et al., "Cancer regression and neurological toxicity following anti-MAGE-A3 TCR gene therapy," J Immunother. Feb. 2013;36(2):133-51.

Naldini L. et al., "Efficient transfer, integration, and sustained long-term expression of the transgene in adult rat brains injected with a lentiviral vector", Proc Natl Acad Sci USA (1996); 93(21): 11382-11388.

Naldini, L. et al., "In vivo gene delivery and stable transduction of nondividing cells by a lentiviral vector", Science (1996); 272(5259): 263-267.

Naldini, L., "Lentiviruses as gene transfer agents for delivery to non-dividing cells", Curr Opin Biotechnol. (1998); 5: 457-463.

Otte et al., "MAGE-A gene expression pattern in primary breast cancer," Cancer Res. Sep. 15, 2001;61(18):6682-6687.

Ozaki et al., "Cytokine and Cytokine Receptor Pleiotropy and Redundancy," The Journal of Biological Chemistry, Aug. 16, 2002, 277,33, 29355-29358.

Patel, S. et al., "Impact of chimeric immune receptor extracellular protein domains on T cell function." Gene Ther (1999); 6(3): 412-419.

Riddell et al., "Adoptive therapy with chimeric antigen receptor-modified T cells of defined subset composition," Cancer J. Mar.-Apr. 2014;20(2):141-4.

Ryan, M. et al., "Virus-encoded proteinases of the picornavirus super-group." J Gen Virol. (1997); 78 (Pt 4): 699-723.

Schmitt et al., T cell receptor gene therapy for cancer. Hum Gene Ther. Nov. 2009;20(11):1240-1248.

Shi et al., "Chimeric antigen receptor for adoptive immunotherapy of cancer: latest research and future prospects," Molecular Cancer 2014, 13:219, 8 pages.

Sommermeyer et al., "Minimal Amino Acid Exchange in Human TCR Constant Regions Fosters Improved Function of TCR Gene-Modified T Cells," The Journal of Immunology Jun. 1, 2010, 184 (11) 6223-6231.

Szymczak, Andrea L., et al. "Correction of multi-gene deficiency in vivo using a single'self-cleaving'2A peptide-based retroviral vector." Nature Biotechnology (2004); 22.5: 589-594.

Tajima et al., "Expression of cancer/testis (CT) antigens in lung cancer," Lung Cancer. Oct. 2003;42(1):23-33.

Takara Bio Inc., Idenshidonyujikken handobukku (handbook of gene transfer experimentation), Nov. 2015, p. 1-10.

Xue et al., "Exploiting T cell receptor genes for cancer immunotherapy," Clin Exp Immunol. Feb. 2005;139(2):167-72.

Yamada et al., "Preferential expression of cancer/testis genes in cancer stem-like cells: proposal of a novel sub-category, cancer/testis/stem gene," Tissue Antigens. Jun. 2013;81(6):428-34.

Yang, S. et al., "Development of optimal bicistronic lentiviral vectors facilitates high-level TCR gene expression and robust tumor cell recognition", Gene Therapy, Nov. 2008, vol. 15, No. 21, pp. 1411-1423.

Zennou et al., "HIV-1 genome nuclear import is mediated by a central DNA flap," Cell. Apr. 14, 2000;101(2):173-85.

Zhang, C. et al. (2017). "Engineering CAR-T cells," Biomaker Res. 5:22, 6 total pages.

Zufferey et al., "Multiply attenuated lentiviral vector achieves efficient gene delivery in vivo", Nat Biotechnol. (1997), 15(9):871-875.

(56) References Cited

OTHER PUBLICATIONS

Zufferey, R. et al., "Woodchuck hepatitis virus posttranscriptional regulatory element enhances expression of transgenes delivered by retroviral vectors." J Virol. (1999); 73(4): 2886-2892.
International Search Report and Written Opinion mailed on Oct. 14, 2020, for International Application No. PCT/US2020/031796, 16 pages.
Supplementary European Search Report for EP Application No. 20802730.0 dated Jul. 11, 2023, 6 pages.
Third Party Submission Under 37 CFR 1.290 submitted on Sep. 1, 2020, for U.S. Appl. No. 16/348,450, 9 pages.

A)

B)

SEQUENCE LISTING

```
<160> NUMBER OF SEQ ID NOS: 116

<210> SEQ ID NO 1
<211> LENGTH: 10
<212> TYPE: PRT
<213> ORGANISM: Homo sapiens

<400> SEQUENCE: 1

Gly Val Tyr Asp Gly Arg Glu His Thr Val
1               5                   10

<210> SEQ ID NO 2
<211> LENGTH: 7
<212> TYPE: PRT
<213> ORGANISM: Homo sapiens

<400> SEQUENCE: 2
```

Thr Ser Asp Gln Ser Tyr Gly
1               5

<210> SEQ ID NO 3
<211> LENGTH: 8
<212> TYPE: PRT
<213> ORGANISM: Homo sapiens

<400> SEQUENCE: 3

Gln Gly Ser Tyr Asp Glu Gln Asn
1               5

<210> SEQ ID NO 4
<211> LENGTH: 14
<212> TYPE: PRT
<213> ORGANISM: Homo sapiens

<400> SEQUENCE: 4

Cys Ala Met Ser Gly Asp Ser Ala Gly Asn Met Leu Thr Phe
1               5                   10

<210> SEQ ID NO 5
<211> LENGTH: 5
<212> TYPE: PRT
<213> ORGANISM: Homo sapiens

<400> SEQUENCE: 5

Lys Gly His Asp Arg
1               5

<210> SEQ ID NO 6
<211> LENGTH: 6
<212> TYPE: PRT
<213> ORGANISM: Homo sapiens

<400> SEQUENCE: 6

Ser Phe Asp Val Lys Asp
1               5

<210> SEQ ID NO 7
<211> LENGTH: 17
<212> TYPE: PRT
<213> ORGANISM: Homo sapiens

<400> SEQUENCE: 7

Cys Ala Thr Ser Asp Trp Asp Arg Ser Gly Asp Lys Glu Thr Gln Tyr
1               5                   10                  15

Phe

<210> SEQ ID NO 8
<211> LENGTH: 136
<212> TYPE: PRT
<213> ORGANISM: Homo sapiens

<400> SEQUENCE: 8

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
                20                  25                  30

Val Gln Glu Lys Glu Ala Val Thr Leu Asp Cys Thr Tyr Asp Thr Ser
            35                  40                  45

Asp Gln Ser Tyr Gly Leu Phe Trp Tyr Lys Gln Pro Ser Ser Gly Glu
        50                  55                  60

Met Ile Phe Leu Ile Tyr Gln Gly Ser Tyr Asp Gln Asn Ala Thr
65                  70                  75                  80

Glu Gly Arg Tyr Ser Leu Asn Phe Gln Lys Ala Arg Lys Ser Ala Asn
            85                  90                  95

Leu Val Ile Ser Ala Ser Gln Leu Gly Asp Ser Ala Met Tyr Phe Cys
        100                 105                 110

Ala Met Ser Gly Asp Ser Ala Gly Asn Met Leu Thr Phe Gly Gly Gly
    115                 120                 125

Thr Arg Leu Met Val Lys Pro His
130                 135

<210> SEQ ID NO 9
<211> LENGTH: 135
<212> TYPE: PRT
<213> ORGANISM: Homo sapiens

<400> SEQUENCE: 9

Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
    50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
            85                  90                  95

Leu Glu Ser Ala Ile Pro Asn Gln Thr Ala Leu Tyr Phe Cys Ala Thr
        100                 105                 110

Ser Asp Trp Asp Arg Ser Gly Asp Lys Glu Thr Gln Tyr Phe Gly Pro
    115                 120                 125

Gly Thr Arg Leu Leu Val Leu
130                 135

<210> SEQ ID NO 10
<211> LENGTH: 276
<212> TYPE: PRT
<213> ORGANISM: Artificial Sequence
<220> FEATURE:
<223> OTHER INFORMATION: with mininmal murinized constant region

<400> SEQUENCE: 10

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
            85                  90                  95

```
Leu Val Ile Ser Ala Ser Gln Leu Gly Asp Ser Ala Met Tyr Phe Cys
                100                 105                 110

Ala Met Ser Gly Asp Ser Ala Gly Asn Met Leu Thr Phe Gly Gly Gly
            115                 120                 125

Thr Arg Leu Met Val Lys Pro His Ile Gln Asn Pro Asp Pro Ala Val
        130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
210                 215                 220

Ser Ser Asp Val Pro Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
            275

<210> SEQ ID NO 11
<211> LENGTH: 312
<212> TYPE: PRT
<213> ORGANISM: Artificial Sequence
<220> FEATURE:
<223> OTHER INFORMATION: with minimal murinized constant region

<400> SEQUENCE: 11

Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
    50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
            100                 105                 110

Ser Asp Trp Asp Arg Ser Gly Asp Lys Glu Thr Gln Tyr Phe Gly Pro
        115                 120                 125

Gly Thr Arg Leu Leu Val Leu Glu Asp Leu Asn Lys Val Phe Pro Pro
    130                 135                 140

Glu Val Ala Val Phe Glu Pro Ser Lys Ala Glu Ile Ala His Thr Gln
145                 150                 155                 160

Lys Ala Thr Leu Val Cys Leu Ala Thr Gly Phe Phe Pro Asp His Val
                165                 170                 175
```

```
Glu Leu Ser Trp Trp Val Asn Gly Lys Val His Ser Gly Val Ser
            180                 185                 190

Thr Asp Pro Gln Pro Leu Lys Glu Gln Pro Ala Leu Asn Asp Ser Arg
            195                 200                 205

Tyr Cys Leu Ser Ser Arg Leu Arg Val Ser Ala Thr Phe Trp Gln Asn
210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Ile Thr Ser Ala Ser
            260                 265                 270

Tyr His Gln Gly Val Leu Ser Ala Thr Ile Leu Tyr Glu Ile Leu Leu
            275                 280                 285

Gly Lys Ala Thr Leu Tyr Ala Val Leu Val Ser Ala Leu Val Leu Met
            290                 295                 300

Ala Met Val Lys Arg Lys Asp Phe
305                 310

<210> SEQ ID NO 12
<211> LENGTH: 7
<212> TYPE: PRT
<213> ORGANISM: Homo sapiens

<400> SEQUENCE: 12

Thr Ser Asp Pro Ser Tyr Gly
1               5

<210> SEQ ID NO 13
<211> LENGTH: 8
<212> TYPE: PRT
<213> ORGANISM: Homo sapiens

<400> SEQUENCE: 13

Gln Gly Ser Tyr Asp Gln Gln Asn
1               5

<210> SEQ ID NO 14
<211> LENGTH: 15
<212> TYPE: PRT
<213> ORGANISM: Homo sapiens

<400> SEQUENCE: 14

Cys Ala Met Ser Gly Gly Tyr Thr Gly Gly Phe Lys Thr Ile Phe
1               5                   10                  15

<210> SEQ ID NO 15
<211> LENGTH: 5
<212> TYPE: PRT
<213> ORGANISM: Homo sapiens

<400> SEQUENCE: 15

Ser Gly Asp Leu Ser
1               5

<210> SEQ ID NO 16
<211> LENGTH: 6
<212> TYPE: PRT
<213> ORGANISM: Homo sapiens

<400> SEQUENCE: 16
```

Tyr Tyr Asn Gly Glu Glu
1               5

<210> SEQ ID NO 17
<211> LENGTH: 13
<212> TYPE: PRT
<213> ORGANISM: Homo sapiens

<400> SEQUENCE: 17

Cys Ala Ser Ser Gly Gly Asp Gly Asp Glu Gln Phe Phe
1               5                   10

<210> SEQ ID NO 18
<211> LENGTH: 137
<212> TYPE: PRT
<213> ORGANISM: Homo sapiens

<400> SEQUENCE: 18

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
                20                  25                  30

Val Gln Glu Lys Glu Ala Val Thr Leu Asp Cys Thr Tyr Asp Thr Ser
            35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Ser Gly Gly Tyr Thr Gly Gly Phe Lys Thr Ile Phe Gly Ala
        115                 120                 125

Gly Thr Arg Leu Phe Val Lys Ala Asn
    130                 135

<210> SEQ ID NO 19
<211> LENGTH: 131
<212> TYPE: PRT
<213> ORGANISM: Homo sapiens

<400> SEQUENCE: 19

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
                20                  25                  30

Ala Thr Gly Gln Arg Val Thr Leu Arg Cys Ser Pro Arg Ser Gly Asp
            35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Gly Gly Asp Gly Asp Glu Gln Phe Phe Gly Pro Gly Thr Arg Leu

```
                       115                 120                 125

Thr Val Leu
        130

<210> SEQ ID NO 20
<211> LENGTH: 277
<212> TYPE: PRT
<213> ORGANISM: Artificial Sequence
<220> FEATURE:
<223> OTHER INFORMATION: with minimal murinized constant region

<400> SEQUENCE: 20

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Ser Gly Gly Tyr Thr Gly Gly Phe Lys Thr Ile Phe Gly Ala
        115                 120                 125

Gly Thr Arg Leu Phe Val Lys Ala Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Ser Asp Val Pro Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 21
<211> LENGTH: 310
<212> TYPE: PRT
<213> ORGANISM: Artificial Sequence
<220> FEATURE:
<223> OTHER INFORMATION: with minimal murinized constant region

<400> SEQUENCE: 21
```

```
Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Gly Gly Asp Gly Asp Glu Gln Phe Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Lys Ala Glu Ile Ala His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Ile Thr Ser Arg Ser Tyr His Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 22
<211> LENGTH: 6
<212> TYPE: PRT
<213> ORGANISM: Homo sapiens

<400> SEQUENCE: 22

Asp Ser Ala Ser Asn Tyr
1               5

<210> SEQ ID NO 23
<211> LENGTH: 7
<212> TYPE: PRT
<213> ORGANISM: Homo sapiens

<400> SEQUENCE: 23
```

```
Ile Arg Ser Asn Val Gly Glu
1               5
```

<210> SEQ ID NO 24
<211> LENGTH: 14
<212> TYPE: PRT
<213> ORGANISM: Homo sapiens

<400> SEQUENCE: 24

```
Cys Ala Ala Ser Arg Gly Thr Gly Phe Gln Lys Leu Val Phe
1               5                   10
```

<210> SEQ ID NO 25
<211> LENGTH: 5
<212> TYPE: PRT
<213> ORGANISM: Homo sapiens

<400> SEQUENCE: 25

```
Leu Gly His Asp Thr
1               5
```

<210> SEQ ID NO 26
<211> LENGTH: 6
<212> TYPE: PRT
<213> ORGANISM: Homo sapiens

<400> SEQUENCE: 26

```
Tyr Asn Asn Lys Glu Leu
1               5
```

<210> SEQ ID NO 27
<211> LENGTH: 16
<212> TYPE: PRT
<213> ORGANISM: Homo sapiens

<400> SEQUENCE: 27

```
Cys Ala Ser Ser Gln Phe Trp Asp Gly Ala Gly Asp Glu Gln Tyr Phe
1               5                   10                  15
```

<210> SEQ ID NO 28
<211> LENGTH: 133
<212> TYPE: PRT
<213> ORGANISM: Homo sapiens

<400> SEQUENCE: 28

```
Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Arg Pro Gln
        50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Arg Gly Thr Gly Phe Gln Lys Leu Val Phe Gly Thr Gly Thr Arg Leu
        115                 120                 125
```

Leu Val Ser Pro Asn
    130

<210> SEQ ID NO 29
<211> LENGTH: 134
<212> TYPE: PRT
<213> ORGANISM: Homo sapiens

<400> SEQUENCE: 29

Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Gln Phe Trp Asp Gly Ala Gly Asp Glu Gln Tyr Phe Gly Pro Gly
        115                 120                 125

Thr Arg Leu Thr Val Thr
    130

<210> SEQ ID NO 30
<211> LENGTH: 273
<212> TYPE: PRT
<213> ORGANISM: Artificial Sequence
<220> FEATURE:
<223> OTHER INFORMATION: with minimal murinized constant region

<400> SEQUENCE: 30

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Arg Gly Thr Gly Phe Gln Lys Leu Val Phe Gly Thr Gly Thr Arg Leu
        115                 120                 125

Leu Val Ser Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile

```
                165                 170                 175
Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Ser Asp
            210                 215                 220

Val Pro Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 31
<211> LENGTH: 311
<212> TYPE: PRT
<213> ORGANISM: Artificial Sequence
<220> FEATURE:
<223> OTHER INFORMATION: with minimal murinized constant region

<400> SEQUENCE: 31

Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
                20                  25                  30

Gln Met Gly Asn Asp Lys Ser Ile Lys Cys Glu Gln Asn Leu Gly His
            35                  40                  45

Asp Thr Met Tyr Trp Tyr Lys Gln Asp Ser Lys Lys Phe Leu Lys Ile
        50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Gln Phe Trp Asp Gly Ala Gly Asp Glu Gln Tyr Phe Gly Pro Gly
        115                 120                 125

Thr Arg Leu Thr Val Thr Glu Asp Leu Asn Lys Val Phe Pro Pro Glu
130                 135                 140

Val Ala Val Phe Glu Pro Ser Lys Ala Glu Ile Ala His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255
```

```
Ala Glu Ala Trp Gly Arg Ala Asp Cys Gly Ile Thr Ser Ala Ser Tyr
            260                 265                 270

His Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Phe
305                 310

<210> SEQ ID NO 32
<211> LENGTH: 21
<212> TYPE: DNA
<213> ORGANISM: Artificial Sequence
<220> FEATURE:
<223> OTHER INFORMATION: Codon optimized

<400> SEQUENCE: 32
accagcgatc agagctacgg c                                        21

<210> SEQ ID NO 33
<211> LENGTH: 24
<212> TYPE: DNA
<213> ORGANISM: Artificial Sequence
<220> FEATURE:
<223> OTHER INFORMATION: codon optimized

<400> SEQUENCE: 33
cagggcagct acgacgagca gaat                                     24

<210> SEQ ID NO 34
<211> LENGTH: 42
<212> TYPE: DNA
<213> ORGANISM: Artificial Sequence
<220> FEATURE:
<223> OTHER INFORMATION: codon optimized

<400> SEQUENCE: 34
tgtgccatga gcggcgatag cgccggcaac atgcttacat tt                 42

<210> SEQ ID NO 35
<211> LENGTH: 15
<212> TYPE: DNA
<213> ORGANISM: Artificial Sequence
<220> FEATURE:
<223> OTHER INFORMATION: codon optimized

<400> SEQUENCE: 35
aagggccacg accgg                                               15

<210> SEQ ID NO 36
<211> LENGTH: 18
<212> TYPE: DNA
<213> ORGANISM: Artificial Sequence
<220> FEATURE:
<223> OTHER INFORMATION: codon optimized

<400> SEQUENCE: 36
agcttcgacg tgaaggac                                            18

<210> SEQ ID NO 37
<211> LENGTH: 51
<212> TYPE: DNA
<213> ORGANISM: Artificial Sequence
<220> FEATURE:
```

<223> OTHER INFORMATION: codon optimized

<400> SEQUENCE: 37

```
tgcgccacca gcgactggga tagaagcggc gacaaagaga cacagtactt c        51
```

<210> SEQ ID NO 38
<211> LENGTH: 831
<212> TYPE: DNA
<213> ORGANISM: Artificial Sequence
<220> FEATURE:
<223> OTHER INFORMATION: with minimal murinized constant region; codon
      optimized

<400> SEQUENCE: 38

```
atgagcctga gcagcctgct gaaggtcgtg acagcctctc tgtggctcgg acctggaatc     60
gcccagaaga tcacccagac acagcccggc atgttcgtgc aagagaaaga agccgtgaca    120
ctggactgca cctacgacac cagcgatcag agctacggcc tgttctggta caagcagcct    180
agcagcggcg agatgatctt cctgatctac cagggcagct acgacgagca gaatgccacc    240
gagggcagat acagcctgaa cttccagaag gcccggaagt ccgccaacct ggtcatttct    300
gcttctcagc tgggcgacag cgccatgtac ttttgtgcca tgagcggcga tagcgccggc    360
aacatgctta catttggcgg cggaacccgg ctgatggtca gccccatat tcagaacccc    420
gatcctgccg tgtaccagct gagagacagc aagagcagcg acaagagcgt gtgtctgttc    480
accgacttcg acagccagac caacgtgtcc cagagcaagg acagcgacgt gtacatcacc    540
gacaagaccg tgctggacat gcggagcatg gacttcaaga gcaacagcgc cgtggcctgg    600
tccaacaaga gcgatttcgc ctgcgccaac gccttcaaca atagcattat ccccgaggac    660
acattcttcc ccagctccga tgtgccctgc gacgtgaagc tggtggaaaa gagcttcgag    720
acagacacca acctgaactt ccagaacctg agcgtgatcg gcttcagaat cctgctgctg    780
aaggtggccg gcttcaatct gctgatgacc ctgagactgt ggtccagctg a            831
```

<210> SEQ ID NO 39
<211> LENGTH: 939
<212> TYPE: DNA
<213> ORGANISM: Artificial Sequence
<220> FEATURE:
<223> OTHER INFORMATION: with minimal murinized constant region; codon
      optimized

<400> SEQUENCE: 39

```
atggccagcc tgctgttctt ctgcggcgcc ttttatctgc tcggcaccgg ctctatggac     60
gccgacgtta cacagacccc tcggaacaga atcaccaaga ccggcaagcg gatcatgctg    120
gaatgcagcc agaccaaggg ccacgaccgg atgtactggt acagacagga ccctggcctg    180
ggcctgagac tgatctacta cagcttcgac gtgaaggaca tcaacaaggg cgagatcagc    240
gacggctaca gcgtgtcaag acaggctcag gccaagttca gcctgtctct ggaaagcgct    300
atccccaacc agacagccct gtacttctgc gccaccagcg actgggatag aagcggcgac    360
aaagagacac agtacttcgg ccctggcacc agactgctgg tgctggaaga tctgaacaag    420
gtgttccctc cagaggtggc cgtgttcgag ccttctaagg ccgagattgc cacacacag    480
aaagccacac tcgtgtgcct ggctaccggc ttctttcctg accacgtgga actgtcttgg    540
tgggtcaacg gcaaagaggt gcacagcggc gtcagcacag atcccagcc tctgaaagaa    600
cagcccgctc tgaacgacag ccggtactgt ctgagcagca actgagagt gtccgccaca    660
ttctggcaga accccagaaa ccacttcaga tgccaggtgc agttctacgg cctgagcgag    720
```

```
aacgatgagt ggacccagga tagagccaag cctgtgacac agatcgtgtc tgccgaagcc    780
tggggcagag ccgattgtgg aattaccagc gccagctacc atcagggcgt gctgtctgcc    840
acaatcctgt acgagatcct gctgggcaaa gccactctgt acgccgtgct ggtgtctgcc    900
ctggtgctga tggccatggt caagagaaag gactttga                            939
```

```
<210> SEQ ID NO 40
<211> LENGTH: 21
<212> TYPE: DNA
<213> ORGANISM: Artificial Sequence
<220> FEATURE:
<223> OTHER INFORMATION: codon optimized

<400> SEQUENCE: 40
accagcgatc ctagctacgg c                                              21
```

```
<210> SEQ ID NO 41
<211> LENGTH: 24
<212> TYPE: DNA
<213> ORGANISM: Artificial Sequence
<220> FEATURE:
<223> OTHER INFORMATION: codon optimized

<400> SEQUENCE: 41
cagggcagct acgaccagca gaat                                           24
```

```
<210> SEQ ID NO 42
<211> LENGTH: 45
<212> TYPE: DNA
<213> ORGANISM: Artificial Sequence
<220> FEATURE:
<223> OTHER INFORMATION: codon optimized

<400> SEQUENCE: 42
tgtgccatga gcggcggcta caccggcggc ttcaagacaa tcttt                    45
```

```
<210> SEQ ID NO 43
<211> LENGTH: 15
<212> TYPE: DNA
<213> ORGANISM: Artificial Sequence
<220> FEATURE:
<223> OTHER INFORMATION: codon optimized

<400> SEQUENCE: 43
agcggcgacc tgagc                                                     15
```

```
<210> SEQ ID NO 44
<211> LENGTH: 18
<212> TYPE: DNA
<213> ORGANISM: Artificial Sequence
<220> FEATURE:
<223> OTHER INFORMATION: codon optimized

<400> SEQUENCE: 44
tactacaacg gcgaggaa                                                  18
```

```
<210> SEQ ID NO 45
<211> LENGTH: 39
<212> TYPE: DNA
<213> ORGANISM: Artificial Sequence
<220> FEATURE:
<223> OTHER INFORMATION: codon optimized

<400> SEQUENCE: 45
```
tgtgccagct ctggcggaga tggcgacgag cagttttt              39

<210> SEQ ID NO 46
<211> LENGTH: 834
<212> TYPE: DNA
<213> ORGANISM: Artificial Sequence
<220> FEATURE:
<223> OTHER INFORMATION: with minimal murinized constant region; codon
      optimized

<400> SEQUENCE: 46
atgagcctga gcagcctgct gaaggtcgtg acagcctctc tgtggctcgg acctggaatc         60
gcccagaaga tcacccagac acagcccggc atgttcgtgc aagagaaaga agccgtgaca        120
ctggactgca cctacgacac cagcgatcct agctacggcc tgttctggta caagcagcct        180
agcagcggcg agatgatctt cctgatctac cagggcagct acgaccagca gaatgccacc        240
gagggcagat acagcctgaa cttccagaag gcccggaagt ccgccaacct ggtcatttct        300
gctagccagc tgggcgacag cgccatgtac ttttgtgcca tgagcggcgg ctacaccggc        360
ggcttcaaga caatctttgg cgccggaacc agactgttcg tgaaggccaa tattcagaac        420
cccgatcctg ccgtgtacca gctgagagac agcaagagca cgacaagag cgtgtgtctg         480 ttcaccgact cgacagcca gaccaacgtg tcccagagca aggacagcga cgtgtacatc        540
accgacaaga ccgtgctgga catgcggagc atggacttca agagcaacag cgccgtggcc        600
tggtccaaca gagcgatt cgcctgcgcc aacgccttca caatagcat tatccccgag        660 gacacattct ccccagctc cgatgtgccc tgcgacgtga gctggtgga aaagagcttc        720 gagacagaca ccaacctgaa cttccagaac ctgagcgtga tcggcttcag aatcctgctg        780
ctgaaggtgg ccggcttcaa tctgctgatg accctgagac tgtggtccag ctga            834

<210> SEQ ID NO 47
<211> LENGTH: 933
<212> TYPE: DNA
<213> ORGANISM: Artificial Sequence
<220> FEATURE:
<223> OTHER INFORMATION: with minimal murinized constant region; codon
      optimized

<400> SEQUENCE: 47
atgggcttca gactgctgtg ctgcgtggcc ttttgtctgc ttggagccgg acctgtggat         60
agcggcgtta cccagacacc taagcacctg atcacagcca caggccagcg cgtgaccctg        120
agatgttctc ctagaagcgg cgacctgagc gtgtactggt atcagcagtc tctggaccag        180
ggcctgcagt tcctgatcca gtactacaac ggcgaggaaa gagccaaggg caacatcctg        240
gaacggttca gcgcccagca gttcccagat ctgcacagcg agctgaacct gagcagcctg        300
gaactgggag atagcgccct gtacttctgt gccagctctg gcggagatgg cgacgagcag        360
ttttttggcc ctggcaccag actgaccgtg ctggaggacc tgaagaacgt gttccctccg        420
gaggtggccg tgttcgagcc cagcaaagcc gagatcgcgc acacccagaa ggccaccctg        480
gtgtgcctgg ccaccggctt ctaccccgac cacgtggagc tgagctggtg ggtgaacggc        540
aaggaggtgc acagcggcgt gagcaccgac ccccagcccc tgaaggagca gcccgccctg        600
aacgacagcc gctactgcct gagcagccgc ctgcgcgtga gcgccacctt ctggcagaac        660
ccccgcaacc acttccgctg ccaggtgcag ttctacggcc tgagcgagaa cgacgagtgg        720
acccaggacc gcgccaagcc cgtgacccag atcgtgagcg ccgaggcctg ggccgcgcc        780 gactgcggca ttaccagccg cagctaccat cagggcgtgc tgagcgccac catcctgtac        840

```
gagatcctgc tgggcaaggc caccctgtac gccgtgctgg tgagcgccct ggtgctgatg        900
gcgatggtga agcgcaagga cagccgcggc tga                                    933
```

<210> SEQ ID NO 48
<211> LENGTH: 18
<212> TYPE: DNA
<213> ORGANISM: Artificial Sequence
<220> FEATURE:
<223> OTHER INFORMATION: codon optimized

<400> SEQUENCE: 48

```
gacagcgcca gcaactac                                                      18
```

<210> SEQ ID NO 49
<211> LENGTH: 21
<212> TYPE: DNA
<213> ORGANISM: Artificial Sequence
<220> FEATURE:
<223> OTHER INFORMATION: codon optimized

<400> SEQUENCE: 49

```
atccggtcca acgtgggcga g                                                  21
```

<210> SEQ ID NO 50
<211> LENGTH: 42
<212> TYPE: DNA
<213> ORGANISM: Artificial Sequence
<220> FEATURE:
<223> OTHER INFORMATION: codon optimized

<400> SEQUENCE: 50

```
tgcgctgcca gcagaggcac cggcttccag aaactggtgt tt                           42
```

<210> SEQ ID NO 51
<211> LENGTH: 15
<212> TYPE: DNA
<213> ORGANISM: Artificial Sequence
<220> FEATURE:
<223> OTHER INFORMATION: codon optimized

<400> SEQUENCE: 51

```
ctgggccacg acacc                                                         15
```

<210> SEQ ID NO 52
<211> LENGTH: 18
<212> TYPE: DNA
<213> ORGANISM: Artificial Sequence
<220> FEATURE:
<223> OTHER INFORMATION: codon optimized

<400> SEQUENCE: 52

```
tacaacaaca aagagctg                                                      18
```

<210> SEQ ID NO 53
<211> LENGTH: 48
<212> TYPE: DNA
<213> ORGANISM: Artificial Sequence
<220> FEATURE:
<223> OTHER INFORMATION: codon optimized

<400> SEQUENCE: 53

```
tgtgccagca gccagttctg ggatggcgct ggcgacgagc agtatttt                     48
```

<210> SEQ ID NO 54

```
<211> LENGTH: 822
<212> TYPE: DNA
<213> ORGANISM: Artificial Sequence
<220> FEATURE:
<223> OTHER INFORMATION: with minimal murinized constant region; codon
      optimized

<400> SEQUENCE: 54
atgaccagca tccgggccgt gttcatcttc ctgtggctgc agctggacct ggtcaacggc      60
gagaatgtgg aacagcaccc cagcacactg agcgtgcaag agggcgattc tgccgtgatc     120
aagtgcacct acagcgacag cgccagcaac tacttcccct ggtacaagca agagctgggc     180
aaaagacccc agctgatcat cgacatccgg tccaacgtgg cgagaagaa ggaccagaga      240
atcgccgtga cactgaacaa gaccgccaag cacttcagcc tgcacatcac cgagacacag     300
cctgaggata cgccgtgta cttttgcgct gccagcagag gcaccggctt ccagaaactg      360
gtgtttggca ccggcaccag actgctggtg tccccaaata ttcagaaccc cgatcctgcc     420
gtgtaccagc tgagagacag caagagcagc gacaagagct gtgtctgtt caccgacttc      480
gacagccaga ccaacgtgtc ccagagcaag gacagcgacg tgtacatcac cgacaagacc     540
gtgctggaca tgcggagcat ggacttcaag agcaacagcg ccgtggcctg gtccaacaag     600
agcgatttcg cctgcgccaa cgccttcaac aatagcatta ccccgagga cacattcttc     660
cccagctccg atgtgccctg cgacgtgaag ctggtggaaa agagcttcga cagacacacc     720
aacctgaact tccagaacct gagcgtgatc ggcttcagaa tcctgctgct gaaggtggcc     780
ggcttcaatc tgctgatgac cctgagactg tggtccagct ga                        822

<210> SEQ ID NO 55
<211> LENGTH: 936
<212> TYPE: DNA
<213> ORGANISM: Artificial Sequence
<220> FEATURE:
<223> OTHER INFORMATION: with minimal murinized constant region; codon
      optimized

<400> SEQUENCE: 55
atgggctgca gactgctgtg ctgtgtggtg ttctgcctgc tgcaagccgg acctctggat      60
acagccgtgt ctcagacccc taagtacctg gtcacccaga tgggcaacga caagagcatc     120
aagtgcgagc agaacctggg ccacgacacc atgtactggt acaagcagga cagcaagaaa     180
ttcctgaaga tcatgttcag ctacaacaac aaagagctga tcatcaacga cagtgccc       240
aacagattca gccctaagag ccccgataag gcccacctga acctgcacat caacagcctg     300
gaactgggcg acagcgccgt gtactttgt gccagcagcc agttctggga tggcgctggc      360
gacgagcagt attttggccc tggcaccaga ctgaccgtga ccgaggacct gaacaaggtg     420
ttccctccgg aggtggccgt gttcgagccc agcaaagccg agatcgcgca cacccagaag     480
gccaccctgg tgtgcctggc caccggcttc ttccccgacc acgtggagct gagctggtgg     540
gtgaacggca aggaggtgca cagcggcgtg agcaccgacc ccagcccct gaaggagcag      600
cccgccctga acgacagccg ctactgcctg agcagccgcc tgcgcgtgag cgccaccttc     660
tggcagaacc ccgcaacca cttccgctgc caggtgcagt tctacggcct gagcgagaac      720
gacgagtgga cccaggaccg cgccaagccc gtgacccaga tcgtgagcgc cgaggcctgg     780
ggccgccccg actgcggcat taccagcgcg agctaccatc agggcgtgct gagcgccacc     840
atcctgtacg agatcctgct gggcaaggcc accctgtacg ccgtgctggt gagcgccctg     900
gtgctgatgg cgatggtgaa gcgcaaggac ttctga                              936
```

<210> SEQ ID NO 56
<211> LENGTH: 10
<212> TYPE: PRT
<213> ORGANISM: Homo sapiens

<400> SEQUENCE: 56

Lys Leu Tyr Gly Leu Asp Trp Ala Glu Leu
1               5                   10

<210> SEQ ID NO 57
<211> LENGTH: 272
<212> TYPE: PRT
<213> ORGANISM: Artificial Sequence
<220> FEATURE:
<223> OTHER INFORMATION: murinized

<400> SEQUENCE: 57

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Ser Gly Asp Ser Ala Gly Asn Met Leu Thr Phe Gly Gly Gly
        115                 120                 125

Thr Arg Leu Met Val Lys Pro His Ile Gln Asn Pro Glu Pro Ala Val
    130                 135                 140

Tyr Gln Leu Lys Asp Pro Arg Ser Gln Asp Ser Thr Leu Cys Leu Phe
145                 150                 155                 160

Thr Asp Phe Asp Ser Gln Ile Asn Val Pro Lys Thr Met Glu Ser Gly
                165                 170                 175

Thr Phe Ile Thr Asp Lys Thr Val Leu Asp Met Lys Ala Met Asp Ser
            180                 185                 190

Lys Ser Asn Gly Ala Ile Ala Trp Ser Asn Gln Thr Ser Phe Thr Cys
        195                 200                 205

Gln Asp Ile Phe Lys Glu Thr Asn Ala Thr Tyr Pro Ser Ser Asp Val
    210                 215                 220

Pro Cys Asp Ala Thr Leu Thr Glu Lys Ser Phe Glu Thr Asp Met Asn
225                 230                 235                 240

Leu Asn Phe Gln Asn Leu Ser Val Met Gly Leu Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 58
<211> LENGTH: 308
<212> TYPE: PRT
<213> ORGANISM: Artificial Sequence
<220> FEATURE:

-continued

<223> OTHER INFORMATION: murinized

<400> SEQUENCE: 58

Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
    50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
            100                 105                 110

Ser Asp Trp Asp Arg Ser Gly Asp Lys Glu Thr Gln Tyr Phe Gly Pro
        115                 120                 125

Gly Thr Arg Leu Leu Val Leu Glu Asp Leu Arg Asn Val Thr Pro Pro
    130                 135                 140

Lys Val Thr Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr His Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Gly Leu Val Leu Met Ala Met Val Lys
    290                 295                 300

Lys Lys Asn Ser
305

<210> SEQ ID NO 59
<211> LENGTH: 273
<212> TYPE: PRT
<213> ORGANISM: Artificial Sequence
<220> FEATURE:
<223> OTHER INFORMATION: murinized

<400> SEQUENCE: 59

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

```
Val Gln Glu Lys Glu Ala Val Thr Leu Asp Cys Thr Tyr Asp Thr Ser
            35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
                100                 105                 110

Ala Met Ser Gly Gly Tyr Thr Gly Gly Phe Lys Thr Ile Phe Gly Ala
            115                 120                 125

Gly Thr Arg Leu Phe Val Lys Ala Asn Ile Gln Asn Pro Glu Pro Ala
        130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Thr Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser Val Met Gly Leu Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 60
<211> LENGTH: 304
<212> TYPE: PRT
<213> ORGANISM: Artificial Sequence
<220> FEATURE:
<223> OTHER INFORMATION: murinized

<400> SEQUENCE: 60

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
            35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
                100                 105                 110
```

```
Ser Gly Gly Asp Gly Asp Glu Gln Phe Phe Gly Pro Gly Thr Arg Leu
            115                 120                 125

Thr Val Leu Glu Asp Leu Arg Asn Val Thr Pro Pro Lys Val Thr Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Ser Thr Asp Pro Gln
                180                 185                 190

Ala Tyr Lys Glu Ser Asn Tyr Ser Tyr Cys Leu Ser Ser Arg Leu Arg
            195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr His Gln Gly Val Leu Ser Ala
                260                 265                 270

Thr Ile Leu Tyr Glu Ile Leu Leu Gly Lys Ala Thr Leu Tyr Ala Val
            275                 280                 285

Leu Val Ser Gly Leu Val Leu Met Ala Met Val Lys Lys Lys Asn Ser
            290                 295                 300

<210> SEQ ID NO 61
<211> LENGTH: 269
<212> TYPE: PRT
<213> ORGANISM: Artificial Sequence
<220> FEATURE:
<223> OTHER INFORMATION: murinized

<400> SEQUENCE: 61

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Arg Gly Thr Gly Phe Gln Lys Leu Val Phe Gly Thr Gly Thr Arg Leu
            115                 120                 125

Leu Val Ser Pro Asn Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175
```

```
Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265
```

<210> SEQ ID NO 62
<211> LENGTH: 307
<212> TYPE: PRT
<213> ORGANISM: Artificial Sequence
<220> FEATURE:
<223> OTHER INFORMATION: murinized

<400> SEQUENCE: 62

```
Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Gln Phe Trp Asp Gly Ala Gly Asp Glu Gln Tyr Phe Gly Pro Gly
        115                 120                 125

Thr Arg Leu Thr Val Thr Glu Asp Leu Arg Asn Val Thr Pro Pro Lys
130                 135                 140

Val Thr Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr His Gln Gly Val
            260                 265                 270
```

```
Leu Ser Ala Thr Ile Leu Tyr Glu Ile Leu Leu Gly Lys Ala Thr Leu
        275                 280                 285

Tyr Ala Val Leu Val Ser Gly Leu Val Leu Met Ala Met Val Lys Lys
        290                 295                 300

Lys Asn Ser
305

<210> SEQ ID NO 63
<211> LENGTH: 21
<212> TYPE: DNA
<213> ORGANISM: Artificial Sequence
<220> FEATURE:
<223> OTHER INFORMATION: human optimized

<400> SEQUENCE: 63
acttcagacc agtcgtacgg t                                             21

<210> SEQ ID NO 64
<211> LENGTH: 24
<212> TYPE: DNA
<213> ORGANISM: Artificial Sequence
<220> FEATURE:
<223> OTHER INFORMATION: human optimized

<400> SEQUENCE: 64
cagggatcgt acgacgagca gaac                                          24

<210> SEQ ID NO 65
<211> LENGTH: 42
<212> TYPE: DNA
<213> ORGANISM: Artificial Sequence
<220> FEATURE:
<223> OTHER INFORMATION: human optimized

<400> SEQUENCE: 65
tgcgcaatgt ccggcgatag cgcaggaaac atgctgactt tc                      42

<210> SEQ ID NO 66
<211> LENGTH: 15
<212> TYPE: DNA
<213> ORGANISM: Artificial Sequence
<220> FEATURE:
<223> OTHER INFORMATION: human optimized

<400> SEQUENCE: 66
aagggccacg accgc                                                    15

<210> SEQ ID NO 67
<211> LENGTH: 18
<212> TYPE: DNA
<213> ORGANISM: Artificial Sequence
<220> FEATURE:
<223> OTHER INFORMATION: human optimized

<400> SEQUENCE: 67
tccttcgacg tgaaggac                                                 18

<210> SEQ ID NO 68
<211> LENGTH: 51
<212> TYPE: DNA
<213> ORGANISM: Artificial Sequence
<220> FEATURE:
<223> OTHER INFORMATION: human optimized

<400> SEQUENCE: 68
```

```
tgtgccacct cggattggga ccgatccggc gacaaggaaa ctcagtactt c        51
```

<210> SEQ ID NO 69
<211> LENGTH: 831
<212> TYPE: DNA
<213> ORGANISM: Artificial Sequence
<220> FEATURE:
<223> OTHER INFORMATION: human optimized

<400> SEQUENCE: 69

```
atgagcctct cttccctgct caaagtggtc actgcctccc tgtggctggg accgggaatc    60
gcccagaaga tcactcagac ccagcctgga atgttcgtgc aagagaaaga ggccgtgacc   120
ctggattgta cttatgacac ttcagaccag tcgtacggtt tgttctggta caagcagccg   180
tcctccggag aaatgatctt cctgatctac cagggatcgt acgacgagca gaacgctacc   240
gagggcagat attccctcaa cttccaaaag gcccggaaat ccgcgaacct cgtgatctcg   300
gcctcacaac ttggggactc cgctatgtat ttctgcgcaa tgtccggcga tagcgcagga   360
aacatgctga ctttcggcgg tggaactagg ctgatggtca agccccacat tcaaaaccct   420
gacccagcag tctaccagtt gcgggattcc aagtcttccg ataaatccgt gtgtctcttt   480
acagacttcg atagccagac caacgtgtcc cagagcaaag acagcgacgt gtacattact   540
gacaagactg tgctggacat gcggtccatg gacttcaaga gcaactccgc cgtcgcttgg   600
tccaacaagt ctgactttgc gtgcgcgaac gctttcaaca acagcattat cccggaggac   660
acctttttcc cttcccccga gtcaagctgc gatgtcaagc ttgtggaaaa gtcgttcgaa   720
accgacacca acctgaactt ccagaacctg tccgtcatcg ggttccgcat tctgctgctg   780
aaggtcgccg gcttcaatct cctgatgact ctccgcttgt ggtcctcata a            831
```

<210> SEQ ID NO 70
<211> LENGTH: 936
<212> TYPE: DNA
<213> ORGANISM: Artificial Sequence
<220> FEATURE:
<223> OTHER INFORMATION: human optimized

<400> SEQUENCE: 70

```
atggcgtccc tgctgttctt ctgcggtgcc ttctaccttc tgggaaccgg ctcgatggac    60
gccgacgtga cccaaacccc tcgcaaccgc atcaccaaga ctggaaagcg gatcatgctg   120
gaatgctccc agaccaaggg ccacgaccgc atgtactggt acagacagga cccgggtctg   180
ggattgcgcc tgatctacta ctccttcgac gtgaaggaca tcaacaaggg ggagatctcc   240
gatggatact cagtctcgag acaagcccag gctaagtttt ccctgtccct cgaatccgcc   300
attcccaatc agaccgcgct gtacttctgt gccacctcgg attgggaccg atccggcgac   360
aaggaaactc agtacttcgg accaggaacc aggctcctgg tgctggagga tctgaacaag   420
gtgttcccgc cggaagtggc agtgttcgag ccatccgaag ccgagatctc gcatacgcag   480
aaggccaccc tcgtgtgcct ggccactggg tttttccctg accacgtgga gctctcgtgg   540
tgggtcaacg gaaaggaagt gcacagcggt gtctcaaccg acccgcaacc tctcaaggaa   600
cagcccgcgc tcaatgattc gcggtactgc ctgagcagcc ggctcagagt gtccgccact   660
ttctggcaaa acccgcggaa ccatttccgg tgccaagtgc aattctacgg gctgtcggaa   720
aacgacgaat ggacccagga cagggccaag cccgtgaccc agattgtgtc cgctgaagcc   780
tgggggagag ctgattgcgg tttcaccagc gtgtcgtatc agcagggcgt gctgtcagcc   840
accattctgt acgaaatcct cctggggaag gccacactgt acgccgtgct cgtgtccgcc   900
```
ctggtgctga tggccatggt caagcggaag gacttc                          936

<210> SEQ ID NO 71
<211> LENGTH: 21
<212> TYPE: DNA
<213> ORGANISM: Artificial Sequence
<220> FEATURE:
<223> OTHER INFORMATION: human optimized

<400> SEQUENCE: 71
acctccgacc cgtcctacgg g                                          21

<210> SEQ ID NO 72
<211> LENGTH: 24
<212> TYPE: DNA
<213> ORGANISM: Artificial Sequence
<220> FEATURE:
<223> OTHER INFORMATION: human optimized

<400> SEQUENCE: 72
caaggctcct atgatcagca gaac                                       24

<210> SEQ ID NO 73
<211> LENGTH: 45
<212> TYPE: DNA
<213> ORGANISM: Artificial Sequence
<220> FEATURE:
<223> OTHER INFORMATION: human optimized

<400> SEQUENCE: 73
tgtgccatgt cgggcggata caccggggga ttcaagacca ttttc                45

<210> SEQ ID NO 74
<211> LENGTH: 15
<212> TYPE: DNA
<213> ORGANISM: Artificial Sequence
<220> FEATURE:
<223> OTHER INFORMATION: human optimized

<400> SEQUENCE: 74
tctggcgacc tctcc                                                 15

<210> SEQ ID NO 75
<211> LENGTH: 18
<212> TYPE: DNA
<213> ORGANISM: Artificial Sequence
<220> FEATURE:
<223> OTHER INFORMATION: human optimized

<400> SEQUENCE: 75
tactacaacg gagaggag                                              18

<210> SEQ ID NO 76
<211> LENGTH: 39
<212> TYPE: DNA
<213> ORGANISM: Artificial Sequence
<220> FEATURE:
<223> OTHER INFORMATION: human optimized

<400> SEQUENCE: 76
tgcgcaagca gcggtggtga cggggatgaa cagttctttt                      39

<210> SEQ ID NO 77
<211> LENGTH: 834
<212> TYPE: DNA

<213> ORGANISM: Artificial Sequence
<220> FEATURE:
<223> OTHER INFORMATION: human optimized

<400> SEQUENCE: 77

```
atgtcccttc gctcactgct gaaagtggtc actgcgagcc tgtggctggg accaggcatt      60
gctcaaaaga tcacccagac tcagcctggg atgttcgtgc aagagaagga agccgtgacc     120
ctcgactgca cttacgacac ctccgacccg tcctacgggc tgttctggta caagcagccg     180
tcctccggag agatgatctt cctcatctac caaggctcct atgatcagca gaacgccacc     240
gaaggacgct acagcctgaa cttccagaag gctcggaagt cggcgaacct cgtgatcagc     300
gcatcccaac tgggggacag cgccatgtac ttctgtgcca tgtcgggcgg atacaccggg     360
ggattcaaga ccattttcgg ggccggcact agactgttcg tgaaggccaa catccagaat     420
cctgatccgg cggtgtatca gctgcgcgac tccaagtctt ccgataaatc cgtgtgtctc     480
tttacagact tcgactccca aaccaacgtg tcacagtcca aggacagcga tgtgtacatc     540
accgacaaaa ccgtgctgga catgcggtcc atggacttca agtcaaacag cgcagtcgcc     600
tggtccaaca gtccgacttc gcctgtgcg aacgccttca caactccat cattccggaa      660
gataccttt tcccttcacc tgagtcgagc tgtgatgtga agctcgtgga aaagtcgttt     720
gaaacggaca ccaacctgaa ctttcagaac ctgtccgtga ttggtttccg catcctgctg     780
ctgaaggtcg ccggcttcaa cttgctgatg acgctccggc tgtggtcctc gtaa          834
```

<210> SEQ ID NO 78
<211> LENGTH: 930
<212> TYPE: DNA
<213> ORGANISM: Artificial Sequence
<220> FEATURE:
<223> OTHER INFORMATION: human optimized

<400> SEQUENCE: 78

```
atgggattcc gccttctgtg ctgcgtggcc ttctgcttgc ttggagctgg tcccgtcgac      60
tcgggagtga cccagacgcc gaagcacttg attaccgcta ctgggcagcg cgtgactctg     120
cgatgctcac cacggtctgg cgacctctcc gtgtactggt atcagcagag cctggaccag     180
ggactgcagt tcctgatcca gtactacaac ggagaggagc gggctaaggg aaacatactg     240
gagcggttct cggcgcaaca attccccgat ctgcactccg aactgaacct gtcctccctg     300
gaattgggag actccgccct gtacttctgc gcaagcagcg gtggtgacgg ggatgaacag     360
ttctttggcc ctggaaccag actcaccgtg ctcgaggacc tcaagaacgt gttcccaccc     420
gaagtcgcgg tgttcgagcc ctccgaagcg gaaatcagcc atactcagaa agccactctc     480
gtgtgcctgg ccaccggatt ctacccggac acgtcgagc tctcttggtg ggtgaacggg     540
aaagaggtcc acagcggcgt gagcactgat ccgcagccgc tgaaggaaca acccgccttg     600
aacgactcgc ggtactgtct gtcctcccgg ctgagagtgt cggccacctt ctggcaaaac     660
cccaggaacc actttaggtg ccaagtccag ttctacggcc tgagcgaaaa cgatgagtgg     720
acccaggaca gagccaagcc tgtgacccag attgtgtcag ccgaggcttg gggtagagca     780
gactgcggat tcacctccga gtcctaccaa caaggcgtcc tctcggcgac cattctgtac     840
gaaatcctgc ttgggaaggc cactctgtac gccgtgctgg tgtccgccct ggtgctgatg     900
gccatggtca agcggaagga ctcccggggg                                      930
```

<210> SEQ ID NO 79
<211> LENGTH: 18

<212> TYPE: DNA
<213> ORGANISM: Artificial Sequence
<220> FEATURE:
<223> OTHER INFORMATION: human optimized

<400> SEQUENCE: 79
gactcagcat caaactat                                          18

<210> SEQ ID NO 80
<211> LENGTH: 21
<212> TYPE: DNA
<213> ORGANISM: Artificial Sequence
<220> FEATURE:
<223> OTHER INFORMATION: human optimized

<400> SEQUENCE: 80
atccgctcca acgtcggaga g                                      21

<210> SEQ ID NO 81
<211> LENGTH: 42
<212> TYPE: DNA
<213> ORGANISM: Artificial Sequence
<220> FEATURE:
<223> OTHER INFORMATION: human optimized

<400> SEQUENCE: 81
tgtgcggcct cgaggggcac tgggtttcag aagctcgtgt tc               42

<210> SEQ ID NO 82
<211> LENGTH: 15
<212> TYPE: DNA
<213> ORGANISM: Artificial Sequence
<220> FEATURE:
<223> OTHER INFORMATION: human optimized

<400> SEQUENCE: 82
ctcggacacg acacc                                             15

<210> SEQ ID NO 83
<211> LENGTH: 18
<212> TYPE: DNA
<213> ORGANISM: Artificial Sequence
<220> FEATURE:
<223> OTHER INFORMATION: human optimized

<400> SEQUENCE: 83
tacaacaaca aggaactg                                          18

<210> SEQ ID NO 84
<211> LENGTH: 48
<212> TYPE: DNA
<213> ORGANISM: Artificial Sequence
<220> FEATURE:
<223> OTHER INFORMATION: human optimized

<400> SEQUENCE: 84
tgcgcgtcca gccagttctg ggacggagcg ggcgacgaac agtacttc         48

<210> SEQ ID NO 85
<211> LENGTH: 819
<212> TYPE: DNA
<213> ORGANISM: Artificial Sequence
<220> FEATURE:
<223> OTHER INFORMATION: human optimized

<400> SEQUENCE: 85

| | |
|---|---|
| atgacgtcca ttagagccgt gttcattttc ctgtggctgc aactggacct cgtgaatgga | 60 |
| gaaaacgtcg agcagcaccc atccaccctg agcgtgcagg agggagactc cgcagtcatc | 120 |
| aagtgcactt actccgactc agcatcaaac tatttcccgt ggtataagca ggaactcgga | 180 |
| aagcggcctc agctcatcat tgacatccgc tccaacgtcg agagaagaa ggaccagaga | 240 |
| attgccgtga cactcaacaa gaccgccaag catttctccc ttcacatcac cgaaacccag | 300 |
| cccgaggaca cgcccgtcta cttttgtgcg gcctcgaggg cactgggtt tcagaagctc | 360 |
| gtgttcggca ctgggacccg gctgctggtg tcgccaaaca tccagaatcc agaccccgcg | 420 |
| gtgtaccagc tgagagactc gaagtcttcc gataaatccg tgtgtctctt tacagacttc | 480 |
| gatagccaga ctaacgtgtc ccagtccaag gactccgatg tgtacatcac cgacaagact | 540 |
| gtgctggata tgcggagcat ggactttaag tccaattcag cggtcgcgtg gagcaacaag | 600 |
| tccgacttcg cctgcgctaa cgctttcaac aactccatta cccggagga taccttcttc | 660 |
| ccgtcaccgg aatcctcgtg cgacgtgaag ctggtcgaga agtccttcga aaccgatacc | 720 |
| aacctgaact tccaaaacct ctccgtgatc ggcttcagaa tcctgctgct gaaagtggct | 780 |
| ggcttcaatt tgctgatgac cctgcggctc tggagcagc | 819 |

<210> SEQ ID NO 86
<211> LENGTH: 930
<212> TYPE: DNA
<213> ORGANISM: Artificial Sequence
<220> FEATURE:
<223> OTHER INFORMATION: human optimized

<400> SEQUENCE: 86

| | |
|---|---|
| atgggttgtc ggttgctgtg ttgcgtcgtg ttctgccttc ttcaagctgg tcctctcgat | 60 |
| actgccgtga gccaaacccc taagtacctt gtcacccaaa tgggcaacga caagtccatc | 120 |
| aaatgcgaac agaacctcgg acacgacacc atgtactggt acaaacagga ttccaagaag | 180 |
| ttcctgaaga ttatgttctc atacaacaac aaggaactga ttatcaacga aactgtgccg | 240 |
| aaccggttct caccgaagtc gcctgacaag gctcatctca acttgcatat caactcgctg | 300 |
| gagctcggcg actccgccgt gtacttctgc gcgtccagcc agttctggga cggagcgggc | 360 |
| gacgaacagt acttcggccc gggcactcgg ctgaccgtga ccgaagatct gaacaaagtg | 420 |
| ttcccccccg aagtggccgt gttcgaacct ccgaggccg agatcagcca cacccaaaag | 480 |
| gccactctgg tctgcctggc caccggtttc ttccccgatc acgtggaact gtcttggtgg | 540 |
| gtgaacggaa agaagtgca ctcgggggtg tccacggacc cccagcctct gaaggaacag | 600 |
| ccggcactga atgactcacg ctactgtctg tcgtcacggc tgcgcgtgtc ggccaccttc | 660 |
| tggcaaaacc cgcgaaacca ctttcgctgc caagtcagt tttacgggct ttccgagaac | 720 |
| gacgagtgga ctcaggacag agcgaagccc gtgacccaaa tcgtgtccgc cgaggcctgg | 780 |
| ggacgcgccg actgcggttt cacctccgtg agctaccaac agggcgtgct gtcagctacc | 840 |
| atcctttacg agatcctcct gggaaaggcc accctctacg ccgtcctggt gtccgcactg | 900 |
| gtgctgatgg ctatggtcaa gcggaaggat | 930 |

<210> SEQ ID NO 87
<211> LENGTH: 276
<212> TYPE: PRT
<213> ORGANISM: Homo sapiens

<400> SEQUENCE: 87

Met Ser Leu Ser Ser Leu Leu Lys Val Val Thr Ala Ser Leu Trp Leu

-continued

```
              1               5              10              15
            Gly Pro Gly Ile Ala Gln Lys Ile Thr Gln Thr Gln Pro Gly Met Phe
                           20                  25                  30
            Val Gln Glu Lys Glu Ala Val Thr Leu Asp Cys Thr Tyr Asp Thr Ser
                           35                  40                  45
            Asp Gln Ser Tyr Gly Leu Phe Trp Tyr Lys Gln Pro Ser Ser Gly Glu
                           50                  55                  60
            Met Ile Phe Leu Ile Tyr Gln Gly Ser Tyr Asp Glu Gln Asn Ala Thr
             65                  70                  75                  80
            Glu Gly Arg Tyr Ser Leu Asn Phe Gln Lys Ala Arg Lys Ser Ala Asn
                           85                  90                  95
            Leu Val Ile Ser Ala Ser Gln Leu Gly Asp Ser Ala Met Tyr Phe Cys
                          100                 105                 110
            Ala Met Ser Gly Asp Ser Ala Gly Asn Met Leu Thr Phe Gly Gly Gly
                          115                 120                 125
            Thr Arg Leu Met Val Lys Pro His Ile Gln Asn Pro Asp Pro Ala Val
                          130                 135                 140
            Tyr Gln Leu Arg Asp Ser Lys Ser Ser Asp Lys Ser Val Cys Leu Phe
            145                 150                 155                 160
            Thr Asp Phe Asp Ser Gln Thr Asn Val Ser Gln Ser Lys Asp Ser Asp
                          165                 170                 175
            Val Tyr Ile Thr Asp Lys Thr Val Leu Asp Met Arg Ser Met Asp Phe
                          180                 185                 190
            Lys Ser Asn Ser Ala Val Ala Trp Ser Asn Lys Ser Asp Phe Ala Cys
                          195                 200                 205
            Ala Asn Ala Phe Asn Asn Ser Ile Ile Pro Glu Asp Thr Phe Phe Pro
                          210                 215                 220
            Ser Pro Glu Ser Ser Cys Asp Val Lys Leu Val Glu Lys Ser Phe Glu
            225                 230                 235                 240
            Thr Asp Thr Asn Leu Asn Phe Gln Asn Leu Ser Val Ile Gly Phe Arg
                          245                 250                 255
            Ile Leu Leu Leu Lys Val Ala Gly Phe Asn Leu Leu Met Thr Leu Arg
                          260                 265                 270
            Leu Trp Ser Ser
                          275

<210> SEQ ID NO 88
<211> LENGTH: 312
<212> TYPE: PRT
<213> ORGANISM: Homo sapiens

<400> SEQUENCE: 88

Met Ala Ser Leu Leu Phe Phe Cys Gly Ala Phe Tyr Leu Leu Gly Thr
             1               5                  10                  15
            Gly Ser Met Asp Ala Asp Val Thr Gln Thr Pro Arg Asn Arg Ile Thr
                           20                  25                  30
            Lys Thr Gly Lys Arg Ile Met Leu Glu Cys Ser Gln Thr Lys Gly His
                           35                  40                  45
            Asp Arg Met Tyr Trp Tyr Arg Gln Asp Pro Gly Leu Gly Leu Arg Leu
                           50                  55                  60
            Ile Tyr Tyr Ser Phe Asp Val Lys Asp Ile Asn Lys Gly Glu Ile Ser
             65                  70                  75                  80
            Asp Gly Tyr Ser Val Ser Arg Gln Ala Gln Ala Lys Phe Ser Leu Ser
                           85                  90                  95
```

```
Leu Glu Ser Ala Ile Pro Asn Gln Thr Ala Leu Tyr Phe Cys Ala Thr
                100                 105                 110

Ser Asp Trp Asp Arg Ser Gly Asp Lys Glu Thr Gln Tyr Phe Gly Pro
            115                 120                 125

Gly Thr Arg Leu Leu Val Leu Glu Asp Leu Asn Lys Val Phe Pro Pro
        130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
            245                 250                 255

Ser Ala Glu Ala Trp Gly Arg Ala Asp Cys Gly Phe Thr Ser Val Ser
        260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
290                 295                 300

Ala Met Val Lys Arg Lys Asp Phe
305                 310

<210> SEQ ID NO 89
<211> LENGTH: 277
<212> TYPE: PRT
<213> ORGANISM: Homo sapiens

<400> SEQUENCE: 89

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
                100                 105                 110

Ala Met Ser Gly Gly Tyr Thr Gly Phe Lys Thr Ile Phe Gly Ala
            115                 120                 125

Gly Thr Arg Leu Phe Val Lys Ala Asn Ile Gln Asn Pro Asp Pro Ala
        130                 135                 140

Val Tyr Gln Leu Arg Asp Ser Lys Ser Ser Asp Lys Ser Val Cys Leu
145                 150                 155                 160
```

```
Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
            275

<210> SEQ ID NO 90
<211> LENGTH: 310
<212> TYPE: PRT
<213> ORGANISM: Homo sapiens

<400> SEQUENCE: 90

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Gly Gly Asp Gly Asp Glu Gln Phe Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
```

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
        290                 295                 300

Arg Lys Asp Ser Arg Gly
305                 310

<210> SEQ ID NO 91
<211> LENGTH: 273
<212> TYPE: PRT
<213> ORGANISM: Homo sapiens

<400> SEQUENCE: 91

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Arg Gly Thr Gly Phe Gln Lys Leu Val Phe Gly Thr Gly Thr Arg Leu
        115                 120                 125

Leu Val Ser Pro Asn Ile Gln Asn Pro Asp Pro Ala Val Tyr Gln Leu
130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 92
<211> LENGTH: 310
<212> TYPE: PRT

<213> ORGANISM: Homo sapiens

<400> SEQUENCE: 92

```
Met Gly Cys Arg Leu Leu Cys Cys Val Val Phe Cys Leu Leu Gln Ala
1               5                   10                  15
Gly Pro Leu Asp Thr Ala Val Ser Gln Thr Pro Lys Tyr Leu Val Thr
            20                  25                  30
Gln Met Gly Asn Asp Lys Ser Ile Lys Cys Glu Gln Asn Leu Gly His
        35                  40                  45
Asp Thr Met Tyr Trp Tyr Lys Gln Asp Ser Lys Lys Phe Leu Lys Ile
    50                  55                  60
Met Phe Ser Tyr Asn Asn Lys Glu Leu Ile Ile Asn Glu Thr Val Pro
65                  70                  75                  80
Asn Arg Phe Ser Pro Lys Ser Pro Asp Lys Ala His Leu Asn Leu His
                85                  90                  95
Ile Asn Ser Leu Glu Leu Gly Asp Ser Ala Val Tyr Phe Cys Ala Ser
            100                 105                 110
Ser Gln Phe Trp Asp Gly Ala Gly Asp Glu Gln Tyr Phe Gly Pro Gly
        115                 120                 125
Thr Arg Leu Thr Val Thr Glu Asp Leu Asn Lys Val Phe Pro Pro Glu
    130                 135                 140
Val Ala Val Phe Glu Pro Ser Glu Ala Glu Ile Ser His Thr Gln Lys
145                 150                 155                 160
Ala Thr Leu Val Cys Leu Ala Thr Gly Phe Phe Pro Asp His Val Glu
                165                 170                 175
Leu Ser Trp Trp Val Asn Gly Lys Glu Val His Ser Gly Val Ser Thr
            180                 185                 190
Asp Pro Gln Pro Leu Lys Glu Gln Pro Ala Leu Asn Asp Ser Arg Tyr
        195                 200                 205
Cys Leu Ser Ser Arg Leu Arg Val Ser Ala Thr Phe Trp Gln Asn Pro
    210                 215                 220
Arg Asn His Phe Arg Cys Gln Val Gln Phe Tyr Gly Leu Ser Glu Asn
225                 230                 235                 240
Asp Glu Trp Thr Gln Asp Arg Ala Lys Pro Val Thr Gln Ile Val Ser
                245                 250                 255
Ala Glu Ala Trp Gly Arg Ala Asp Cys Gly Phe Thr Ser Val Ser Tyr
            260                 265                 270
Gln Gln Gly Val Leu Ser Ala Thr Ile Leu Tyr Glu Ile Leu Leu Gly
        275                 280                 285
Lys Ala Thr Leu Tyr Ala Val Leu Val Ser Ala Leu Val Leu Met Ala
    290                 295                 300
Met Val Lys Arg Lys Asp
305                 310
```

<210> SEQ ID NO 93
<211> LENGTH: 1833
<212> TYPE: DNA
<213> ORGANISM: Artificial Sequence
<220> FEATURE:
<223> OTHER INFORMATION: human optimized

<400> SEQUENCE: 93

```
atggcgtccc tgctgttctt ctgcggtgcc ttctaccttc tgggaaccgg ctcgatggac    60
gccgacgtga cccaaacccc tcgcaaccgc atcaccaaga ctggaaagcg gatcatgctg   120
gaatgctccc agaccaaggg ccacgaccgc atgtactggt acagacagga cccgggtctg   180
```

```
ggattgcgcc tgatctacta ctccttcgac gtgaaggaca tcaacaaggg ggagatctcc    240
gatggatact cagtctcgag acaagcccag gctaagtttt ccctgtccct cgaatccgcc    300
attcccaatc agaccgcgct gtacttctgt gccacctcgg attgggaccg atccggcgac    360
aaggaaactc agtacttcgg accaggaacc aggctcctgg tgctggagga tctgaacaag    420
gtgttcccgc cggaagtggc agtgttcgag ccatccgaag ccgagatctc gcatacgcag    480
aaggccaccg tcgtgtgcct ggccactggg tttttccctg accacgtgga gctctcgtgg    540
tgggtcaacg gaaaggaagt gcacagcggt gtctcaaccg acccgcaacc tctcaaggaa    600
cagcccgcgc tcaatgattc gcggtactgc ctgagcagcc ggctcagagt gtccgccact    660
ttctggcaaa accgcggaaa ccatttccgg tgccaagtgc aattctacgg gctgtcggaa    720
aacgacgaat ggacccagga cagggccaag cccgtgaccc agattgtgtc cgctgaagcc    780
tgggggagag ctgattgcgg tttcaccagc gtgtcgtatc agcagggcgt gctgtcagcc    840
accattctgt acgaaatcct cctggggaag gccacactgt acgccgtgct cgtgtccgcc    900
ctggtgctga tggccatggt caagcggaag gacttcggca gcggagctac caacttctcc    960
ctgctgaagc aggccggcga tgtggaagaa atcccggac ctatgagcct ctcttccctg   1020
ctcaaagtgg tcactgcctc cctgtggctg gaccgggaa tcgcccagaa gatcactcag   1080
acccagcctg gaatgttcgt gcaagagaaa gaggccgtga ccctggattg tacttatgac   1140
acttcagacc agtcgtacgg tttgttctgg tacaagcagc cgtcctccgg agaaatgatc   1200
ttcctgatct accagggatc gtacgacgag cagaacgcta ccgagggcag atattccctc   1260
aacttccaaa aggcccggaa atccgcgaac ctcgtgatct cggcctcaca acttggggac   1320
tccgctatgt atttctgcgc aatgtccggc gatagcgcag gaaacatgct gactttcggc   1380
ggtggaacta ggctgatggt caagccccac attcaaaacc ctgacccagc agtctaccag   1440
ttgcgggatt ccaagtcttc cgataaatcc gtgtgtctct ttacagactt cgatagccag   1500
accaacgtgt cccagagcaa agacagcgac gtgtacatta ctgacaagac tgtgctggac   1560
atgcggtcca tggacttcaa gagcaactcc gccgtcgctt ggtccaacaa gtctgacttt   1620
gcgtgcgcga acgctttcaa caacagcatt atcccggagg acacctttt ccttccccc    1680
gagtcaagct gcgatgtcaa gcttgtggaa aagtcgttcg aaaccgacac caacctgaac   1740
ttccagaacc tgtccgtcat cgggttccgc attctgctgc tgaaggtcgc cggcttcaat   1800
ctcctgatga ctctccgctt gtggtcctca taa                                1833
```

<210> SEQ ID NO 94
<211> LENGTH: 610
<212> TYPE: PRT
<213> ORGANISM: Artificial Sequence
<220> FEATURE:
<223> OTHER INFORMATION: human optimized

<400> SEQUENCE: 94

```
Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
    50                  55                  60
```

-continued

```
Ile Tyr Tyr Ser Phe Asp Val Lys Asp Ile Asn Lys Gly Glu Ile Ser
 65                  70                  75                  80

Asp Gly Tyr Ser Val Ser Arg Gln Ala Gln Ala Lys Phe Ser Leu Ser
                 85                  90                  95

Leu Glu Ser Ala Ile Pro Asn Gln Thr Ala Leu Tyr Phe Cys Ala Thr
            100                 105                 110

Ser Asp Trp Asp Arg Ser Gly Asp Lys Glu Thr Gln Tyr Phe Gly Pro
        115                 120                 125

Gly Thr Arg Leu Leu Val Leu Glu Asp Leu Asn Lys Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Phe Gly Ser Gly Ala Thr Asn Phe Ser
305                 310                 315                 320

Leu Leu Lys Gln Ala Gly Asp Val Glu Glu Asn Pro Gly Pro Met Ser
                325                 330                 335

Leu Ser Ser Leu Leu Lys Val Val Thr Ala Ser Leu Trp Leu Gly Pro
            340                 345                 350

Gly Ile Ala Gln Lys Ile Thr Gln Thr Gln Pro Gly Met Phe Val Gln
        355                 360                 365

Glu Lys Glu Ala Val Thr Leu Asp Cys Thr Tyr Asp Thr Ser Asp Gln
    370                 375                 380

Ser Tyr Gly Leu Phe Trp Tyr Lys Gln Pro Ser Ser Gly Glu Met Ile
385                 390                 395                 400

Phe Leu Ile Tyr Gln Gly Ser Tyr Asp Glu Gln Asn Ala Thr Glu Gly
                405                 410                 415

Arg Tyr Ser Leu Asn Phe Gln Lys Ala Arg Lys Ser Ala Asn Leu Val
            420                 425                 430

Ile Ser Ala Ser Gln Leu Gly Asp Ser Ala Met Tyr Phe Cys Ala Met
        435                 440                 445

Ser Gly Asp Ser Ala Gly Asn Met Leu Thr Phe Gly Gly Gly Thr Arg
    450                 455                 460

Leu Met Val Lys Pro His Ile Gln Asn Pro Asp Pro Ala Val Tyr Gln
465                 470                 475                 480

Leu Arg Asp Ser Lys Ser Ser Asp Lys Ser Val Cys Leu Phe Thr Asp
```

```
                485                 490                 495
Phe Asp Ser Gln Thr Asn Val Ser Gln Ser Lys Asp Ser Asp Val Tyr
                500                 505                 510

Ile Thr Asp Lys Thr Val Leu Asp Met Arg Ser Met Asp Phe Lys Ser
            515                 520                 525

Asn Ser Ala Val Ala Trp Ser Asn Lys Ser Asp Phe Ala Cys Ala Asn
        530                 535                 540

Ala Phe Asn Asn Ser Ile Ile Pro Glu Asp Thr Phe Phe Pro Ser Pro
545                 550                 555                 560

Glu Ser Ser Cys Asp Val Lys Leu Val Glu Lys Ser Phe Glu Thr Asp
                565                 570                 575

Thr Asn Leu Asn Phe Gln Asn Leu Ser Val Ile Gly Phe Arg Ile Leu
            580                 585                 590

Leu Leu Lys Val Ala Gly Phe Asn Leu Leu Met Thr Leu Arg Leu Trp
        595                 600                 605

Ser Ser
    610

<210> SEQ ID NO 95
<211> LENGTH: 1842
<212> TYPE: DNA
<213> ORGANISM: Artificial Sequence
<220> FEATURE:
<223> OTHER INFORMATION: human optimized

<400> SEQUENCE: 95
atgggattcc gccttctgtg ctgcgtggcc ttctgcttgc ttggagctgg tcccgtcgac      60
tcgggagtga cccagacgcc gaagcacttg attaccgcta ctgggcagcg cgtgactctg     120
cgatgctcac cacggtctgg cgacctctcc gtgtactggt atcagcagag cctgaccag     180 ggactgcagt tcctgatcca gtactacaac ggagaggagc gggctaaggg aaacatactg     240
gagcggttct cggcgcaaca attccccgat ctgcactccg aactgaacct gtcctccctg     300
gaattgggag actccgccct gtacttctgc gcaagcagcg tggtgacggg ggatgaacag     360
ttctttggcc tggaaccag actcaccgtg tcgaggacc tcaagaacgt gttcccaccc     420
gaagtcgcgg tgttcgagcc ctccgaagcg gaaatcagcc atactcagaa agccactctc     480
gtgtgcctgg ccaccggatt ctaccccgac acgtcgagc tctcttggtg ggtgaacggg     540
aaagaggtcc acagcggcgt gagcactgat ccgcagccgc tgaaggaaca accgccttg     600 aacgactcgc ggtactgtct gtcctcccgg ctgagagtgt cggccacctt ctggcaaaac     660
cccaggaacc actttaggtg ccaagtccag ttctacggcc tgagcgaaaa cgatgagtgg     720
acccaggaca gagccaagcc tgtgacccag attgtgtcag ccgaggcttg ggtagagca     780 gactgcggat tcacctccga gtcctaccaa caaggcgtcc tctcggcgac cattctgtac     840
gaaatcctgc ttgggaaggc cactctgtac gccgtgctgg tgtccgccct ggtgctgatg     900
gccatggtca gcggaagga ctcccggggg agagcaaaga ggggatcggg agccaccaat     960
tttagcctgc tgaagcaggc cggcgatgtg aagaaaatc ctggcccat gtcccttagc    1020 tcactgctga agtggtcac tgcgagcctg tggctgggac caggcattgc tcaaaagatc    1080
acccagactc agcctgggat gttcgtgcaa gagaaggaag ccgtgaccct cgactgcact    1140
tacgacacct ccgacccgt ctacgggctg ttctggtaca gcagccgtc ctccggagag    1200 atgatcttcc tcatctacca aggctcctat gatcagcaga acgccaccga aggacgctac    1260
agcctgaact tccagaaggc tcggaagtcg gcgaacctcg tgatcagcgc atcccaactg    1320
```

```
ggggacagcg ccatgtactt ctgtgccatg tcgggcggat acaccggggg attcaagacc    1380
attttcgggg ccggcactag actgttcgtg aaggccaaca tccagaatcc tgatccggcg    1440
gtgtatcagc tgcgcgactc caagtcttcc gataaatccg tgtgtctctt tacagacttc    1500
gactcccaaa ccaacgtgtc acagtccaag gacagcgatg tgtacatcac cgacaaaacc    1560
gtgctggaca tgcggtccat ggacttcaag tcaaacagcg cagtcgcctg gtccaacaag    1620
tccgacttcg cctgtgcgaa cgccttcaac aactccatca ttccggaaga tacctttttc    1680
ccttcacctg agtcgagctg tgatgtgaag ctcgtggaaa agtcgtttga aacggacacc    1740
aacctgaact ttcagaacct gtccgtgatt ggtttccgca tcctgctgct gaaggtcgcc    1800
ggcttcaact tgctgatgac gctccggctg tggtcctcgt aa                       1842
```

<210> SEQ ID NO 96
<211> LENGTH: 613
<212> TYPE: PRT
<213> ORGANISM: Artificial Sequence
<220> FEATURE:
<223> OTHER INFORMATION: human optimized

<400> SEQUENCE: 96

```
Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Gly Gly Asp Gly Asp Glu Gln Phe Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270
```

Val Leu Ser Ala Thr Ile Leu Tyr Glu Ile Leu Gly Lys Ala Thr
    275                 280                 285

Leu Tyr Ala Val Leu Val Ser Ala Leu Val Leu Met Ala Met Val Lys
290                 295                 300

Arg Lys Asp Ser Arg Gly Arg Ala Lys Arg Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ser Leu Ser Ser Leu Leu Lys Val Val Thr Ala Ser Leu Trp Leu
            340                 345                 350

Gly Pro Gly Ile Ala Gln Lys Ile Thr Gln Thr Gln Pro Gly Met Phe
        355                 360                 365

Val Gln Glu Lys Glu Ala Val Thr Leu Asp Cys Thr Tyr Asp Thr Ser
    370                 375                 380

Asp Pro Ser Tyr Gly Leu Phe Trp Tyr Lys Gln Pro Ser Ser Gly Glu
385                 390                 395                 400

Met Ile Phe Leu Ile Tyr Gln Gly Ser Tyr Asp Gln Asn Ala Thr
                405                 410                 415

Glu Gly Arg Tyr Ser Leu Asn Phe Gln Lys Ala Arg Lys Ser Ala Asn
            420                 425                 430

Leu Val Ile Ser Ala Ser Gln Leu Gly Asp Ser Ala Met Tyr Phe Cys
        435                 440                 445

Ala Met Ser Gly Gly Tyr Thr Gly Gly Phe Lys Thr Ile Phe Gly Ala
    450                 455                 460

Gly Thr Arg Leu Phe Val Lys Ala Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495

Phe Thr Asp Phe Asp Ser Gln Thr Asn Val Ser Gln Ser Lys Asp Ser
            500                 505                 510

Asp Val Tyr Ile Thr Asp Lys Thr Val Leu Asp Met Arg Ser Met Asp
        515                 520                 525

Phe Lys Ser Asn Ser Ala Val Ala Trp Ser Asn Lys Ser Asp Phe Ala
    530                 535                 540

Cys Ala Asn Ala Phe Asn Asn Ser Ile Ile Pro Glu Asp Thr Phe Phe
545                 550                 555                 560

Pro Ser Pro Glu Ser Ser Cys Asp Val Lys Leu Val Glu Lys Ser Phe
                565                 570                 575

Glu Thr Asp Thr Asn Leu Asn Phe Gln Asn Leu Ser Val Ile Gly Phe
            580                 585                 590

Arg Ile Leu Leu Leu Lys Val Ala Gly Phe Asn Leu Leu Met Thr Leu
        595                 600                 605

Arg Leu Trp Ser Ser
    610

<210> SEQ ID NO 97
<211> LENGTH: 1830
<212> TYPE: DNA
<213> ORGANISM: Artificial Sequence
<220> FEATURE:
<223> OTHER INFORMATION: human optimized

<400> SEQUENCE: 97
atgggttgtc ggttgctgtg ttgcgtcgtg ttctgccttc ttcaagctgg tcctctcgat      60

```
actgccgtga gccaaacccc taagtacctt gtcacccaaa tgggcaacga caagtccatc    120
aaatgcgaac agaacctcgg acacgacacc atgtactggt acaaacagga ttccaagaag    180
ttcctgaaga ttatgttctc atacaacaac aaggaactga ttatcaacga aactgtgccg    240
aaccggttct caccgaagtc gcctgacaag gctcatctca acttgcatat caactcgctg    300
gagctcggcg actccgccgt gtacttctgc gcgtccagcc agttctggga cggagcgggc    360
gacgaacagt acttcgggcc gggcactcgg ctgaccgtga ccgaagatct gaacaaagtg    420
ttcccccccg aagtggccgt gttcgaacct tccgaggccg agatcagcca cacccaaaag    480
gccactctgg tctgcctggc caccggtttc ttccccgatc acgtgaaact gtcttggtgg    540
gtgaacggaa agaagtgcac tcgggggtgt ccacggaccc ccagcctct gaaggaacag    600
ccggcactga atgactcacg ctactgtctg tcgtcacggc tgcgcgtgtc ggccaccttc    660
tggcaaaacc cgcgaaacca ctttcgctgc caagtgcagt tttacgggct ttccgagaac    720
gacgagtgga ctcaggacag agcgaagccc gtgacccaaa tcgtgtccgc cgaggcctgg    780
ggacgcgccg actgcggttt caccteegtg agctaccaac agggcgtgct gtcagctacc    840
atcctttacg agatcctcct gggaaaggcc accctctacg ccgtcctggt gccgcactg     900
gtgctgatgg ctatggtcaa gcggaaggat tttagggcca acgcgggtc cggagcgacc    960
aacttctcgc tgttgaagca ggccggcgat gtggaagaga ccctggacc gatgacgtcc    1020
attagagccg tgttcatttt cctgtggctg caactggacc tcgtgaatgg agaaaacgtc    1080
gagcagcacc catccaccct gagcgtgcag gagggagact ccgcagtcat caagtgcact    1140
tactccgact cagcatcaaa ctatttcccg tggtataagc aggaactcgg aaagcggcct    1200
cagctcatca ttgacatccg ctccaacgtc ggagagaaga aggaccagag aattgccgtg    1260
acactcaaca gaccgccaa gcatttctcc cttcacatca ccgaaaccca gcccgaggac    1320
agcgccgtct acttttgtgc ggcctcgagg ggcactgggt ttcagaagct cgtgttcggc    1380
actgggaccc ggctgctggt gtcgccaaac atccagaatc cagacccgc ggtgtaccag    1440
ctgagagact cgaagtcttc cgataaatcc gtgtgtctct ttacagactt cgatagccag    1500
actaacgtgt cccagtccaa ggactccgat gtgtacatca ccgacaagac tgtgctggat    1560
atgcggagca tggactttaa gtccaattca gcggtcgcgt ggagcaacaa gtccgacttc    1620
gcctgcgcta acgctttcaa caactccatt atcccggagg ataccttctt cccgtcaccg    1680
gaatcctcgt gcgacgtgaa gctggtcgag aagtccttcg aaaccgatac caacctgaac    1740
ttccaaaaacc tctccgtgat cggcttcaga atcctgctgc tgaaagtggc tggcttcaat    1800
ttgctgatga ccctgcggct ctggagcagc                                     1830
```

<210> SEQ ID NO 98
<211> LENGTH: 610
<212> TYPE: PRT
<213> ORGANISM: Artificial Sequence
<220> FEATURE:
<223> OTHER INFORMATION: human optimized

<400> SEQUENCE: 98

Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

```
Asp Thr Met Tyr Trp Tyr Lys Gln Asp Ser Lys Lys Phe Leu Lys Ile
    50              55                  60

Met Phe Ser Tyr Asn Asn Lys Glu Leu Ile Ile Asn Glu Thr Val Pro
65              70                  75                      80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100             105                 110

Ser Gln Phe Trp Asp Gly Ala Gly Asp Glu Gln Tyr Phe Gly Pro Gly
            115             120                 125

Thr Arg Leu Thr Val Thr Glu Asp Leu Asn Lys Val Phe Pro Pro Glu
130             135                 140

Val Ala Val Phe Glu Pro Ser Glu Ala Glu Ile Ser His Thr Gln Lys
145                 150             155                     160

Ala Thr Leu Val Cys Leu Ala Thr Gly Phe Phe Pro Asp His Val Glu
                165             170                 175

Leu Ser Trp Trp Val Asn Gly Lys Glu Val His Ser Gly Val Ser Thr
            180             185                 190

Asp Pro Gln Pro Leu Lys Glu Gln Pro Ala Leu Asn Asp Ser Arg Tyr
        195             200                 205

Cys Leu Ser Ser Arg Leu Arg Val Ser Ala Thr Phe Trp Gln Asn Pro
        210             215                 220

Arg Asn His Phe Arg Cys Gln Val Gln Phe Tyr Gly Leu Ser Glu Asn
225             230                 235                     240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Val Ser Tyr
            260             265                 270

Gln Gln Gly Val Leu Ser Ala Thr Ile Leu Tyr Glu Ile Leu Leu Gly
        275             280                 285

Lys Ala Thr Leu Tyr Ala Val Leu Val Ser Ala Leu Val Leu Met Ala
290             295                 300

Met Val Lys Arg Lys Asp Phe Arg Ala Lys Arg Gly Ser Gly Ala Thr
305             310                 315                     320

Asn Phe Ser Leu Leu Lys Gln Ala Gly Asp Val Glu Glu Asn Pro Gly
            325                 330                 335

Pro Met Thr Ser Ile Arg Ala Val Phe Ile Phe Leu Trp Leu Gln Leu
            340             345                 350

Asp Leu Val Asn Gly Glu Asn Val Glu Gln His Pro Ser Thr Leu Ser
            355             360                 365

Val Gln Glu Gly Asp Ser Ala Val Ile Lys Cys Thr Tyr Ser Asp Ser
    370             375                 380

Ala Ser Asn Tyr Phe Pro Trp Tyr Lys Gln Glu Leu Gly Lys Arg Pro
385             390                 395                     400

Gln Leu Ile Ile Asp Ile Arg Ser Asn Val Gly Glu Lys Lys Asp Gln
            405                 410                 415

Arg Ile Ala Val Thr Leu Asn Lys Thr Ala Lys His Phe Ser Leu His
            420                 425                 430

Ile Thr Glu Thr Gln Pro Glu Asp Ser Ala Val Tyr Phe Cys Ala Ala
        435                 440                 445

Ser Arg Gly Thr Gly Phe Gln Lys Leu Val Phe Gly Thr Gly Thr Arg
    450                 455                 460

Leu Leu Val Ser Pro Asn Ile Gln Asn Pro Asp Pro Ala Val Tyr Gln
```

```
                465                 470                 475                 480
Leu Arg Asp Ser Lys Ser Ser Asp Lys Ser Val Cys Leu Phe Thr Asp
                    485                 490                 495

Phe Asp Ser Gln Thr Asn Val Ser Gln Ser Lys Asp Ser Asp Val Tyr
                500                 505                 510

Ile Thr Asp Lys Thr Val Leu Asp Met Arg Ser Met Asp Phe Lys Ser
                515                 520                 525

Asn Ser Ala Val Ala Trp Ser Asn Lys Ser Asp Phe Ala Cys Ala Asn
            530                 535                 540

Ala Phe Asn Asn Ser Ile Ile Pro Glu Asp Thr Phe Phe Pro Ser Pro
545                 550                 555                 560

Glu Ser Ser Cys Asp Val Lys Leu Val Glu Lys Ser Phe Glu Thr Asp
                565                 570                 575

Thr Asn Leu Asn Phe Gln Asn Leu Ser Val Ile Gly Phe Arg Ile Leu
            580                 585                 590

Leu Leu Lys Val Ala Gly Phe Asn Leu Leu Met Thr Leu Arg Leu Trp
        595                 600                 605

Ser Ser
    610

<210> SEQ ID NO 99
<211> LENGTH: 828
<212> TYPE: DNA
<213> ORGANISM: Artificial Sequence
<220> FEATURE:
<223> OTHER INFORMATION: TCR-7 a complete

<400> SEQUENCE: 99
atgagcctct cttccctgct caaagtggtc actgcctccc tgtggctggg accgggaatc    60
gcccagaaga tcactcagac ccagcctgga atgttcgtgc aagagaaaga ggccgtgacc   120
ctggattgta cttatgacac ttcagaccag tcgtacggtt tgttctggta caagcagccg   180
tcctccggag aaatgatctt cctgatctac cagggatcgt acgacgagca gaacgctacc   240
gagggcagat attccctcaa cttccaaaag gcccggaaat ccgcgaacct cgtgatctcg   300
gcctcacaac ttgggactc cgctatgtat ttctgcgcaa tgtccggcga tagcgcagga   360
aacatgctga ctttcggcgg tggaactagg ctgatggtca agccccacat tcaaaaccct   420
gacccagcag tctaccagtt gcgggattcc aagtcttccg ataaatccgt gtgtctcttt   480
acagacttcg atagccagac caacgtgtcc cagagcaaag acagcgacgt gtacattact   540
gacaagactg tgctggacat gcggtccatg gacttcaaga gcaactccgc cgtcgcttgg   600
tccaacaagt ctgactttgc gtgcgcgaac gctttcaaca acagcattat cccggaggac   660 accttttttcc cttccagcga cgtcccctgc gatgtcaagc ttgtggaaaa gtcgttcgaa   720
accgacacca acctgaactt ccagaacctg ctagtgattg tgctccgcat tctgctgctg   780
aaggtcgccg gcttcaatct cctgatgact ctccgcttgt ggtcctca                828

<210> SEQ ID NO 100
<211> LENGTH: 936
<212> TYPE: DNA
<213> ORGANISM: Artificial Sequence
<220> FEATURE:
<223> OTHER INFORMATION: TCR-7 b complete

<400> SEQUENCE: 100
atggcgtccc tgctgttctt ctgcggtgcc ttctaccttc tgggaaccgg ctcgatggac    60
```

```
gccgacgtga cccaaacccc tcgcaaccgc atcaccaaga ctggaaagcg gatcatgctg    120
gaatgctccc agaccaaggg ccacgaccgc atgtactggt acagacagga cccgggtctg    180
ggattgcgcc tgatctacta ctccttcgac gtgaaggaca tcaacaaggg ggagatctcc    240
gatggatact cagtctcgag acaagcccag gctaagtttt ccctgtccct cgaatccgcc    300
attcccaatc agaccgcgct gtacttctgt gccacctcgg attgggaccg atccggcgac    360
aaggaaactc agtacttcgg accaggaacc aggctcctgg tgctggagga tctgaacaag    420
gtgttcccgc cggaagtggc agtgttcgag ccatccaagg cggagatcgc ccatacgcag    480
aaggccaccc tcgtgtgcct ggccactggg ttttttcctg accacgtgga gctctcgtgg    540
tgggtcaacg gaaaggaagt gcacagcggt gtctcaaccg acccgcaacc tctcaaggaa    600
cagcccgcgc tcaatgattc gcggtactgc ctgagcagcc ggctcagagt gtccgccact    660
ttctggcaaa acccgcggaa ccatttccgg tgccaagtgc aattctacgg gctgtcggaa    720
aacgacgaat ggacccagga cagggccaag cccgtgaccc agattgtgtc cgctgaagcc    780
tgggggagag ctgattgcgg tatcaccagc gccagctacc accagggcgt gctgtcagcc    840
accattctgt acgaaatcct cctggggaag gccacactgt acgccgtgct cgtgtccgcc    900
ctggtgctga tggccatggt caagcggaag gacttc                              936
```

<210> SEQ ID NO 101
<211> LENGTH: 1833
<212> TYPE: DNA
<213> ORGANISM: Artificial Sequence
<220> FEATURE:
<223> OTHER INFORMATION: TCR-7 polycistronic construct

<400> SEQUENCE: 101

```
atggcgtccc tgctgttctt ctgcggtgcc ttctaccttc tgggaaccgg ctcgatggac     60
gccgacgtga cccaaacccc tcgcaaccgc atcaccaaga ctggaaagcg gatcatgctg    120
gaatgctccc agaccaaggg ccacgaccgc atgtactggt acagacagga cccgggtctg    180
ggattgcgcc tgatctacta ctccttcgac gtgaaggaca tcaacaaggg ggagatctcc    240
gatggatact cagtctcgag acaagcccag gctaagtttt ccctgtccct cgaatccgcc    300
attcccaatc agaccgcgct gtacttctgt gccacctcgg attgggaccg atccggcgac    360
aaggaaactc agtacttcgg accaggaacc aggctcctgg tgctggagga tctgaacaag    420
gtgttcccgc cggaagtggc agtgttcgag ccatccaagg cggagatcgc ccatacgcag    480
aaggccaccc tcgtgtgcct ggccactggg ttttttcctg accacgtgga gctctcgtgg    540
tgggtcaacg gaaaggaagt gcacagcggt gtctcaaccg acccgcaacc tctcaaggaa    600
cagcccgcgc tcaatgattc gcggtactgc ctgagcagcc ggctcagagt gtccgccact    660
ttctggcaaa acccgcggaa ccatttccgg tgccaagtgc aattctacgg gctgtcggaa    720
aacgacgaat ggacccagga cagggccaag cccgtgaccc agattgtgtc cgctgaagcc    780
tgggggagag ctgattgcgg tatcaccagc gccagctacc accagggcgt gctgtcagcc    840
accattctgt acgaaatcct cctggggaag gccacactgt acgccgtgct cgtgtccgcc    900
ctggtgctga tggccatggt caagcggaag gacttcggca cggagctac caacttctcc    960 ctgctgaagc aggccggcga tgtggaagaa atccccggac ctatgagcct ctcttccctg   1020
ctcaaagtgg tcactgcctc cctgtggctg ggaccgggaa tcgcccagaa gatcactcag   1080
acccagcctg aatgttcgt gcaagagaaa gaggccgtga ccctggattg tacttatgac    1140
acttcagacc agtcgtacgg tttgttctgg tacaagcagc cgtcctccgg agaaatgatc    1200
```

| | |
|---|---|
| ttcctgatct accagggatc gtacgacgag cagaacgcta ccgagggcag atattccctc | 1260 |
| aacttccaaa aggcccggaa atccgcgaac ctcgtgatct cggcctcaca acttggggac | 1320 |
| tccgctatgt atttctgcgc aatgtccggc gatagcgcag gaaacatgct gactttcggc | 1380 |
| ggtggaacta ggctgatggt caagccccac attcaaaacc ctgacccagc agtctaccag | 1440 |
| ttgcgggatt ccaagtcttc cgataaatcc gtgtgtctct ttacagactt cgatagccag | 1500 |
| accaacgtgt cccagagcaa agacagcgac gtgtacatta ctgacaagac tgtgctggac | 1560 |
| atgcggtcca tggacttcaa gagcaactcc gccgtcgctt ggtccaacaa gtctgacttt | 1620 |
| gcgtgcgcga acgctttcaa caacagcatt atcccggagg acacctttt cccttccagc | 1680 |
| gacgtcccct gcgatgtcaa gcttgtggaa aagtcgttcg aaaccgacac caacctgaac | 1740 |
| ttccagaacc tgctagtgat tgtgctccgc attctgctgc tgaaggtcgc cggcttcaat | 1800 |
| ctcctgatga ctctccgctt gtggtcctca taa | 1833 |

<210> SEQ ID NO 102
<211> LENGTH: 276
<212> TYPE: PRT
<213> ORGANISM: Artificial Sequence
<220> FEATURE:
<223> OTHER INFORMATION: TCR-7 a complete

<400> SEQUENCE: 102

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Ser Gly Asp Ser Ala Gly Asn Met Leu Thr Phe Gly Gly Gly
        115                 120                 125

Thr Arg Leu Met Val Lys Pro His Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Ser Asp Val Pro Cys Asp Val Lys Leu Val Glu Lys Ser Phe Glu
225                 230                 235                 240

Thr Asp Thr Asn Leu Asn Phe Gln Asn Leu Leu Val Ile Val Leu Arg
```

```
                        245                 250                 255
Ile Leu Leu Leu Lys Val Ala Gly Phe Asn Leu Leu Met Thr Leu Arg
            260                 265                 270

Leu Trp Ser Ser
            275

<210> SEQ ID NO 103
<211> LENGTH: 312
<212> TYPE: PRT
<213> ORGANISM: Artificial Sequence
<220> FEATURE:
<223> OTHER INFORMATION: TCR-7 b complete

<400> SEQUENCE: 103

Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
            100                 105                 110

Ser Asp Trp Asp Arg Ser Gly Asp Lys Glu Thr Gln Tyr Phe Gly Pro
        115                 120                 125

Gly Thr Arg Leu Leu Val Leu Glu Asp Leu Asn Lys Val Phe Pro Pro
130                 135                 140

Glu Val Ala Val Phe Glu Pro Ser Lys Ala Glu Ile Ala His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Ile Thr Ser Ala Ser
            260                 265                 270

Tyr His Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
290                 295                 300

Ala Met Val Lys Arg Lys Asp Phe
305                 310
```

-continued

```
<210> SEQ ID NO 104
<211> LENGTH: 610
<212> TYPE: PRT
<213> ORGANISM: Artificial Sequence
<220> FEATURE:
<223> OTHER INFORMATION: TCR-7 polyprotein

<400> SEQUENCE: 104

Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
    50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
            100                 105                 110

Ser Asp Trp Asp Arg Ser Gly Asp Lys Glu Thr Gln Tyr Phe Gly Pro
        115                 120                 125

Gly Thr Arg Leu Leu Val Leu Glu Asp Leu Asn Lys Val Phe Pro Pro
    130                 135                 140

Glu Val Ala Val Phe Glu Pro Ser Lys Ala Glu Ile Ala His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Ile Thr Ser Ala Ser
            260                 265                 270

Tyr His Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Phe Gly Ser Gly Ala Thr Asn Phe Ser
305                 310                 315                 320

Leu Leu Lys Gln Ala Gly Asp Val Glu Glu Asn Pro Gly Pro Met Ser
                325                 330                 335

Leu Ser Ser Leu Leu Lys Val Val Thr Ala Ser Leu Trp Leu Gly Pro
            340                 345                 350

Gly Ile Ala Gln Lys Ile Thr Gln Thr Gln Pro Gly Met Phe Val Gln
        355                 360                 365

Glu Lys Glu Ala Val Thr Leu Asp Cys Thr Tyr Asp Thr Ser Asp Gln
```

```
                370                 375                 380
Ser Tyr Gly Leu Phe Trp Tyr Lys Gln Pro Ser Ser Gly Glu Met Ile
385                 390                 395                 400

Phe Leu Ile Tyr Gln Gly Ser Tyr Asp Glu Gln Asn Ala Thr Glu Gly
                405                 410                 415

Arg Tyr Ser Leu Asn Phe Gln Lys Ala Arg Lys Ser Ala Asn Leu Val
                420                 425                 430

Ile Ser Ala Ser Gln Leu Gly Asp Ser Ala Met Tyr Phe Cys Ala Met
            435                 440                 445

Ser Gly Asp Ser Ala Gly Asn Met Leu Thr Phe Gly Gly Gly Thr Arg
            450                 455                 460

Leu Met Val Lys Pro His Ile Gln Asn Pro Asp Pro Ala Val Tyr Gln
465                 470                 475                 480

Leu Arg Asp Ser Lys Ser Ser Asp Lys Ser Val Cys Leu Phe Thr Asp
                485                 490                 495

Phe Asp Ser Gln Thr Asn Val Ser Gln Ser Lys Asp Ser Asp Val Tyr
                500                 505                 510

Ile Thr Asp Lys Thr Val Leu Asp Met Arg Ser Met Asp Phe Lys Ser
            515                 520                 525

Asn Ser Ala Val Ala Trp Ser Asn Lys Ser Asp Phe Ala Cys Ala Asn
            530                 535                 540

Ala Phe Asn Asn Ser Ile Ile Pro Glu Asp Thr Phe Phe Pro Ser Ser
545                 550                 555                 560

Asp Val Pro Cys Asp Val Lys Leu Val Glu Lys Ser Phe Glu Thr Asp
                565                 570                 575

Thr Asn Leu Asn Phe Gln Asn Leu Leu Val Ile Val Leu Arg Ile Leu
                580                 585                 590

Leu Leu Lys Val Ala Gly Phe Asn Leu Leu Met Thr Leu Arg Leu Trp
            595                 600                 605

Ser Ser
    610

<210> SEQ ID NO 105
<211> LENGTH: 831
<212> TYPE: DNA
<213> ORGANISM: Artificial Sequence
<220> FEATURE:
<223> OTHER INFORMATION: TCR-8 a complete

<400> SEQUENCE: 105
atgtccctta gctcactgct gaaagtggtc actgcgagcc tgtggctggg accaggcatt      60
gctcaaaaga tcacccagac tcagcctggg atgttcgtgc aagagaagga agccgtgacc     120
ctcgactgca cttacgacac ctccgacccg tcctacgggc tgttctggta caagcagccg     180
tcctccggag agatgatctt cctcatctac caaggctcct atgatcagca gaacgccacc     240
gaaggacgct acagcctgaa cttccagaag gctcggaagt cggcgaacct cgtgatcagc     300
gcatcccaac tggggacag cgccatgtac ttctgtgcca tgtcgggcgg atacaccggg     360
ggattcaaga ccattttcgg ggccggcact agactgttcg tgaaggccaa catccagaat     420
cctgatccgg cggtgtatca gctgcgcgac tccaagtctt ccgataaatc cgtgtgtctc     480
tttacagact cgactcccca aaccaacgtg tcacagtcca aggacagcga tgtgtacatc     540
accgacaaaa ccgtgctgga catgcggtcc atgactttca gtcaaacag cgcagtcgcc     600 tggtccaaca gtccgacttt cgcctgtgcg aacgccttca caactccat cattccggaa     660
```

| | |
|---|---|
| gataccttttt tcccttcaag cgacgtcccc tgtgatgtga agctcgtgga aaagtcgttt | 720 |
| gaaacggaca ccaacctgaa ctttcagaac ctgctagtga ttgtgctccg catcctgctg | 780 |
| ctgaaggtcg ccggcttcaa cttgctgatg acgctccggc tgtggtcctc g | 831 |

<210> SEQ ID NO 106
<211> LENGTH: 930
<212> TYPE: DNA
<213> ORGANISM: Artificial Sequence
<220> FEATURE:
<223> OTHER INFORMATION: TCR-8 b complete

<400> SEQUENCE: 106

| | |
|---|---|
| atgggattcc gccttctgtg ctgcgtggcc ttctgcttgc ttggagctgg tcccgtcgac | 60 |
| tcgggagtga cccagacgcc gaagcacttg attaccgcta ctgggcagcg cgtgactctg | 120 |
| cgatgctcac cacggtctgg cgacctctcc gtgtactggt atcagcagag cctggaccag | 180 |
| ggactgcagt tcctgatcca gtactacaac ggagaggagc gggctaaggg aaacatactg | 240 |
| gagcggttct cggcgcaaca attccccgat ctgcactccg aactgaacct gtcctccctg | 300 |
| gaattgggag actccgccct gtacttctgc gcaagcagcg tggtgacgg ggatgaacag | 360 |
| ttctttggcc ctggaaccag actcaccgtg ctcgaggacc tcaagaacgt gttcccaccc | 420 |
| gaagtcgcgg tgttcgagcc ctccaaggcg gagatcgccc atactcagaa agccactctc | 480 |
| gtgtgcctgg ccaccggatt ctacccgac cacgtcgagc tctcttggtg ggtgaacggg | 540 |
| aaagaggtcc acagcggcgt gagcactgat ccgcagccgc tgaaggaaca acccgccttg | 600 |
| aacgactcgc ggtactgtct gtcctcccgg ctgagagtgt cggccacctt ctggcaaaac | 660 |
| cccaggaacc actttaggtg ccaagtccag ttctacggcc tgagcgaaaa cgatgagtgg | 720 |
| acccaggaca gagccaagcc tgtgacccag attgtgtcag ccgaggcttg gggtagagca | 780 |
| gactgcggaa tcaccagcgc cagctaccac caaggcgtcc tctcggcgac cattctgtac | 840 |
| gaaatcctgc ttgggaaggc cactctgtac gccgtgctgg tgtccgccct ggtgctgatg | 900 |
| gccatggtca agcggaagga ctcccggggg | 930 |

<210> SEQ ID NO 107
<211> LENGTH: 1842
<212> TYPE: DNA
<213> ORGANISM: Artificial Sequence
<220> FEATURE:
<223> OTHER INFORMATION: TCR-8 polycistronic construct

<400> SEQUENCE: 107

| | |
|---|---|
| atgggattcc gccttctgtg ctgcgtggcc ttctgcttgc ttggagctgg tcccgtcgac | 60 |
| tcgggagtga cccagacgcc gaagcacttg attaccgcta ctgggcagcg cgtgactctg | 120 |
| cgatgctcac cacggtctgg cgacctctcc gtgtactggt atcagcagag cctggaccag | 180 |
| ggactgcagt tcctgatcca gtactacaac ggagaggagc gggctaaggg aaacatactg | 240 |
| gagcggttct cggcgcaaca attccccgat ctgcactccg aactgaacct gtcctccctg | 300 |
| gaattgggag actccgccct gtacttctgc gcaagcagcg tggtgacgg ggatgaacag | 360 |
| ttctttggcc ctggaaccag actcaccgtg ctcgaggacc tcaagaacgt gttcccaccc | 420 |
| gaagtcgcgg tgttcgagcc ctccaaggcg gagatcgccc atactcagaa agccactctc | 480 |
| gtgtgcctgg ccaccggatt ctacccgac cacgtcgagc tctcttggtg ggtgaacggg | 540 |
| aaagaggtcc acagcggcgt gagcactgat ccgcagccgc tgaaggaaca acccgccttg | 600 |
| aacgactcgc ggtactgtct gtcctcccgg ctgagagtgt cggccacctt ctggcaaaac | 660 |

-continued

```
cccaggaacc actttaggtg ccaagtccag ttctacggcc tgagcgaaaa cgatgagtgg    720
acccaggaca gagccaagcc tgtgacccag attgtgtcag ccgaggcttg gggtagagca    780
gactgcggaa tcaccagcgc cagctaccac caaggcgtcc tctcggcgac cattctgtac    840
gaaatcctgc ttgggaaggc cactctgtac gccgtgctgg tgtccgccct ggtgctgatg    900
gccatggtca gcggaagga ctcccggggg agagcaaaga ggggatcggg agccaccaat     960
tttagcctgc tgaagcaggc cggcgatgtg aagaaaatc ctggcccat gtcccttagc     1020
tcactgctga aagtggtcac tgcgagcctg tggctgggac caggcattgc tcaaaagatc   1080
acccagactc agcctgggat gttcgtgcaa gagaaggaag ccgtgaccct cgactgcact   1140
tacgacacct ccgacccgtc ctacgggctg ttctggtaca agcagccgtc ctccggagag   1200
atgatcttcc tcatctacca aggctcctat gatcagcaga acgccaccga aggacgctac   1260
agcctgaact tccagaaggc tcggaagtcg gcgaacctcg tgatcagcgc atcccaactg   1320
ggggacagcg ccatgtactt ctgtgccatg tcgggcggat acaccggggg attcaagacc   1380
atttttcgggg ccggcactag actgttcgtg aaggccaaca tccagaatcc tgatccggcg   1440
gtgtatcagc tgcgcgactc caagtcttcc gataaatccg tgtgtctctt tacagacttc   1500
gactcccaaa ccaacgtgtc acagtccaag gacagcgatg tgtacatcac cgacaaaacc   1560
gtgctggaca tgcggtccat ggacttcaag tcaaacagcg cagtcgcctg gtccaacaag   1620
tccgacttcg cctgtgcgaa cgccttcaac aactccatca ttccggaaga tacctttttc   1680
ccttcaagcg acgtcccctg tgatgtgaag ctcgtggaaa agtcgtttga acggacaccc   1740
aacctgaact ttcagaacct gctagtgatt gtgctccgca tcctgctgct gaaggtcgcc   1800
ggcttcaact tgctgatgac gctccggctg tggtcctcgt aa                       1842
```

<210> SEQ ID NO 108
<211> LENGTH: 277
<212> TYPE: PRT
<213> ORGANISM: Artificial Sequence
<220> FEATURE:
<223> OTHER INFORMATION: TCR-8 a complete

<400> SEQUENCE: 108

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Ser Gly Gly Tyr Thr Gly Gly Phe Lys Thr Ile Phe Gly Ala
        115                 120                 125

Gly Thr Arg Leu Phe Val Lys Ala Asn Ile Gln Asn Pro Asp Pro Ala
    130                 135                 140

Val Tyr Gln Leu Arg Asp Ser Lys Ser Ser Asp Lys Ser Val Cys Leu
```

```
                145                 150                 155                 160
            Phe Thr Asp Phe Asp Ser Gln Thr Asn Val Ser Gln Ser Lys Asp Ser
                            165                 170                 175

Asp Val Tyr Ile Thr Asp Lys Thr Val Leu Asp Met Arg Ser Met Asp
                            180                 185                 190

Phe Lys Ser Asn Ser Ala Val Ala Trp Ser Asn Lys Ser Asp Phe Ala
                            195                 200                 205

Cys Ala Asn Ala Phe Asn Asn Ser Ile Ile Pro Glu Asp Thr Phe Phe
                            210                 215                 220

Pro Ser Ser Asp Val Pro Cys Asp Val Lys Leu Val Glu Lys Ser Phe
            225                 230                 235                 240

Glu Thr Asp Thr Asn Leu Asn Phe Gln Asn Leu Leu Val Ile Val Leu
                            245                 250                 255

Arg Ile Leu Leu Leu Lys Val Ala Gly Phe Asn Leu Leu Met Thr Leu
                            260                 265                 270

Arg Leu Trp Ser Ser
                            275

<210> SEQ ID NO 109
<211> LENGTH: 310
<212> TYPE: PRT
<213> ORGANISM: Artificial Sequence
<220> FEATURE:
<223> OTHER INFORMATION: TCR-8 b complete

<400> SEQUENCE: 109

Met Gly Phe Arg Leu Leu Cys Cys Val Ala Phe Cys Leu Leu Gly Ala
            1               5                   10                  15

Gly Pro Val Asp Ser Gly Val Thr Gln Thr Pro Lys His Leu Ile Thr
                            20                  25                  30

Ala Thr Gly Gln Arg Val Thr Leu Arg Cys Ser Pro Arg Ser Gly Asp
                            35                  40                  45

Leu Ser Val Tyr Trp Tyr Gln Gln Ser Leu Asp Gln Gly Leu Gln Phe
                50                  55                  60

Leu Ile Gln Tyr Tyr Asn Gly Glu Glu Arg Ala Lys Gly Asn Ile Leu
            65                  70                  75                  80

Glu Arg Phe Ser Ala Gln Gln Phe Pro Asp Leu His Ser Glu Leu Asn
                            85                  90                  95

Leu Ser Ser Leu Glu Leu Gly Asp Ser Ala Leu Tyr Phe Cys Ala Ser
                            100                 105                 110

Ser Gly Gly Asp Gly Asp Glu Gln Phe Phe Gly Pro Gly Thr Arg Leu
                            115                 120                 125

Thr Val Leu Glu Asp Leu Lys Asn Val Phe Pro Pro Glu Val Ala Val
                            130                 135                 140

Phe Glu Pro Ser Lys Ala Glu Ile Ala His Thr Gln Lys Ala Thr Leu
            145                 150                 155                 160

Val Cys Leu Ala Thr Gly Phe Tyr Pro Asp His Val Glu Leu Ser Trp
                            165                 170                 175

Trp Val Asn Gly Lys Glu Val His Ser Gly Val Ser Thr Asp Pro Gln
                            180                 185                 190

Pro Leu Lys Glu Gln Pro Ala Leu Asn Asp Ser Arg Tyr Cys Leu Ser
                            195                 200                 205

Ser Arg Leu Arg Val Ser Ala Thr Phe Trp Gln Asn Pro Arg Asn His
                            210                 215                 220

Phe Arg Cys Gln Val Gln Phe Tyr Gly Leu Ser Glu Asn Asp Glu Trp
```

```
225                 230                 235                 240
Thr Gln Asp Arg Ala Lys Pro Val Thr Gln Ile Val Ser Ala Glu Ala
                245                 250                 255

Trp Gly Arg Ala Asp Cys Gly Ile Thr Ser Ala Ser Tyr His Gln Gly
                260                 265                 270

Val Leu Ser Ala Thr Ile Leu Tyr Glu Ile Leu Leu Gly Lys Ala Thr
                275                 280                 285

Leu Tyr Ala Val Leu Val Ser Ala Leu Val Leu Met Ala Met Val Lys
                290                 295                 300

Arg Lys Asp Ser Arg Gly
305                 310

<210> SEQ ID NO 110
<211> LENGTH: 613
<212> TYPE: PRT
<213> ORGANISM: Artificial Sequence
<220> FEATURE:
<223> OTHER INFORMATION: TCR-8 polyprotein

<400> SEQUENCE: 110

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
                20                  25                  30

Ala Thr Gly Gln Arg Val Thr Leu Arg Cys Ser Pro Arg Ser Gly Asp
                35                  40                  45

Leu Ser Val Tyr Trp Tyr Gln Gln Ser Leu Asp Gln Gly Leu Gln Phe
                50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
                100                 105                 110

Ser Gly Gly Asp Gly Asp Glu Gln Phe Phe Gly Pro Gly Thr Arg Leu
                115                 120                 125

Thr Val Leu Glu Asp Leu Lys Asn Val Phe Pro Pro Glu Val Ala Val
                130                 135                 140

Phe Glu Pro Ser Lys Ala Glu Ile Ala His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
                195                 200                 205

Ser Arg Leu Arg Val Ser Ala Thr Phe Trp Gln Asn Pro Arg Asn His
                210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Ile Thr Ser Ala Ser Tyr His Gln Gly
                260                 265                 270

Val Leu Ser Ala Thr Ile Leu Tyr Glu Ile Leu Leu Gly Lys Ala Thr
```

275                 280                 285
Leu Tyr Ala Val Leu Val Ser Ala Leu Val Leu Met Ala Met Val Lys
        290                 295                 300

Arg Lys Asp Ser Arg Gly Arg Ala Lys Arg Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ser Leu Ser Ser Leu Leu Lys Val Val Thr Ala Ser Leu Trp Leu
                340                 345                 350

Gly Pro Gly Ile Ala Gln Lys Ile Thr Gln Thr Gln Pro Gly Met Phe
                355                 360                 365

Val Gln Glu Lys Glu Ala Val Thr Leu Asp Cys Thr Tyr Asp Thr Ser
        370                 375                 380

Asp Pro Ser Tyr Gly Leu Phe Trp Tyr Lys Gln Pro Ser Ser Gly Glu
385                 390                 395                 400

Met Ile Phe Leu Ile Tyr Gln Gly Ser Tyr Asp Gln Gln Asn Ala Thr
                405                 410                 415

Glu Gly Arg Tyr Ser Leu Asn Phe Gln Lys Ala Arg Lys Ser Ala Asn
                420                 425                 430

Leu Val Ile Ser Ala Ser Gln Leu Gly Asp Ser Ala Met Tyr Phe Cys
                435                 440                 445

Ala Met Ser Gly Gly Tyr Thr Gly Gly Phe Lys Thr Ile Phe Gly Ala
        450                 455                 460

Gly Thr Arg Leu Phe Val Lys Ala Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495

Phe Thr Asp Phe Asp Ser Gln Thr Asn Val Ser Gln Ser Lys Asp Ser
                500                 505                 510

Asp Val Tyr Ile Thr Asp Lys Thr Val Leu Asp Met Arg Ser Met Asp
                515                 520                 525

Phe Lys Ser Asn Ser Ala Val Ala Trp Ser Asn Lys Ser Asp Phe Ala
        530                 535                 540

Cys Ala Asn Ala Phe Asn Asn Ser Ile Ile Pro Glu Asp Thr Phe Phe
545                 550                 555                 560

Pro Ser Ser Asp Val Pro Cys Asp Val Lys Leu Val Glu Lys Ser Phe
                565                 570                 575

Glu Thr Asp Thr Asn Leu Asn Phe Gln Asn Leu Leu Val Ile Val Leu
                580                 585                 590

Arg Ile Leu Leu Leu Lys Val Ala Gly Phe Asn Leu Leu Met Thr Leu
                595                 600                 605

Arg Leu Trp Ser Ser
        610

<210> SEQ ID NO 111
<211> LENGTH: 819
<212> TYPE: DNA
<213> ORGANISM: Artificial Sequence
<220> FEATURE:
<223> OTHER INFORMATION: TCR-9 a complete

<400> SEQUENCE: 111
atgacgtcca ttagagccgt gttcattttc ctgtggctgc aactggacct cgtgaatgga    60
gaaaacgtcg agcagcaccc atccaccctg agcgtgcagg agggagactc cgcagtcatc   120

```
aagtgcactt actccgactc agcatcaaac tatttcccgt ggtataagca ggaactcgga    180
aagcggcctc agctcatcat tgacatccgc tccaacgtcg agagaagaa  ggaccagaga    240
attgccgtga cactcaacaa gaccgccaag catttctccc ttcacatcac cgaaacccag    300
cccgaggaca cgccgtcta  cttttgtgcg gcctcgaggg gcactgggtt tcagaagctc    360
gtgttcggca ctgggacccg gctgctggtg tcgccaaaca tccagaatcc agaccccgcg    420
gtgtaccagc tgagagactc gaagtcttcc gataaatccg tgtgtctctt tacagacttc    480
gatagccaga ctaacgtgtc ccagtccaag gactccgatg tgtacatcac cgacaagact    540
gtgctggata tgcggagcat ggactttaag tccaattcag cggtcgcgtg gagcaacaag    600
tccgacttcg cctgcgctaa cgctttcaac aactccatta tcccggagga taccttcttc    660
ccgtcaagcg acgtcccctg cgacgtgaag ctggtcgaga agtccttcga aaccgatacc    720
aacctgaact tccaaaacct cctagtgatt gtgctcagaa tcctgctgct gaaagtggct    780
ggcttcaatt tgctgatgac cctgcggctc tggagcagc                          819

<210> SEQ ID NO 112
<211> LENGTH: 930
<212> TYPE: DNA
<213> ORGANISM: Artificial Sequence
<220> FEATURE:
<223> OTHER INFORMATION: TCR-9 b complete

<400> SEQUENCE: 112
atgggttgtc ggttgctgtg ttgcgtcgtg ttctgccttc ttcaagctgg tcctctcgat    60
actgccgtga gccaaacccc taagtaccTt gtcacccaaa tgggcaacga caagtccatc    120
aaatgcgaac agaacctcgg acacgacacc atgtactggt acaaacagga ttccaagaag    180
ttcctgaaga ttatgttctc atacaacaac aaggaactga ttatcaacga aactgtgccg    240
aaccggttct caccgaagtc gcctgacaag gctcatctca acttgcatat caactcgctg    300
gagctcggcg actccgccgt gtacttctgc gcgtccagcc agttctggga cggagcgggc    360
gacgaacagt acttcggccc gggcactcgg ctgaccgtga ccgaagatct gaacaaagtg    420
ttcccccccg aagtggccgt gttcgaacct tccaaggcgg agatcgccca cacccaaaag    480
gccactctgg tctgcctggc caccggtttc ttccccgatc acgtggaact gtcttggtgg    540
gtgaacggaa agaagtgca  ctcgggggtg tccacggacc cccagcctct gaaggaacag    600
ccggcactga atgactcacg ctactgtctg tcgtcacggc tgcgcgtgtc ggccaccttc    660
tggcaaaacc cgcgaaacca ctttcgctgc caagtcagtt tttacgggct ttccgagaac    720
gacgagtgga ctcaggacag agcgaagccc gtgacccaaa tcgtgtccgc cgaggcctgg    780
ggacgcgccg actgcggtat caccagcgcc agctaccacc agggcgtgct gtcagctacc    840
atcctttacg agatcctcct gggaaaggcc accctctacg ccgtcctggt gtccgcactg    900
gtgctgatgg ctatggtcaa gcggaaggat                                    930

<210> SEQ ID NO 113
<211> LENGTH: 1833
<212> TYPE: DNA
<213> ORGANISM: Artificial Sequence
<220> FEATURE:
<223> OTHER INFORMATION: TCR-9 polycistronic construct

<400> SEQUENCE: 113
atgggttgtc ggttgctgtg ttgcgtcgtg ttctgccttc ttcaagctgg tcctctcgat    60
actgccgtga gccaaacccc taagtaccTt gtcacccaaa tgggcaacga caagtccatc    120
```

```
aaatgcgaac agaacctcgg acacgacacc atgtactggt acaaacagga ttccaagaag    180
ttcctgaaga ttatgttctc atacaacaac aaggaactga ttatcaacga aactgtgccg    240
aaccggttct caccgaagtc gcctgacaag gctcatctca acttgcatat caactcgctg    300
gagctcggcg actccgccgt gtacttctgc cgtccagcc agttctggga cggagcgggc     360
gacgaacagt acttcggccc gggcactcgg ctgaccgtga ccgaagatct gaacaaagtg    420
ttcccccccg aagtggccgt gttcgaacct tccaaggcgg agatcgccca cacccaaaag    480
gccactctgg tctgcctggc accggtttc ttccccgatc acgtggaact gtcttggtgg     540
gtgaacggaa agaagtgca ctcggggtg tccacgacc cccagcctct aaggaacag        600
ccggcactga atgactcacg ctactgtctg tcgtcacggc tgcgcgtgtc ggccaccttc    660
tggcaaaacc cgcgaaacca ctttcgctgc caagtgcagt tttacgggct ttccgagaac    720
gacgagtgga ctcaggacag agcgaagccc gtgacccaaa tcgtgtccgc cgaggcctgg    780
ggacgcgccg actgcggtat caccagcgcc agctaccacc agggcgtgct gtcagctacc    840
atcctttacg agatcctcct gggaaaggcc accctctacg ccgtcctggt gtccgcactg    900
gtgctgatgg ctatggtcaa gcggaaggat tttagggcca aacgcgggtc cggagcgacc    960
aacttctcgc tgttgaagca ggccggcgat gtggaagaga ccctggaccc gatgacgtcc   1020
attagagccg tgttcatttt cctgtggctg caactggacc tcgtgaatgg agaaaacgtc   1080
gagcagcacc catccaccct gagcgtgcag gagggagact ccgcagtcat caagtgcact   1140
tactccgact cagcatcaaa ctatttcccg tggtataagc aggaactcgg aaagcggcct   1200
cagctcatca ttgacatccg ctccaacgtc ggagagaaga aggaccagag aattgccgtg   1260
acactcaaca agaccgccaa gcatttctcc cttcacatca ccgaaacccca gcccgaggac   1320
agcgccgtct acttttgtgc ggcctcgagg ggcactgggt ttcagaagct cgtgttcggc   1380
actgggaccc ggctgctggt gtcgccaaac atccagaatc cagacccgc ggtgtaccag    1440
ctgagagact cgaagtcttc cgataaatcc gtgtgtctct ttacagactt cgatagccag   1500
actaacgtgt cccagtccaa ggactccgat gtgtacatca ccgacaagac tgtgctggat   1560
atgcggagca tggactttaa gtccaattca gcggtcgcgt ggagcaacaa gtccgacttc   1620
gcctgcgcta acgctttcaa caactccatt atcccggagg atacctctt cccgtcaagc   1680
gacgtccct gcgacgtgaa gctggtcgag aagtccttcg aaaccgatac caacctgaac   1740
ttccaaaacc tcctagtgat tgtgctcaga atcctgctgc tgaaagtggc tggcttcaat   1800
ttgctgatga ccctgcggct ctggagcagc taa                                1833
```

<210> SEQ ID NO 114
<211> LENGTH: 273
<212> TYPE: PRT
<213> ORGANISM: Artificial Sequence
<220> FEATURE:
<223> OTHER INFORMATION: TCR-9 a complete

<400> SEQUENCE: 114

```
Met Thr Ser Ile Arg Ala Val Phe Ile Phe Leu Trp Leu Gln Leu Asp
1               5                  10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
```

```
            50                  55                  60
Leu Ile Ile Asp Ile Arg Ser Asn Val Gly Glu Lys Lys Asp Gln Arg
 65                  70                  75                  80

Ile Ala Val Thr Leu Asn Lys Thr Ala Lys His Phe Ser Leu His Ile
                 85                  90                  95

Thr Glu Thr Gln Pro Glu Asp Ser Ala Val Tyr Phe Cys Ala Ala Ser
                100                 105                 110

Arg Gly Thr Gly Phe Gln Lys Leu Val Phe Gly Thr Gly Thr Arg Leu
                115                 120                 125

Leu Val Ser Pro Asn Ile Gln Asn Pro Asp Pro Ala Val Tyr Gln Leu
            130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
                180                 185                 190

Ser Ala Val Ala Trp Ser Asn Lys Ser Asp Phe Ala Cys Ala Asn Ala
                195                 200                 205

Phe Asn Asn Ser Ile Ile Pro Glu Asp Thr Phe Phe Pro Ser Ser Asp
            210                 215                 220

Val Pro Cys Asp Val Lys Leu Val Glu Lys Ser Phe Glu Thr Asp Thr
225                 230                 235                 240

Asn Leu Asn Phe Gln Asn Leu Leu Val Ile Val Leu Arg Ile Leu Leu
                245                 250                 255

Leu Lys Val Ala Gly Phe Asn Leu Leu Met Thr Leu Arg Leu Trp Ser
                260                 265                 270

Ser

<210> SEQ ID NO 115
<211> LENGTH: 310
<212> TYPE: PRT
<213> ORGANISM: Artificial Sequence
<220> FEATURE:
<223> OTHER INFORMATION: TCR-9 b complete

<400> SEQUENCE: 115

Met Gly Cys Arg Leu Leu Cys Cys Val Val Phe Cys Leu Leu Gln Ala
  1               5                  10                  15

Gly Pro Leu Asp Thr Ala Val Ser Gln Thr Pro Lys Tyr Leu Val Thr
                 20                  25                  30

Gln Met Gly Asn Asp Lys Ser Ile Lys Cys Glu Gln Asn Leu Gly His
                 35                  40                  45

Asp Thr Met Tyr Trp Tyr Lys Gln Asp Ser Lys Lys Phe Leu Lys Ile
             50                  55                  60

Met Phe Ser Tyr Asn Asn Lys Glu Leu Ile Ile Asn Glu Thr Val Pro
 65                  70                  75                  80

Asn Arg Phe Ser Pro Lys Ser Pro Asp Lys Ala His Leu Asn Leu His
                 85                  90                  95

Ile Asn Ser Leu Glu Leu Gly Asp Ser Ala Val Tyr Phe Cys Ala Ser
                100                 105                 110

Ser Gln Phe Trp Asp Gly Ala Gly Asp Glu Gln Tyr Phe Gly Pro Gly
            115                 120                 125

Thr Arg Leu Thr Val Thr Glu Asp Leu Asn Lys Val Phe Pro Pro Glu
            130                 135                 140
```

```
Val Ala Val Phe Glu Pro Ser Lys Ala Glu Ile Ala His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Ile Thr Ser Ala Ser Tyr
            260                 265                 270

His Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp
305                 310

<210> SEQ ID NO 116
<211> LENGTH: 610
<212> TYPE: PRT
<213> ORGANISM: Artificial Sequence
<220> FEATURE:
<223> OTHER INFORMATION: TCR-9 polyprotein

<400> SEQUENCE: 116

Met Gly Cys Arg Leu Leu Cys Cys Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Gln Phe Trp Asp Gly Ala Gly Asp Glu Gln Tyr Phe Gly Pro Gly
        115                 120                 125

Thr Arg Leu Thr Val Thr Glu Asp Leu Asn Lys Val Phe Pro Pro Glu
    130                 135                 140

Val Ala Val Phe Glu Pro Ser Lys Ala Glu Ile Ala His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190
```

```
Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Ile Thr Ser Ala Ser Tyr
            260                 265                 270

His Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Phe Arg Ala Lys Arg Gly Ser Gly Ala Thr
305                 310                 315                 320

Asn Phe Ser Leu Leu Lys Gln Ala Gly Asp Val Glu Glu Asn Pro Gly
                325                 330                 335

Pro Met Thr Ser Ile Arg Ala Val Phe Ile Phe Leu Trp Leu Gln Leu
            340                 345                 350

Asp Leu Val Asn Gly Glu Asn Val Glu Gln His Pro Ser Thr Leu Ser
        355                 360                 365

Val Gln Glu Gly Asp Ser Ala Val Ile Lys Cys Thr Tyr Ser Asp Ser
    370                 375                 380

Ala Ser Asn Tyr Phe Pro Trp Tyr Lys Gln Glu Leu Gly Lys Arg Pro
385                 390                 395                 400

Gln Leu Ile Ile Asp Ile Arg Ser Asn Val Gly Glu Lys Lys Asp Gln
                405                 410                 415

Arg Ile Ala Val Thr Leu Asn Lys Thr Ala Lys His Phe Ser Leu His
            420                 425                 430

Ile Thr Glu Thr Gln Pro Glu Asp Ser Ala Val Tyr Phe Cys Ala Ala
        435                 440                 445

Ser Arg Gly Thr Gly Phe Gln Lys Leu Val Phe Gly Thr Gly Thr Arg
    450                 455                 460

Leu Leu Val Ser Pro Asn Ile Gln Asn Pro Asp Pro Ala Val Tyr Gln
465                 470                 475                 480

Leu Arg Asp Ser Lys Ser Ser Asp Lys Ser Val Cys Leu Phe Thr Asp
                485                 490                 495

Phe Asp Ser Gln Thr Asn Val Ser Gln Ser Lys Asp Ser Asp Val Tyr
            500                 505                 510

Ile Thr Asp Lys Thr Val Leu Asp Met Arg Ser Met Asp Phe Lys Ser
        515                 520                 525

Asn Ser Ala Val Ala Trp Ser Asn Lys Ser Asp Phe Ala Cys Ala Asn
    530                 535                 540

Ala Phe Asn Asn Ser Ile Ile Pro Glu Asp Thr Phe Phe Pro Ser Ser
545                 550                 555                 560

Asp Val Pro Cys Asp Val Lys Leu Val Glu Lys Ser Phe Glu Thr Asp
                565                 570                 575

Thr Asn Leu Asn Phe Gln Asn Leu Leu Val Ile Val Leu Arg Ile Leu
            580                 585                 590
```

```
Leu Leu Lys Val Ala Gly Phe Asn Leu Leu Met Thr Leu Arg Leu Trp
        595                 600                 605
Ser Ser
    610
```

MAGE A4 T CELL RECEPTORS

CROSS REFERENCE TO RELATED APPLICATIONS

This application is the National Stage of International Application No. PCT/EP2020/058779, filed Mar. 27, 2020, which claims the benefit of European Patent Application No. 19 165 387.2, filed Mar. 27, 2019, each of which is incorporated by reference herein in its entirety.

Statement Regarding Sequence Listing

The instant application contains a Sequence Listing which has been submitted electronically in ASCII format via EFS-Web, and is hereby incorporated by reference in its entirety. Said ASCII copy, created on May 16, 2022, is named 2SEV_115_01US_SubSeqList_ST25.txt and is 150124 bytes in size.

BACKGROUND

The present invention relates to isolated T cell receptors (TCRs) specific for MAGE-A4, polypeptides comprising a functional portion of a TCR, multivalent TCR complexes, nucleic acids encoding TCRs, cell expressing TCRs, and compositions and pharmaceutical compositions comprising the same. The present invention also relates to methods of using the foregoing in methods of medical treatment or for formulation and/or use as a medicament, in particular for use in the treatment of cancer.

DESCRIPTION OF THE RELATED ART

T lymphocytes (or T cells) which form part of the cell-mediated immune system play a major role in the eradication of pathogens. T cells develop in the thymus and express TCR molecules on their surface that allow the recognition of peptides presented on major histocompatibility complex (MIC) molecules which are expressed on nucleated cells (known as antigen presentation). Antigens derived from pathogens, i.e., foreign antigens presented by MHC molecules will elicit a powerful T cell response whereas self-antigens usually do not lead to a T cell response due to a negative selection of self-antigen specific T cells in the thymus during the development of such T cells. The immune system can thus discriminate between nucleated cells presenting foreign- or self-antigens and specifically target and eradicate infected cells via potent cytokine release and cellular cytotoxicity mechanisms of the T cells.

The power of the immune system has been recognized as a promising tool for future cancer therapies. In the last decades, research has begun to exploit the unique properties of T cells by using adoptive cell therapy (ACT), which involves the administration of patient-derived lymphocytes, expanded ex vivo. ACT is an attractive concept for the treatment of cancer because it does not require immune-competence of patients, and the specificity of transferred lymphocytes can be targeted against non-mutated and thus poorly immunogenic tumor antigens that typically fail to effectively trigger autologous T cell responses. Although ACT has been shown to be a promising treatment for various types of cancer, its broad application as clinical treatment has been hampered by the need for custom isolation and characterization of tumor-specific T cells from each patient—a process that can be not only difficult and time-consuming but also often fails to yield high-avidity T cells (Xue et al. *Clin. Exp. Immunol.* 2005 February; 139(2): 167-172; Schmitt et al., *Hum. Gene Ther.* 2009 November; 20(11): 1240-1248.)

The genetic transfer of tumor antigen-specific TCRs into primary T cells can overcome some of the current limitations of ACT, as it allows for the rapid generation of tumor-reactive T lymphocytes with defined antigen specificity even in immunocompromised patients. However, the identification of suitable T cell clones bearing TCRs that specifically recognize tumor antigens and exhibit the desired anti-tumor effects in vivo is still the topic of ongoing research. Considering that in 2012 about 14.1 million new cases of cancer occurred globally and that cancer currently is the cause of about 14.6% of all human deaths worldwide, novel and efficient treatment options are urgently needed. It is an object of the present invention to comply with the needs set out above.

MAGE-A4 belongs to the melanoma antigen (MAGE) family. The MAGE family is expressed in various malignant tumor types, ranging from melanoma, colon, lung to breast and other tumors. Specifically, the MAGE family is divided into two groups, based on its tissue expression pattern, where the MAGE-A subfamily is expressed in germ cells of the testis and aberrantly re-expressed in malignant tumors. This also applies to MAGE-A4.

Tumor tissue expression studies have revealed that MAGE-A4 is (over)expressed in 19-35% of non-small cell lung cancer (NSCLC) cases, 13% of breast cancer cases, 47% in epithelial ovarian cancer cases and 22% in colorectal cancer cases (Tajima et al. *Lung Cancer* 2003; 42: 23-33; Gure et al. *Clin Cancer Res* 2005, 11:8055-8062; Kim et al. *Int J Mol Med* 2012, 29: 656-662; Otte et al. *Cancer Res* 2001, 61:6682-668; Daudi et al. *PLoS One* 2014, 9:e104099; Li et al. *Clin Cancer Res* 2005, 11:1809-1814).

BRIEF SUMMARY

It is an objective of the invention to provide an isolated T cell receptor (TCR) specific for MAGE-A4.

In particular, the TCR specifically recognizes the amino acid sequence SEQ ID NO: 1 or a fragment thereof.

In specific embodiments, the TCR specifically recognizes the HLA-A2 bound form of the amino acid sequence of SEQ ID NO: 1, more specifically the TCR recognizes the amino acid sequence of SEQ ID NO: 1, which is presented by the HLA-A*02:01 encoded molecule.

In some embodiments, the TCR comprises: a variable TCR α region comprising a CDR1 having the amino acid sequence of SEQ ID NO: 2, a CDR2 having the amino acid sequence of SEQ ID NO: 3 and a CDR3 having the amino acid sequence of SEQ ID NO: 4, and a variable TCR β region comprising a CDR1 having the amino acid sequence of SEQ ID NO: 5, a CDR2 having the amino acid sequence of SEQ ID NO: 6 and a CDR3 having the amino acid sequence of SEQ ID NO: 7; or a variable TCR α region comprising a CDR1 having the amino acid sequence of SEQ ID NO: 12, a CDR2 having the amino acid sequence of SEQ ID NO: 13 and a CDR3 having the amino acid sequence of SEQ ID NO: 14, and a variable TCR β region comprising a CDR1 having the amino acid sequence of SEQ ID NO: 15, a CDR2 having the amino acid sequence of SEQ ID NO: 16 and a CDR3 having the amino acid sequence of SEQ ID NO: 17; or a variable TCR α region comprising a CDR1 having the amino acid sequence of SEQ ID NO: 22, a CDR2 having the amino acid sequence of SEQ ID NO: 23 and a CDR3 having the amino acid sequence of SEQ ID NO: 24, and a variable TCR β region comprising a CDR1 having the amino acid sequence of SEQ ID NO: 25, a CDR 2 having the amino acid sequence of SEQ ID NO: 26 and a CDR 3 having the amino acid sequence of SEQ ID NO: 27. These TCRs are described in more detail below.

In particular embodiments a TCR comprises: a variable TCR α region having the amino acid sequence of SEQ ID NO: 8 and a variable TCR β region having the amino acid sequence of SEQ ID NO: 9; or a variable TCR α region having the amino acid sequence of SEQ ID NO: 18 and a variable TCR β region having the amino acid sequence of SEQ ID NO: 19; or a variable TCR α region having the amino acid sequence of SEQ ID NO: 28 and a variable TCR β region having the amino acid sequence of SEQ ID NO: 29.

In certain embodiments, a TCR comprises: a TCR α chain having the amino acid sequence of SEQ ID NO: 10 and a TCR β chain having the amino acid sequence of SEQ ID NO: 11; a TCR α chain having the amino acid sequence of SEQ ID NO: 20 and a TCR β chain having the amino acid sequence of SEQ ID NO: 21; or a TCR α chain having the amino acid sequence of SEQ ID NO: 30 and a TCR β chain having the amino acid sequence of SEQ ID NO: 31.

In other embodiments, a TCR comprises: a TCR α chain having the amino acid sequence of SEQ ID NO: 87 and a TCR β chain having the amino acid sequence of SEQ ID NO: 88; a TCR α chain having the amino acid sequence of SEQ ID NO: 89 and a TCR β chain having the amino acid sequence of SEQ ID NO: 90; or a TCR α chain having the amino acid sequence of SEQ ID NO: 91 and a TCR β chain having the amino acid sequence of SEQ ID NO: 92.

In some embodiments, the TCR comprises: a TCR α chain having the amino acid sequence of SEQ ID NO: 102 and a TCR β chain having the amino acid sequence of SEQ ID NO: 103; a TCR α chain having the amino acid sequence of SEQ ID NO: 108 and a TCR β chain having the amino acid sequence of SEQ ID NO: 109; or a TCR α chain having the amino acid sequence of SEQ ID NO: 114 and a TCR β chain having the amino acid sequence of SEQ ID NO: 115.

TCRs contemplated herein are isolated and/or purified and may be soluble or membrane bound.

In some embodiments, the invention refers to an isolated TCR described herein, wherein the IFN-γ secretion induced by binding of the TCR expressed on an effector cell to the amino acid sequence of SEQ ID NO: 1, which is presented by the HLA-A*02:01 encoded molecule, may be more than 100 times higher, preferably 500 times higher, more preferably 2000 times higher when binding to the amino acid sequence of SEQ ID NO: 1, which is presented by the HLA-A*02:01 encoded molecule, compared to binding to an irrelevant peptide, which is presented by the HLA-A*02:01 encoded molecule.

In some embodiments, the amino acid sequence of the TCR may comprise one or more phenotypically silent substitutions. In addition, the TCRs can be labelled. Useful labels are known in the art and can be coupled to the TCR or TCR variant using routine methods, optionally via linkers of various lengths. The term "label" or "labelling group" refers to any detectable label. Additionally, or alternatively, the amino acid sequence may be modified to comprise a therapeutic agent or pharmacokinetic modifying moiety. The therapeutic agent may be selected from the group consisting of an immune effector molecule, a cytotoxic agent and a radionuclide. The immune effector molecule may for example be a cytokine. The pharmacokinetic modifying moiety may be at least one polyethylene glycol repeating unit, at least one glycol group, at least one sialyl group or a combination thereof.

The TCR, in particular a soluble form of the TCR contemplated herein can be modified by attaching additional functional moieties, e.g., for reducing immunogenicity, increasing hydrodynamic size (size in solution) solubility and/or stability (e.g., by enhanced protection to proteolytic degradation) and/or extending serum half-life. Other useful functional moieties and modifications include "suicide" or "safety switches" that can be used to shut off or turn on effector host cells carrying an inventive TCR in a patient's body. TCRs with an altered glycosylation pattern are also envisaged herein.

It is also conceivable to add a drug or a therapeutic entity, such as a small molecule compound to the TCR, in particular to a soluble form of the inventive TCR. The TCR, in particular a soluble form of the inventive TCR can additionally be modified to introduce additional domains which aid in identification, tracking, purification and/or isolation of the respective molecule (tags).

In some embodiments, a TCR is of the single chain type, wherein the TCR α chain and the TCR β chain are linked by a linker sequence, optionally wherein the linker sequence is cleavable.

Another aspect refers to a polypeptide comprising a functional portion of the TCR as described herein, wherein the functional portion comprises at least one of the amino acid sequences selected from the group consisting of SEQ ID NOs: 4, 7, 14, 17, 24 and 27.

In specific embodiments, the functional portion comprises the TCR α variable region and/or the TCR β variable region.

Specific embodiments refer to a multivalent TCR complex comprising at least two TCRs as described herein. In a more specific embodiment, at least one of said TCRs is associated with a therapeutic agent.

Particular embodiments refer to a fusion protein comprising a TCR α chain and a TCR β chain, wherein the fusion protein comprises the amino acid sequence set forth in any one of SEQ ID NOs: 94, 96, 98, 104, 110, and 116.

In specific aspects the fusion protein further comprises a furin cleavage site and/or a ribosomal skip sequence.

Another aspect refers to a nucleic acid encoding a TCR as described herein or encoding the polypeptide or fusion protein as described above.

In one aspect, a nucleic acid sequence encoding the TCRα chain is set forth in any one of SEQ ID NOs: 69, 77, 85, 99, 105, and 111. In another aspect, the nucleic acid sequence encoding the TCRβ chain is set forth in any one of SEQ ID NOs: 70, 78, 86, 100, 106, and 112. In other aspects, a TCR comprises an α chain encoded by SEQ ID NO: 69 and a β chain encoded by SEQ ID NO: 70; an α chain encoded by SEQ ID NO: 77 and a β chain encoded by SEQ ID NO: 78; an α chain encoded by SEQ ID NO: 85 and a β chain encoded by SEQ ID NO: 86; an α chain encoded by SEQ ID NO: 99 and a β chain encoded by SEQ ID NO: 100; an α chain encoded by SEQ ID NO: 105 and a β chain encoded by SEQ ID NO: 106; or an α chain encoded by SEQ ID NO: 111 and a β chain encoded by SEQ ID NO: 112.

Further aspects relate to a fusion protein encoded by the nucleic acid sequence set forth in any one of SEQ ID NOs: 93, 95, 97, 101, 107, and 113.

A further aspect refers to a plasmid or vector comprising the nucleic acid of the present application as described above. A further aspect refers to a plasmid or vector comprising a nucleic acid encoding the polypeptide sequences set forth in SEQ ID NO: 87 and SEQ ID NO: 88; the polypeptide sequences set forth in SEQ ID NO: 89 and SEQ ID NO: 90; the polypeptide sequences set forth in SEQ ID NO: 91 and SEQ ID NO: 92; the polypeptide sequences set forth in SEQ ID NO: 102 and SEQ ID NO: 103; the polypeptide sequences set forth in SEQ ID NO: 108 and SEQ ID NO: 109; or the polypeptide sequences set forth in SEQ ID NO: 114 and SEQ ID NO: 115. Preferably, the vector is an expression vector or a vector suitable for the transduction or transfection of cells, especially eukaryotic cells. The vector may be for example a retroviral vector, for example a gamma-retroviral or lentiviral vector.

Another aspect refers to a cell expressing a TCR as described herein. The cell may be isolated or non-naturally occurring.

Another aspect refers to a cell comprising the nucleic acid as described above or the plasmid or vector as described above. More specifically, the cell may comprise: an expression vector which comprises a nucleic acid or multiple nucleic acids as described above; or a first expression vector which comprises a nucleic acid encoding the alpha chain of the TCR as described herein, and a second expression vector which comprises a nucleic acid encoding the beta chain of a TCR as described herein.

The cell may be a peripheral blood lymphocyte (PBL) or a peripheral blood mononuclear cell (PBMC). Typically, the cell is an immune effector cell, especially a T cell. Other suitable cell types include gamma-delta T cells, natural killer (NK) cells, and NK-like T (NKT) cells.

Another aspect refers to an antibody or antigen binding fragment thereof specifically binding to a portion of the TCR as described herein which mediates specificity for MAGE-A4.

Another aspect refers to a composition comprising the TCR as described herein, the polypeptide as described herein, the fusion protein described herein, the multivalent TCR complex as described herein, the nucleic acid as described herein, the vector as described herein, the cell as described herein, or the antibody as described herein.

Another aspect refers to a pharmaceutical composition comprising the TCR as described herein, the polypeptide as described herein, the fusion protein described herein, the multivalent TCR complex as described herein, the nucleic acid as described herein, the vector as described herein, the cell as described herein, or the antibody as described herein.

Typically, the pharmaceutical composition comprises at least one pharmaceutically acceptable carrier.

Another aspect refers to TCR as described herein, the polypeptide as described herein, the multivalent TCR complex as described herein, the nucleic acid as described herein, the vector as described herein, the cell as described herein, the antibody as described herein, the composition described herein, or the pharmaceutical composition for use as a medicament, in particular for use in the treatment of cancer. The cancer may be a hematological cancer or a solid tumor. The cancer may be selected from the group consisting sarcoma, prostate cancer, uterine cancer, thyroid cancer, testicular cancer, renal cancer, pancreatic cancer, ovarian cancer, esophageal cancer, non-small-cell lung cancer, non-Hodgkin's lymphoma, multiple myeloma, melanoma, hepatocellular carcinoma, head and neck cancer, gastric cancer, endometrial cancer, colorectal cancer, cholangiocarcinoma, breast cancer, bladder cancer, myeloid leukemia and acute lymphoblastic leukemia. Preferably, the cancer is selected from the group consisting of NSCLC, SCLC, breast, ovarian or colorectal cancer, sarcoma and osteosarcoma.

DETAILED DESCRIPTION

A. Overview

Figure 1:
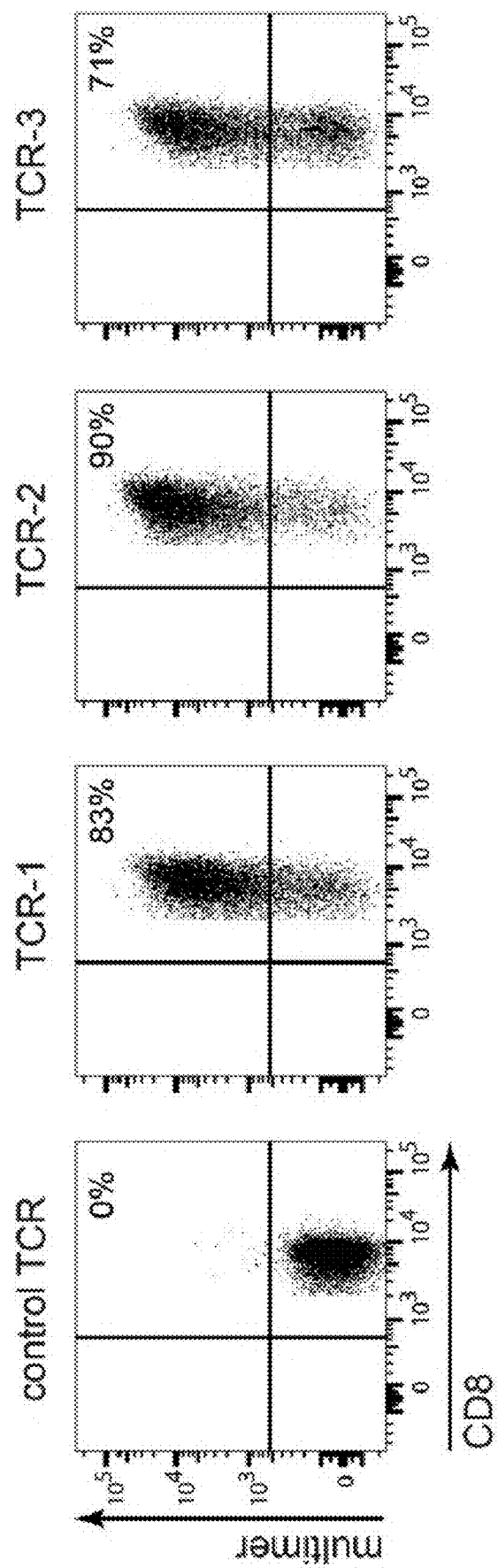
FIG. 1 shows the MAGE-A4$_{GVY}$-MHC-multimer binding of CD8+ T cells transduced with different MAGE-A4-reactive TCRs. CD8+ T cells were isolated from PBMCs of a healthy donor and transduced with three different MAGE-A4-TCRs and one control TCR that did not recognize MAGE-A4. Transduced CD8+ T cells were enriched by FACS using the murine constant beta region as a marker for transduction. After expansion of these cells, they were stained with an MAGE-A4$_{GVY}$-MHC-multimer and antibodies against CD8 and the murine constant beta region (mmCb) and analyzed by flow cytometry. Populations were gated on live CD8+/mCb+ cells and staining of multimer/CD8 is shown.

The MAGE-A4 expression pattern makes it a suitable tumor specific target for ACT. MAGE-A4 comprises an epitope in form of a decapeptide (Duffour et al. *Eur J Immunol.* 1999 10: 3329-37) having the amino acid sequence GVYDGREHTV (SEQ ID NO: 1) which is presented by HLA-A2 molecules. Taken together, MAGE-A4 is a suitable tumor specific target for ACT. Novel, safe and effective TCR effectors targeting MAGE-A antigens for cancer immunotherapy are needed. The present disclosure relates to T cell receptors that efficiently target MAGE-A4 antigens on cancer cells and aims to address this unmet medical need.

B. Definitions

Before aspects of the invention are described in more detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

For the purposes of the present invention, the term "obtained" is considered to be a preferred embodiment of the term "obtainable". If hereinafter e.g., an antibody is defined to be obtainable from a specific source, this is also to be understood to disclose an antibody, which is obtained from this source.

Where an indefinite or definite article is used when referring to a singular noun, e.g. "a," "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±10%, and preferably of ±5%, more preferably of ±2%, most preferably of ±1%.

Unless otherwise indicated, the term "at least" preceding a series of elements is to be understood to refer to every element in the series. The term "at least one" refers to one or more such as two, three, four, five, six, seven, eight, nine, ten or more. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and," "or," and "all or any other combination of the elements connected by said term".

The term "less than" or in turn "more than" does not include the concrete number. For example, less than 20 means less than the number indicated. Similarly, more than or greater than means more than or greater than the indicated number, e.g., more than 80% means more than or greater than the indicated number of 80%.

The term "including" means "including but not limited to." "Including" and "including but not limited to" are used interchangeably.

Throughout the description and claims of this specification, the singular encompasses the plural unless the context otherwise requires. In particular, where the indefinite article is used, the specification is to be understood as contemplating plurality as well as singularity, unless the context requires otherwise.

Technical terms are used by their common sense or meaning to the person skilled in the art. If a specific meaning is conveyed to certain terms, definitions of terms will be given in the following in the context of which the terms are used.

Additional definitions are set forth throughout this disclosure.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

C. TCR Background

A TCR is composed of two different and separate protein chains, namely the TCR alpha (α) and the TCR beta (β) chain. The TCR α chain comprises variable (V), joining (J) and constant (C) regions. The TCR β chain comprises variable (V), diversity (D), joining (J) and constant (C) regions. The rearranged V(D)J regions of both the TCR α and the TCR β chain contain hypervariable regions (CDR, complementarity determining regions), among which the CDR3 region determines the specific epitope recognition. At the C-terminal region both the TCR α chain and TCR β chain contain a hydrophobic transmembrane domain and end in a short cytoplasmic tail.

Typically, the TCR is a heterodimer of one α chain and one β chain. This heterodimer can bind to MHC molecules presenting a peptide.

The term "variable TCR α region" or "TCR α variable chain" or "variable domain" in the context refers to the variable region of a TCR α chain. The term "variable TCR β region" or "TCR β variable chain" in the context refers to the variable region of a TCR β chain.

The TCR loci and genes are named using the International Immunogenetics (IMGT) TCR nomenclature (IMGT Database, www.IMGT.org; Giudicelli et al. *Nucl. Acids Res.*, 34, D781-D784 (2006); Lefranc and Lefranc, Academic Press 2001).

D. MAGE-A4

A first aspect relates to an isolated T cell receptor (TCR) specific for MAGE-A4.

MAGE-A4 belongs to the group of so-called Cancer/Testis antigens. Cancer/Testis antigens are expressed in various malignant tumors and germ cells but in no other adult tissues. Therefore, MAGE-A4 is an interesting immunotherapeutic target antigen. The human gene encoding MAGE-A4 is designated MAGEA4 (ENSG00000147381).

In particular, a TCR contemplated herein specifically recognizes the epitope comprising the amino acids 230 to 239 of MAGE-A4, i.e., the amino acid sequence SEQ ID NO: 1 (GVYDGREHTV; also denoted herein as MAGE-A4$_{GVY}$) or a fragment thereof.

Typically, the TCR recognizes the peptide fragment of the antigen when it is presented by a major histocompatibility complex (MHC) molecule.

The human leukocyte antigen (HLA) system or complex is a gene complex encoding the major histocompatibility complex (MHC) proteins in humans. HLA-A*02 (HLA-A2) is one particular class I major histocompatibility complex (MHC) allele group at the HLA-A locus. HLA-A*02:01 is a specific HLA-A*02 allele.

Thus, in a specific embodiment, the TCR specifically recognizes the HLA-A2 bound form of the amino acid sequence of SEQ ID NO: 1. In an even more specific embodiment, the TCR specifically recognizes amino acid sequence of SEQ ID NO: 1, which is presented by the HLA-A*02:01 encoded molecule.

The TCR is highly specific for MAGE-A4 and exhibits no cross-reactivity to other peptides. That means that the TCR does not recognize normal human cell lines including cardiomyocytes, endothelial cells, lung fibroblasts, hepatocytes, renal cortical epithelial cells, astrocytes, bronchial epithelial cells and neurons that do not express MAGE-A4. The cross-reactivity may be measured by IFN-γ secretion as described herein.

The term "specific for" in the context means that the TCR is specifically binding to the target. In particular embodiments, a TCR is specific for MAGE-A4, and specifically binds to the amino acid sequence set forth in SEQ ID NO: 1 presented by an HLA-A*02:01 encoded molecule.

E. TCR Specific Sequence

The CDR3 of the TCR α chain of the TCR may have the amino acid sequence selected from the group consisting of SEQ ID NO: 4, SEQ ID NO: 14 and SEQ ID NO: 24.

The CDR3 of the TCR β chain of the TCR may have the amino acid sequence selected from the group consisting of SEQ ID NO: 7, SEQ ID NO: 17 and SEQ ID NO: 27.

Some embodiments relate to an isolated TCR comprising a TCR α chain and a TCR β chain, wherein a) the TCR α chain comprises a complementarity-determining region 3 (CDR3) having the amino acid sequence of SEQ ID NO: 4, and the TCR β chain comprises a CDR3 having the amino acid sequence of SEQ ID NO: 7; or b) the TCR α chain comprises a CDR3 having the amino acid sequence of SEQ ID NO: 14, and the TCR β chain comprises a CDR3 having the amino acid sequence of SEQ ID NO: 17; or c) the TCR α chain comprises a CDR3 having the amino acid sequence of SEQ ID NO: 24, and the TCR β chain comprises a CDR3 having the amino acid sequence of SEQ ID NO: 27.

More specific embodiments relate to an isolated TCR, wherein the TCR comprises: a) a TCR α chain comprising a CDR1 having the amino acid sequence of SEQ ID NO: 2, a CDR 2 having the amino acid sequence of SEQ ID NO: 3 and a CDR 3 having the amino acid sequence of SEQ ID NO: 4, and a TCR β chain comprising a CDR1 having the amino acid sequence of SEQ ID NO: 5, a CDR 2 having the amino acid sequence of SEQ ID NO: 6 and a CDR 3 having the amino acid sequence of SEQ ID NO: 7; or b) a TCR α chain comprising a CDR1 having the amino acid sequence of SEQ ID NO: 12, a CDR 2 having the amino acid sequence of SEQ ID NO: 13 and a CDR 3 having the amino acid sequence of SEQ ID NO: 14, and a TCR β chain comprising a CDR1 having the amino acid sequence of SEQ ID NO: 15, a CDR 2 having the amino acid sequence of SEQ ID NO: 16 and a CDR 3 having the amino acid sequence of SEQ ID NO: 17; or c) a TCR α chain comprising a CDR1 having the amino acid sequence of SEQ ID NO: 22, a CDR2 having the amino acid sequence of SEQ ID NO: 23 and a CDR3 having the amino acid sequence of SEQ ID NO: 24, a TCR β chain comprising a CDR1 having the amino acid sequence of SEQ ID NO: 25, a CDR 2 having the amino acid sequence of SEQ ID NO: 26 and a CDR 3 having the amino acid sequence of SEQ ID NO: 27.

Preferred embodiments relate to isolated TCRs which are defined by the CDRs, in particular by the CDR3 of the TCR α and the TCR β chain as described above, wherein the recombinant TCR sequence is modified to contain murinized, preferably minimal murinized Cα and Cβ regions.

In particularly preferred embodiments, isolated TCRs are defined by the CDRs, in particular by the CDR3 of the TCR α and the TCR β chain as described above, wherein the recombinant TCR sequence is modified to contain minimal murinized Cα and Cβ regions and hydrophobic amino acid mutations in the Cα transmembrane domain. In particular embodiments, these TCRs have increased expression and functional avidity compared to TCRs that are not minimally murinized and do not contain hydrophobic mutations in the Cα transmembrane region.

In further preferred embodiments, isolated TCRs are defined by the CDRs, in particular by the CDR3 of the TCR α and the TCR β chain as described above, wherein the recombinant TCR sequence is not modified to contain murinized, or minimally murinized Cα and Cβ regions.

Some embodiments refer to an isolated TCR, wherein the TCR comprises: a) a variable TCR α region having an amino acid sequence which is at least 80% identical to SEQ ID NO: 8 and a variable TCR β region having an amino acid sequence which is at least 80% identical to SEQ ID NO: 9; or b) a variable TCR α region having an amino acid sequence which is at least 80% identical to SEQ ID NO: 18 and a variable TCR β region having an amino acid sequence which is at least 80% identical to SEQ ID NO: 19; or c) a variable TCR α region having an amino acid sequence which is at least 80% identical to SEQ ID NO: 28 and a variable TCR β region having an amino acid sequence which is at least 80% identical to SEQ ID NO: 29.

"At least 80% identical", in particular "having an amino acid sequence which is at least 80% identical" as used herein includes that the amino acid sequence is at least 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence set out.

In some embodiments the TCR comprises a TCR α chain and a TCR β chain, wherein a) the variable TCR α region has an amino acid sequence which is at least 80% identical to SEQ ID NO: 8 and comprises a CDR3 having the amino acid sequence set out in SEQ ID NO: 4, and the variable TCR β region has an amino acid sequence which is at least 80% identical to SEQ ID NO: 9 and comprises a CDR3 having the amino acid sequence set out SEQ ID NO: 7 or b) the variable TCR α region has an amino acid sequence which is at least 80% identical to SEQ ID NO: 18 and comprises a CDR3 having the amino acid sequence set out in SEQ ID NO: 14, and the variable TCR β region has an amino acid sequence which is at least 80% identical to SEQ ID NO: 19 and comprises a CDR3 having the amino acid sequence set out SEQ ID NO: 17; or c) the variable TCR α region has an amino acid sequence which is at least 80% identical to SEQ ID NO: 28 and comprises a CDR3 having the amino acid sequence set out in SEQ ID NO: 24; and the variable TCR β region has an amino acid sequence which is at least 80% identical to SEQ ID NO: 29 and comprises a CDR3 having the amino acid sequence set out SEQ ID NO: 27.

Exemplary embodiments refer to an isolated TCR, wherein the TCR comprises: a) a variable TCR α region having the amino acid sequence of SEQ ID NO: 8 and a variable TCR β region having the amino acid sequence of SEQ ID NO: 9; or b) a variable TCR α region having the amino acid sequence of SEQ ID NO: 18 and a variable TCR β region having the amino acid sequence of SEQ ID NO: 19; or c) a variable TCR α region having the amino acid sequence of SEQ ID NO: 28 and a variable TCR β region having the amino acid sequence of SEQ ID NO: 29.

The following table shows a summary of the exemplary TCRs

| TCR | CDR1α | CDR2α | CDR3α | TRAV | TRAJ | CDR1β | CDR2β | CDR3β | TRBV | TRBJ |
|---|---|---|---|---|---|---|---|---|---|---|
| 1, 4, 7 | TSDQSYG | QGSYDEQN | CAMSGDSAGNMLTF | 14 | 39 | KGHDR | SFDVKD | CATSDWDRSGDKETQYF | 24 | 2-5 |
| 2, 5, 8 | TSDPSYG | QGSYDQQN | CAMSGGYTGGFKTIF | 14 | 9 | SGDLS | YYNGEE | CASSGGDGDEQFF | 9 | 2-1 |
| 3, 6, 9 | DSASNY | IRSNVGE | CAASRGTGFQKLVF | 13 | 8 | LGHDT | YNNKEL | CASSQFWDGAGDEQYF | 3-1 | 2-7 |

As can be seen from the examples, the TCRs contemplated herein are specific for MAGE-A4.

The determination of percent identity between multiple sequences is preferably accomplished using the AlignX application of the Vector NTI Advance™ 10 program (Invitrogen Corporation, Carlsbad CA, USA). This program uses a modified Clustal W algorithm (Thompson et al. *Nucl Acids Res* 1994; 42: 23-33; Invitrogen Corporation. User Manual 2004; 389-662). The determination of percent identity is performed with the standard parameters of the AlignX application.

The TCR contemplated herein are isolated or purified. "Isolated" means that the TCR is not present in the context in which it originally occurred in nature. "Purified" means e.g., that the TCR is free or substantially free of other proteins and non-protein parts of the cell it originally stems from.

In some embodiments, the amino acid sequence of the TCR may comprise one or more phenotypically silent substitutions.

"Phenotypically silent substitutions" are also named "conservative amino acid substitutions." The concept of "conservative amino acid substitutions" is understood by the skilled artisan, and preferably means that codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. These variations can spontaneously occur, be introduced by random mutagenesis, or can be introduced by directed mutagenesis. Those changes can be made without destroying the essential characteristics of these polypeptides. The ordinarily skilled artisan can readily and routinely screen variant amino acids and/or the nucleic acids encoding them to determine if these variations substantially reduce or destroy the ligand binding capacity by methods known in the art.

According to some embodiments, the amino acid sequence of the TCR is modified to comprise a detectable label, a therapeutic agent or pharmacokinetic modifying moiety.

Non-limiting examples for detectable labels are radiolabels, fluorescent labels, nucleic acid probes, enzymes and contrast reagents. Therapeutic agents which may be associated with the TCRs include radioactive compounds, immunomodulators, enzymes or chemotherapeutic agents. The therapeutic agents could be enclosed by a liposome linked to TCR so that the compound can be released slowly at the target site. This will avoid damage during the transport in the body and ensure that the therapeutic agent, e.g., toxin, exerts its maximum effect after binding of the TCR to the relevant antigen presenting cells. Other examples for therapeutic agents are: peptide cytotoxins, i.e. proteins or peptides with the ability to kill mammalian cells, such as ricin, diphtheria toxin, pseudomonas bacterial exotoxin A, DNase and RNase. Small molecule cytotoxic agents, i.e., compounds with the ability to kill mammalian cells having a molecular weight of less than 700 Daltons. Such compounds could contain toxic metals capable of having a cytotoxic effect.

Furthermore, it is to be understood that these small molecule cytotoxic agents also include pro-drugs, i.e., compounds that decay or are converted under physiological conditions to release cytotoxic agents. Such agents may for example include docetaxel, gemcitabine, cis-platin, maytansine derivatives, rachelmycin, calicheamicin, etoposide, ifosfamide, irinotecan, porfimer sodium photofrin II, temozolomide, topotecan, trimetrexate glucoronate, mitoxantrone, auristatin E, vincristine and doxorubicin; radionuclides, such as, iodine 131, rhenium 186, indium 111, yttrium 90. bismuth 210 and 213, actinium 225 and astatine 213. The association of the radionuclides with the TCRs or derivatives thereof may for example be carried out by chelating agents; immunostimulators, also known as immunostimulants, i.e., immune effector molecules which stimulate immune response. Exemplary immunostimulators are cytokines such as IL-2 and IFN-γ, antibodies or fragments thereof, including anti-T cell or NK cell determinant antibodies (e.g., anti-CD3, anti-CD28 or anti-CD16); alternative protein scaffolds with antibody like binding characteristics; superantigens, i.e., antigens that cause non-specific activation of T-cells resulting in polyclonal T cell activation and massive cytokine release, and mutants thereof, chemokines such as IL-8, platelet factor 4, melanoma growth stimulatory protein, etc. complement activators; xenogeneic protein domains, allogeneic protein domains, viral/bacterial protein domains, viral/bacterial peptides.

The antigen receptor molecules (T cell receptor molecules) on human T lymphocytes are non-covalently associated with the CD3 (T3) molecular complex on the cell surface. Perturbation of this complex with anti-CD3 monoclonal antibodies induces T cell activation. Thus, some embodiments refer to a TCR as described herein associated (usually by fusion to a N- or C-terminus of the alpha or beta chain) with an anti-CD3 antibody, or a functional fragment or variant of said anti-CD3 antibody. Antibody fragments and variants/analogues which are suitable for use in the compositions and methods described herein include minibodies, Fab fragments, F(ab')2 fragments, dsFv and scFv fragments, Nanobodies™ (Ablynx (Belgium)), molecules comprising synthetic single immunoglobulin variable heavy chain domain derived from a camelid (e.g., camel or llama or alpaca) antibody) and Domain Antibodies (comprising an affinity matured single immunoglobulin variable heavy chain domain or immunoglobulin variable light chain domain (Domantis (Belgium)) or alternative protein scaffolds that exhibit antibody-like binding characteristics such as Affibodies (comprising engineered protein A scaffold Affibody (Sweden)) or Anticalins (comprising engineered anticalins Pieris (Germany)).

The therapeutic agent may preferably be selected from the group consisting of an immune effector molecule, a cytotoxic agent and a radionuclide. Preferably, the immune effector molecule is a cytokine.

The pharmacokinetic modifying moiety may be for example at least one polyethylene glycol repeating unit, at least one glycol group, at least one sialyl group or a combination thereof. The association of at least one polyethylene glycol repeating unit, at least one glycol group, at least one sialyl group may be caused in a number of ways known to those skilled in the art. In a preferred embodiment, the units are covalently linked to the TCR. The TCRs contemplated herein can be modified by one or several pharmacokinetic modifying moieties. In particular, the soluble form of the TCR is modified by one or several pharmacokinetic modifying moieties. The pharmacokinetic modifying moiety may achieve beneficial changes to the pharmacokinetic profile of the therapeutic, for example improved plasma half-life, reduced or enhanced immunogenicity, and improved solubility.

The TCR contemplated herein may be soluble or membrane bound. The term "soluble" refers to a TCR being in soluble form (i.e., having no transmembrane or cytoplasmic domains), for example for use as a targeting agent for delivering therapeutic agents to the antigen presenting cell. For stability, soluble αβ heterodimeric TCRs preferably have an introduced disulfide bond between residues of the respective constant domains, as described, for example, in WO 03/020763. One or both of the constant domains present in an αβ heterodimer may be truncated at the C terminus or C termini, for example by up to 15, or up to 10 or up to 8 or fewer amino acids. For use in adoptive therapy, an αβ heterodimeric TCR may, for example, be transfected as full-length chains having both cytoplasmic and transmembrane domains. TCRs may contain a disulfide bond corresponding to that found in nature between the respective alpha and beta constant domains, additionally or alternatively a non-native disulfide bond may be present.

The TCR, in particular a soluble form of the TCR contemplated herein can thus be modified by attaching additional functional moieties, e.g., for reducing immunogenicity, increasing hydrodynamic size (size in solution) solubility and/or stability (e.g., by enhanced protection to proteolytic degradation) and/or extending serum half-life. Other useful functional moieties and modifications include "suicide" or "safety switches" that can be used to shut off effector host cells carrying an inventive TCR in a patient's body. An example is the inducible Caspase 9 (iCasp9) "safety switch" described by Gargett and Brown. *Front Pharmacol* 2014; 5: 235. Briefly, effector host cells are modified by well-known methods to express a Caspase 9 domain whose dimerization depends on a small molecule dimerizer drug such as AP1903/CIP, and results in rapid induction of apoptosis in the modified effector cells. The system is for instance described in EP2173869 (A2). Examples for other "suicide" or "safety switches" are known in the art, e.g., Herpes Simplex Virus thymidine kinase (HSV-TK), expression of CD20 and subsequent depletion using anti-CD20 antibody or myc tags (Kieback et al. *Proc Natl Acad Sci USA* 2008 15; 105(2):623-628).

TCRs with an altered glycosylation pattern are also envisaged herein. As is known in the art, glycosylation patterns can depend on the amino acid sequence (e.g., the presence or absence of particular glycosylation amino acid residues, discussed below) and/or the host cell or organism in which the protein is produced. Glycosylation of polypeptides is typically either N-linked or 0-linked. N-linked refers to the attachment of the carbohydrate moiety to the side chain of an asparagine residue. Addition of N-linked glycosylation sites to the binding molecule is conveniently accomplished by altering the amino acid sequence such that it contains one or more tri-peptide sequences selected from asparagine-X-serine and asparagine-X-threonine (where X is any amino acid except proline). O-linked glycosylation sites may be introduced by the addition of or substitution by, one or more serine or threonine residues to the starting sequence.

Another means of glycosylation of TCRs is by chemical or enzymatic coupling of glycosides to the protein. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. Similarly, deglycosylation (i.e., removal of carbohydrate moieties present on the binding molecule) may be accomplished chemically, e.g., by exposing the TCRs to trifluoromethanesulfonic acid, or enzymatically by employing endo- and exo-glycosidases.

It is also conceivable to add a drug such as a small molecule compound to the TCR, in particular a soluble form of the inventive TCR. Linkage can be achieved via covalent bonds, or non-covalent interactions such as through electrostatic forces. Various linkers, known in the art, can be employed in order to form the drug conjugates.

The TCR, in particular a soluble form of the inventive TCR, can additionally be modified to introduce additional domains which aid in identification, tracking, purification and/or isolation of the respective molecule (tags). Thus in some embodiments, the TCR α chain or the TCR β chain may be modified to comprise an epitope tag.

Epitope tags are useful examples of tags that can be incorporated into the TCR. Epitope tags are short stretches of amino acids that allow for binding of a specific antibody and therefore enable identification and tracking of the binding and movement of soluble TCRs or host cells within the patient's body or cultivated (host) cells. Detection of the epitope tag, and hence, the tagged TCR, can be achieved using a number of different techniques. Tags can further be employed for stimulation and expansion of host cells carrying an inventive TCR by cultivating the cells in the presence of binding molecules (antibodies) specific for said tag.

In general, the TCR can be modified in some instances with various mutations that modify the affinity and the off-rate of the TCR with the target antigen. In particular, the mutations may increase the affinity and/or reduce the off-rate. Thus, the TCR may be mutated in at least one CDR and the variable domain framework region thereof.

However, in a preferred embodiment the CDR regions of the TCR are not modified or in vitro affinity maturated such as for the TCR receptors in the examples. This means that the CDR regions have naturally occurring sequences. This can be advantageous, since in vitro affinity maturation may lead to immunogenicity to the TCR molecule. This may lead to the production of anti-drug antibodies decreasing or inactivating the therapeutic effect and the treatment and/or induce adverse effects.

The mutation may be one or more substitution(s), deletion (s) or insertions(s). These mutations may be introduced by any suitable method known in the art, such as DNA synthesis, polymerase chain reaction, restriction enzyme-based cloning, ligation independent cloning procedures, which are described for example in Sambrook, Cold Spring Harbor Laboratory Press 2012.

Theoretically, unpredictable TCR specificity with the risk for cross-reactivity can occur due to mispairing between endogenous and exogenous TCR chains. To avoid mispairing of TCR sequences, the recombinant TCR sequence may be modified to contain minimal murinized Cα and Cβ regions, a technology that has been shown to efficiently enhance correct pairing of several different transduced TCR chains. Murinization of TCRs (i.e. exchanging the human constant regions in the alpha and beta chain by their murine counterparts) is a technique that is commonly applied in order to improve cell surface expression of TCRs in host cells. Without wishing to be bound by specific theory, it is thought that murinized TCRs associate more effectively with CD3 co-receptors; and/or that preferentially pair with each other and are less prone to form mixed TCRs on human T cells genetically modified ex vivo to express the TCRs of desired antigenic specificity, but still retaining and expressing their "original" TCRs.

Nine amino acids responsible for the improved expression of murinized TCRs have been identified (Sommermeyer and Uckert, *J Immunol.* 2010; 184(11):6223-6231) and it is envisaged to substitute one or all of the amino acid residues in the TCRs alpha and/or beta chain constant region for their murine counterpart residues. This technique is also referred to as "minimal murinization" and offers the advantage of enhancing cell surface expression while, at the same time, reducing the number of "foreign" amino acid residues in the amino acid sequence and, thereby, the risk of immunogenicity.

In a preferred embodiment the TCRs containing minimal murinized Cα and Cβ regions are TCR-1 comprising the α chain of SEQ ID NO: 10 and the β chain of SEQ ID NO: 11, TCR-2 comprising the α chain of SEQ ID NO: 20 and the β chain of SEQ ID NO: 21, TCR-3 comprising the α chain of SEQ ID NO: 30 and the β chain of SEQ ID NO: 31.

In preferred embodiments, the TCRs contain minimally murinized Cα and Cβ regions and further comprise hydrophobic amino acid mutations in the Cα transmembrane domain. The transmembrane domain of the TCR α chain has been shown to contribute to the lack of stability of the whole chain and thereby affecting the formation and surface expression of the whole TCR-CD3 complex. Substitution of three amino acids in the TCR α transmembrane domain with the hydrophobic amino acids leucine or valine increased TCR expression and functional avidity. Haga-Friedman et al. *J Immunology* 2012; 188:5538-5546.

In a preferred embodiment the TCRs containing minimally murinized Cα and Cβ regions and hydrophobic amino acid substitutions in the TCR α chain are TCR-7 comprising the α chain of SEQ ID NO: 102 and the β chain of SEQ ID NO: 103, TCR-8 comprising the α chain of SEQ ID NO: 108 and the β chain of SEQ ID NO: 109, TCR-9 comprising the α chain of SEQ ID NO: 114 and the R chain of SEQ ID NO: 115.

Some embodiments refer to an isolated TCR as described herein, wherein the TCR is of the single chain type, wherein the TCR α chain and the TCR β chain are linked by a linker sequence, optionally wherein the linker is cleavable.

A suitable single chain TCR form comprises a first segment constituted by an amino acid sequence corresponding to a variable TCR α region, a second segment constituted by an amino acid sequence corresponding to a variable TCR β region fused to the N terminus of an amino acid sequence corresponding to a TCR β chain constant region extracellular sequence, and a linker sequence linking the C terminus of the first segment to the N terminus of the second segment. Alternatively, the first segment may be constituted by an amino acid sequence corresponding to a TCR β chain variable region, the second segment may be constituted by an amino acid sequence corresponding to a TCR α chain variable region sequence fused to the N terminus of an amino acid sequence corresponding to a TCR α chain constant region extracellular sequence. The above single chain TCRs may further comprise a disulfide bond between the first and second chains, and wherein the length of the linker sequence and the position of the disulfide bond being such that the variable domain sequences of the first and second segments are mutually orientated substantially as in native T cell receptors. More specifically, the first segment may be constituted by an amino acid sequence corresponding to a TCR α chain variable region sequence fused to the N terminus of an amino acid sequence corresponding to a TCR α chain constant region extracellular sequence, the second segment may be constituted by an amino acid sequence corresponding to a TCR β chain variable region fused to the N terminus of an amino acid sequence corresponding to TCR β chain constant region extracellular sequence, and a disulfide bond may be provided between the first and second chains. The linker sequence may be any sequence which does not impair the function of the TCR.

A "functional" TCR α and/or β chain fusion protein shall mean a TCR or TCR variant, for example modified by addition, deletion or substitution of amino acids, that maintains at least substantial biological activity. In the case of the α and/or β chain of a TCR, this shall mean that both chains remain able to form a T-cell receptor (either with a non-modified α and/or β chain or with another inventive fusion protein α and/or β chain) which exerts its biological function, in particular binding to the specific peptide-MHC complex of said TCR, and/or functional signal transduction upon specific peptide: MHC interaction.

In specific embodiments, the TCR may be modified, to be a functional T-cell receptor (TCR) α and/or β chain fusion protein, wherein said epitope-tag has a length of between 6 to 15 amino acids, preferably 9 to 11 amino acids. In another embodiment the TCR may be modified to be a functional T-cell receptor (TCR) a and/or β chain fusion protein wherein said T-cell receptor (TCR) a and/or R chain fusion protein comprises two or more epitope-tags, either spaced apart or directly in tandem. Embodiments of the fusion protein can contain 2, 3, 4, 5 or even more epitope-tags, as long as the fusion protein maintains its biological activity/activities ("functional").

Preferred is a functional T-cell receptor (TCR) a and/or β chain fusion protein according to the present invention, wherein said epitope-tag is selected from, but not limited to, CD20 or Her2/neu tags, or other conventional tags such as a myc-tag, FLAG-tag, T7-tag, HA (hemagglutinin)-tag, His-tag, S-tag, GST-tag, or GFP-tag. Myc-, T7-, GST-, GFP-tags are epitopes derived from existing molecules. In contrast, FLAG is a synthetic epitope tag designed for high antigenicity (see, e.g., U.S. Pat. Nos. 4,703,004 and 4,851,341). The myc tag can preferably be used because high quality reagents are available to be used for its detection. Epitope tags can of course have one or more additional functions, beyond recognition by an antibody. The sequences of these tags are described in the literature and well known to the person of skill in art.

In more preferred embodiments, an isolated TCR is expressed as a fusion protein, wherein the TCR α chain and the TCR β chain are separated by one or more polypeptide cleavage signal signals. In particular embodiments, a fusion protein comprises from 5' to 3': a TCR α chain, one or more polypeptide cleavage signal signals, and a TCR β chain. In particular embodiments, a fusion protein comprises from 5' to 3': a TCR β chain, one or more polypeptide cleavage signal signals, and a TCR α chain.

Polypeptide cleavage signals contemplated herein include, but are not limited to, protease cleavage sites and ribosomal skip sequences. A polypeptide cleavage signal may be disposed between each of the polypeptide domains described herein, e.g., a TCR α chain and a TCR β chain. In addition, a polypeptide cleavage signal can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides or ribosomal skipping sequences (see deFelipe and Ryan, 2004. *Traffic,* 5(8); 616-26).

Illustrative examples of protease cleavage sites suitable for use in particular embodiments include but are not limited to furin (e.g., Arg-X-X-Arg, such as Arg-X-Lys/Arg-Arg or Arg-Gln/Tyr-Lys/Arg-Arg. Furin may further cleave the sequences Arg-Ala-Arg-Tyr-Lys-Arg or Arg-Ala-Arg-Tyr-Lys-Arg-Ser); subtilisins (e.g., PC2, PC1/PC3, PACE4, PC4, PC5/PC6, LPC/PC7IPC8/SPC7 and SKI-I); enterokinase (e.g., Asp-Asp-Asp-Aps-Lys* and Asp/Glu-Arg-*Met); factor Xa (e.g., Glu-Gly-Arg*); thrombin (e.g., Leu-Val-Pro-Arg*Gly-Ser); Granzyme B (e.g., Ile-Glu-Pro-Asp*); Caspase-3 (e.g., Asp-Glu-Val-Asp*); and the like.

Illustrative examples of self-cleaving viral peptides or ribosomal skipping sequences include but are not limited to a 2A or 2A-like site, sequence or domain (Donnelly et al., 2001. *J. Gen. Virol.* 82:1027-1041). In particular embodiments, the viral 2A peptide is an aphthovirus 2A peptide, a potyvirus 2A peptide, or a cardiovirus 2A peptide. In preferred embodiments, the viral 2A peptide is selected from the group consisting of: a foot-and-mouth disease virus 2A peptide (F2A), an equine rhinitis A virus 2A peptide (E2A), a *Thosea asigna* virus 2A peptide (T2A), a porcine teschovirus-1 2A peptide (P2A), a Theilovirus 2A peptide, and an encephalomyocarditis virus 2A peptide.

In certain embodiments, a fusion protein comprises a TCR α chain, a proteolytic cleavage site and/or a ribosomal skip sequence and a TCR β chain. In preferred embodiments, the fusion protein comprises a TCR α chain, a furin cleavage site and/or a P2A ribosomal skip sequence and a TCR β chain. In other preferred embodiments, the fusion protein comprises a TCR α chain, a P2A ribosomal skip sequence, and a TCR β chain.

In particular embodiments, a fusion protein comprises a TCR β chain, a proteolytic cleavage site and/or a ribosomal skip sequence and a TCR α chain. In preferred embodiments, the fusion protein comprises a TCR β chain, a furin cleavage site and/or a P2A ribosomal skip sequence and a TCR α chain. In other preferred embodiments, the fusion protein comprises a TCR β chain, a P2A ribosomal skip sequence, and a TCR α chain.

In preferred embodiments, fusion proteins comprise an amino acid sequence set forth in any one of SEQ ID NOs: 94, 96, 98, 104, 110, and 116.

F. TCR Fragments and Variants

Another aspect refers to a polypeptide comprising a functional portion of the TCR of as described herein. The functional portion may comprise at least one of the amino acid sequences selected from the group consisting of SEQ ID NO: 4, SEQ ID NO: 14, SEQ ID NO: 24, SEQ ID NO: 7, SEQ ID NO: 17, SEQ ID NO: 27.

In specific embodiments the polypeptide may the functional portion of the TCR alone, e.g., in a soluble form. Alternatively, the polypeptide may be combined with other domains.

The functional portion may mediate the binding of the TCR to the antigen, in particular to the antigen-MHC complex. In one embodiment, the functional portion comprises the TCR α variable chain and/or the TCR β variable chain as described herein.

The TCR variant molecule, i.e., a molecule combining a polypeptide comprising a functional portion of the TCR with other domains, may have the binding properties of the TCR receptor but may be combined with signaling domains of effectors cells (other than T cells), in particular with signaling domains of NK cells. Therefore, some embodiments refer to a protein comprising a functional portion of the TCR as described herein in combination with the signaling domains of an immune effector cell, such as a NK cell.

"Binding" refers to the ability to specifically and non-covalently associate, unite or bind with the target.

Another aspect refers to a multivalent TCR complex comprising at least two TCRs as described herein. In one embodiment of this aspect, at least two TCR molecules are linked via linker moieties to form multivalent complexes. Preferably, the complexes are water soluble, so the linker moiety should be selected accordingly. It is preferable that the linker moiety is capable of attaching to defined positions on the TCR molecules, so that the structural diversity of the complexes formed is minimized. One embodiment of the present aspect is provided by a TCR complex wherein the polymer chain or peptidic linker sequence extends between amino acid residues of each TCR, which are not located in a variable region sequence of the TCR. Since the complexes may be for use in medicine, the linker moieties should be chosen with due regard to their pharmaceutical suitability, for example their immunogenicity. Examples of linker moieties, which fulfil the above desirable criteria are known in the art, for example the art of linking antibody fragments.

Examples for linkers are hydrophilic polymers and peptide linkers. An example for hydrophilic polymers are polyalkylene glycols. The most commonly used of this class are based on polyethylene glycol or PEG. However, others are based on other suitable, optionally substituted, polyalkylene glycols which include polypropylene glycol, and copolymers of ethylene glycol and propylene glycol. Peptide linkers are comprised of chains of amino acids, and function to produce simple linkers or multimerization domains onto which TCR molecules can be attached.

One embodiment refers to a multivalent TCR complex, wherein at least one of said TCRs is associated with a therapeutic agent.

G. Cytokine and Chemokine Release

Some embodiments refer to the isolated TCR as described herein, polypeptide as described herein, multivalent TCR complex as described herein, wherein IFN-γ secretion is induced by binding of the inventive TCR expressed on an effector cell to the amino acid sequence of SEQ ID NOs: 1 which is presented by the HLA-A*02:01 encoded molecule.

The IFN-γ secretion induced by binding of the inventive TCR expressed on an effector cell to the amino acid sequence of SEQ ID NO: 1, which is presented by the HLA-A*02:01 encoded molecule, may be more than 100 times higher, preferably 500 times higher, more preferably 2000 times higher when binding to the amino acid sequence of SEQ ID NO: 1, which is presented by the HLA-A*02:01 encoded molecule, compared to binding to an irrelevant peptide (ASTN1, SEQ ID NO. 56, KLYGLDWAEL), which is presented by the HLA-A*02:01 encoded molecule. The IFN-γ secretion may be for example more than 100 pg/ml, such as more than 500 pg/ml or more than 2000 pg/ml.

The cytokine and chemokine release, such as IFN-γ secretion may be measured using an in vitro assay in which K562 cells (Greiner et al. 2006, *Blood.* 2006 Dec. 15; 108(13):4109-17) are transfected with ivtRNA or transduced to express the amino acid sequence of SEQ ID NO: 1 or irrelevant peptide, respectively, and are incubated with CD8$^+$ enriched and/or non-CD8$^+$-enriched PBMCs expressing the TCR to be investigated or in an in vitro assay using T2 cells externally loaded with either the SEQ ID NO: 1 or the irrelevant peptide and subsequently co-incubated with CD8$^+$ enriched and/or non-CD8$^+$-enriched PBMCs expressing the TCR to be investigated.

Some embodiments refer to an isolated TCR as described herein, polypeptide as described herein or multivalent TCR complex as described herein, wherein IFN-γ secretion induced by binding of the inventive TCR expressed on an effector cell to the amino acid sequence of SEQ ID NO: 1 or 5 in particular to the amino acid sequence of SEQ ID NO: 1 which is presented by the HLA-A*02:01 encoded molecule is below a predefined threshold. The threshold may be determined by using a specific effector to target ratio of at least 2:1.

The "effector cell" may be a peripheral blood lymphocyte (PBL) or a peripheral blood mononuclear cell (PBMC). Typically, the effector cell is an immune effector cell, especially a T cell. Other suitable cell types include gamma-delta T cells, natural killer (NK) cells, and NK-like T (NKT) cells.

The IFN-γ secretion upon binding of the inventive TCR expressed on an effector cell to amino acid sequence of SEQ ID NO: 1 which is presented by the HLA-A*02:01 encoded molecule may be induced at a MAGE-A4 peptide concentration of at least $10^{-7}$ [M], preferably at least $10^{-8}$ [M], more preferably $10^{-9}$ [M]. In specific embodiments, for example when the ratio of TCR-transgenic T cells to T2 cells is 2:1, the IFN-γ secretion upon by binding of the inventive TCR expressed on an effector cell to amino acid sequence of SEQ ID NO: 1 which is presented by the HLA-A*02:01 encoded molecule may be induced at a MAGE-A4 peptide concentration of at least $10^{-7}$ [M], preferably at least $10^{-8}$ [M], more preferably $10^{-9}$ [M].

The invention relates also to methods for identifying a TCR or a fragment thereof that binds to the target amino acid sequence SEQ ID NO: 1, which is presented by the HLA-A*02:01 encoded molecule, wherein the method comprises contacting the candidate TCR or fragment thereof with the amino acid sequence SEQ ID NO: 1, which is presented by the HLA-A*02:01 encoded molecule, and determining whether the candidate TCR or fragment thereof binds to the target and/or mediates an immune response.

Whether the candidate TCR or fragment thereof mediates an immune response can be determined for example by the measurement of cytokine secretion, such as IFN-γ secretion. As described above cytokine secretion may be e.g., measured by an in vitro assay in which K562 cells (or other APCs) transfected with ivtRNA coding the amino acid sequence SEQ ID NO: 1 are incubated with CD8+ enriched PBMC expressing the TCR or a molecule comprising a fragment of the TCR to be investigated.

H. Nucleic Acids, Vectors

Another aspect refers to a nucleic acid encoding a TCR as described herein or encoding the polynucleotide encoding a TCR as described herein.

The following table indicates the nucleotide sequences encoding the respective peptide sequences:

| Polypeptide SEQ ID NO | Polynucleotide SEQ ID NO | Description |
|---|---|---|
| 2 | 32 | TCR-1 α chain CDR1 |
| 3 | 33 | TCR-1 α chain CDR2 |
| 4 | 34 | TCR-1 α chain CDR3 |
| 5 | 35 | TCR-1 β chain CDR1 |
| 6 | 36 | TCR-1 β chain CDR2 |
| 7 | 37 | TCR-1 β chain CDR3 |
| 10 | 38 | TCR-1 α chain complete |
| 11 | 39 | TCR-1 β chain complete |

-continued

| Polypeptide SEQ ID NO | Polynucleotide SEQ ID NO | Description |
|---|---|---|
| 12 | 40 | TCR-2 α chain CDR1 |
| 13 | 41 | TCR-2 α chain CDR2 |
| 14 | 42 | TCR-2 α chain CDR3 |
| 15 | 43 | TCR-2 β chain CDR1 |
| 16 | 44 | TCR-2 β chain CDR2 |
| 17 | 45 | TCR-2 β chain CDR3 |
| 20 | 46 | TCR-2 α chain complete |
| 21 | 47 | TCR-2 β chain complete |
| 22 | 48 | TCR-3 α chain CDR1 |
| 23 | 49 | TCR-3 α chain CDR2 |
| 24 | 50 | TCR-3 α chain CDR3 |
| 25 | 51 | TCR-3 β chain CDR1 |
| 26 | 52 | TCR-3 β chain CDR2 |
| 27 | 53 | TCR-3 β chain CDR3 |
| 30 | 54 | TCR-3 α chain complete |
| 31 | 55 | TCR-3 β chain complete |
| 2 | 63 | TCR-4 α chain CDR1 |
| 3 | 64 | TCR-4 α chain CDR2 |
| 4 | 65 | TCR-4 α chain CDR3 |
| 5 | 66 | TCR-4 β chain CDR1 |
| 6 | 67 | TCR-4 β chain CDR2 |
| 7 | 68 | TCR-4 β chain CDR3 |
| 87 | 69 | TCR-4 α chain complete |
| 88 | 70 | TCR-4 β chain complete |
| 12 | 71 | TCR-5 α chain CDR1 |
| 13 | 72 | TCR-5 α chain CDR2 |
| 14 | 73 | TCR-5 α chain CDR3 |
| 15 | 74 | TCR-5 β chain CDR1 |
| 16 | 75 | TCR-5 β chain CDR2 |
| 17 | 76 | TCR-5 β chain CDR3 |
| 89 | 77 | TCR-5 α chain complete |
| 90 | 78 | TCR-5 β chain complete |
| 22 | 79 | TCR-6 α chain CDR1 |
| 23 | 80 | TCR-6 α chain CDR2 |
| 24 | 81 | TCR-6 α chain CDR3 |
| 25 | 82 | TCR-6 β chain CDR1 |
| 26 | 83 | TCR-6 β chain CDR2 |
| 27 | 84 | TCR-6 β chain CDR3 |
| 91 | 85 | TCR-6 α chain complete |
| 92 | 86 | TCR-6 β chain complete |
| 94 | 93 | TCR-4 fusion protein |
| 96 | 95 | TCR-5 fusion protein |
| 98 | 97 | TCR-6 fusion protein |
| 102 | 99 | TCR-7 α chain complete |
| 103 | 100 | TCR-7 β chain complete |
| 104 | 101 | TCR-7 fusion protein |
| 108 | 102 | TCR-8 α chain complete |
| 109 | 103 | TCR-8 β chain complete |
| 110 | 104 | TCR-8 fusion protein |
| 114 | 105 | TCR-9 α chain complete |
| 115 | 106 | TCR-9 β chain complete |
| 116 | 107 | TCR-9 fusion protein |

"Nucleic acid molecule" and "nucleotide sequence" generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. Preferably, the nucleic acids described herein are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acids can be constructed based on chemical synthesis and/or enzymatic ligation reactions using procedures known in the art or commercially available (e.g., from Genscript, Thermo Fisher and similar companies). For example, a nucleic acid can be chemically synthesized (see Sambrook et al.) using naturally occurring nucleotides or variously modified nucleotides designed to increase the biological stability of the molecules or to increase the physical stability of the duplex formed upon hybridization (e.g., phosphorothioate derivatives and acridine-substituted nucleotides). The nucleic acid can comprise any nucleotide sequence which encodes any of the recombinant TCRs, polypeptides, or proteins, or functional portions or functional variants thereof.

The present disclosure also provides variants of the isolated or purified nucleic acids wherein the variant nucleic acids comprise a nucleotide sequence that has at least 75%, 80%, 81%, 82%, 83%, 84%, 85%, 86%, 87%, 88%, 89%, 90%, 91%, 92%, 93%, 94%, 95%, 96%, 97%, 98%, or 99% identical to the nucleotide sequence encoding the TCR described herein. Such variant nucleotide sequence encodes a functional TCR that specifically recognizes MAGE-A4.

The disclosure also provides an isolated or purified nucleic acid comprising a nucleotide sequence, which is complementary to the nucleotide sequence of any of the nucleic acids described herein or a nucleotide sequence which hybridizes under stringent conditions to the nucleotide sequence of any of the nucleic acids described herein.

The nucleotide sequence, which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand and are particularly suitable for detecting expression of any of the TCRs described herein. It is generally appreciated that conditions can be rendered more stringent by the addition of increasing amounts of formamide.

In particular embodiments, nucleic acids are codon optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

Another embodiment refers to a vector comprising the nucleic acid encoding the TCR as described herein. The vector is preferably a plasmid, shuttle vector, phagemid, cosmid, expression vector, retroviral vector, adenoviral vector or particle and/or vector to be used in gene therapy.

A "vector" is any molecule or composition that has the ability to carry a nucleic acid sequence into a suitable host cell where synthesis of the encoded polypeptide can take place. Typically, and preferably, a vector is a nucleic acid that has been engineered, using recombinant DNA techniques that are known in the art, to incorporate a desired nucleic acid sequence. The vector may comprise DNA or RNA and/or comprise liposomes. The vector may be a plasmid, shuttle vector, phagemid, cosmid, expression vector, retroviral vector, lentiviral vector, adenoviral vector or particle and/or vector to be used in gene therapy. A vector may include nucleic acid sequences that permit it to replicate in a host cell, such as an origin of replication. A vector may also include one or more selectable marker genes and other genetic elements known to those of ordinary skill in the art. A vector preferably is an expression vector that includes a nucleic acid according to the present invention operably linked to sequences allowing for the expression of said nucleic acid.

In preferred embodiments, a vector comprises a nucleic acid encoding a TCR β chain having an amino acid sequence set forth in SEQ ID NO: 88 and a TCR α chain having an amino acid sequence set forth in SEQ ID NO: 87; a TCR β chain having an amino acid sequence set forth in SEQ ID NO: 90 and a TCR α chain having an amino acid sequence set forth in SEQ ID NO: 89; a TCR β chain having an amino acid sequence set forth in SEQ ID NO: 92 and a TCR α chain having an amino acid sequence set forth in SEQ ID NO: 91; a TCR β chain having an amino acid sequence set forth in SEQ ID NO: 103 and a TCR α chain having an amino acid sequence set forth in SEQ ID NO: 102; a TCR β chain having an amino acid sequence set forth in SEQ ID NO: 109 and a TCR α chain having an amino acid sequence set forth in SEQ ID NO: 108; or a TCR β chain having an amino acid sequence set forth in SEQ ID NO: 115 and a TCR α chain having an amino acid sequence set forth in SEQ ID NO: 114.

Preferably, the vector is an expression vector. More preferably, the vector is a retroviral, more specifically a gamma-retroviral or lentiviral vector.

I. Cells, Cell Lines

Another aspect refers to a cell expressing the TCR as described herein. In some embodiments, the cell is isolated or non-naturally occurring. In specific embodiments, the cell may comprise the nucleic acid encoding the TCR as described herein or the vector comprising said nucleic acid.

In the cell, the above described vector comprising a nucleic acid sequence coding for the above described TCR may be introduced or ivtRNA coding for said TCR may be introduced. The cell may be a peripheral blood lymphocyte such as a T cell. The method of cloning and exogenous expression of the TCR is for example described in Engels et al. *Cancer Cell*, 2013; 23(4): 516-526. The transduction of primary human T cells with a lentiviral vector is, for example, described in Cribbs et al. *BMC Biotechnol.* 2013; 13: 98.

The term "transfection" refers to a non-viral process by which an exogenous nucleic acid sequence is introduced in a host cell, e.g., in an eukaryotic host cell. It is noted that introduction or transfer of nucleic acid sequences is not limited to the mentioned methods but can be achieved by any number of means including electroporation, microinjection, gene gun delivery, lipofection, or superfection.

The term "transduction" refers to the introduction of an exogenous nucleic acid sequence into a host cell using a viral vector, e.g., an adenovirus, an adeno-associated virus (AAV), a vaccinia virus, a herpes virus, a retrovirus, or lentivirus.

Some embodiments refer to a cell comprising: a) an expression vector which comprises at least one nucleic acid as described herein, or b) a first expression vector which comprises a nucleic acid encoding the alpha chain of the TCR as described herein, and a second expression vector which comprises a nucleic acid encoding the beta chain of a TCR as described herein.

In some embodiments, the cell is a peripheral blood lymphocyte (PBL) or a peripheral blood mononuclear cell (PBMC). The cell may be a natural killer (NK) cell, natural killer like T (NKT) cell or a T cell. Preferably, the cell is a T cell. The T cell may be a $CD4^+$ or a $CD8^+$ T cell or double negative T cells, i.e., T cells expressing neither CD4 or CD8. In some embodiments, the cell is a stem cell like memory T cell.

In preferred embodiments, the TCR functions independently of co-receptors, i.e., the TCR is function in both $CD8^+$ and $CD4^+$ cells, e.g., TCR-5 and TCR-8.

Stem cell-like memory T cells (TSCM) are a less-differentiated subpopulation of $CD8^+$ T cells, which are characterized by the capacity of self-renewal and to persist long-term. Once these cells encounter their antigen in vivo, they differentiate further into central memory T cells (TCM), effector memory T cells (TEM) and terminally differentiated effector memory T cells (TEMRA) with some TSCM remaining quiescent (Flynn et al., *Clinical & Translational Immunology* 2014; 3(7): e20). These remaining TSCM cells show the capacity to build a durable immunological memory in vivo and therefore are considered an important T cell subpopulation for adoptive T cell therapy (Lugli et al., *Nature Protocols* 2013; 8: 33-42, Gattinoni et al., *Nat. Med.* 2011; October; 17(10): 1290-1297). Immune-magnetic selection can be used in order to restrict the T cell pool to the stem cell memory T cell subtype see (Riddell et al. *Cancer Journal* 2014; 20(2): 141-144)

J. Antibodies Targeting TCR

Another aspect refers to an antibody or antigen-binding fragment thereof specifically binding to a portion of the TCR as described herein that mediates specificity for MAGE-A4. In one embodiment, the portion of the TCR that mediates the MAGE-A4 specificity comprises the CDR3 of the TCR alpha chain selected from the group consisting of SEQ ID NO: 4, SEQ ID NO: 14 and SEQ ID NO:24 and the CDR3 of the beta chain selected from the group consisting of SEQ ID NO: 7, SEQ ID NO: 17 or SEQ ID NO: 27.

The antibody or antigen-binding fragment thereof may modulate the activity of the TCR. It may block or may not block the binding of the TCR with MAGE-A4. It could be used for modulating the therapeutic activity of the TCR or for diagnostic purposes.

K. Pharmaceutical Compositions, Medical Treatments and Kits

Another aspect refers to compositions comprising the TCR as described herein, the polypeptide comprising a functional portion of said TCR, the multivalent TCR complex as described herein, the nucleic acid encoding the TCR, the vector comprising said nucleic acid, the cell comprising said TCR, or the antibody specifically binding to a portion of the TCR as described herein.

Another aspect refers to pharmaceutical compositions comprising the TCR as described herein, the polypeptide comprising a functional portion of said TCR, the multivalent TCR complex as described herein, the nucleic acid encoding the TCR, the vector comprising said nucleic acid, the cell comprising said TCR, or the antibody specifically binding to a portion of the TCR as described herein.

Those active components of the present invention are preferably used in such a pharmaceutical composition, in doses mixed with an acceptable carrier or carrier material, that the disease can be treated or at least alleviated. Such a composition can (in addition to the active component and the carrier) include filling material, salts, buffer, stabilizers, solubilizers and other materials, which are known state of the art.

The term "pharmaceutically acceptable" defines a non-toxic material, which does not interfere with effectiveness of the biological activity of the active component. The choice of the carrier is dependent on the application.

The pharmaceutical composition may contain additional components which enhance the activity of the active component or which supplement the treatment. Such additional components and/or factors can be part of the pharmaceutical composition to achieve synergistic effects or to minimize adverse or unwanted effects.

Techniques for the formulation or preparation and application/medication of active components of the present invention are published in *Remington: The Science and Practice of Pharmacy*, volume I and volume II $22^{nd}$ Edition. Edited by Loyd V. Allen Jr. Philadelphia, PA: Pharmaceutical Press; 2012, which is incorporated by reference herein, in its entirety. An appropriate application is a parenteral application, for example intramuscular, subcutaneous, intramedullar injections as well as intrathecal, direct intraventricular, intravenous, intranodal, intraperitoneal or intratumoral injections. The intravenous injection or infusion is the preferred treatment of a patient.

According to a preferred embodiment, the pharmaceutical composition is administered by an infusion or an injection. An injectable composition is a pharmaceutically acceptable fluid composition comprising at least one active ingredient, e.g., an expanded T cell population (for example autologous or allogenic to the patient to be treated) expressing a TCR. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this disclosure are conventional; appropriate formulations are well known to those of ordinary skill in the art.

Typically, the pharmaceutical composition comprises at least one pharmaceutically acceptable carrier.

Accordingly, another aspect refers to the TCR as described herein, the polypeptide comprising a functional portion of said TCR, the multivalent TCR complex according as described herein, the nucleic acid encoding said TCR, the vector comprising said nucleic acid, the cell comprising said TCR, the antibody specifically binding to a portion of the TCR, a composition or pharmaceutical composition comprising one or more cells expressing the TCR as described herein for use as a medicament.

Some embodiments refer to the TCR as described herein, the polypeptide comprising a functional portion of said TCR, the multivalent TCR complex according as described herein, the nucleic acid encoding said TCR, the vector comprising said nucleic acid, the cell comprising said TCR, or compositions or pharmaceutical compositions comprising the same for use in the treatment of cancer.

In one embodiment, the cancer is a hematological cancer or a solid tumor. Hematological cancers also called blood cancers, which do not form solid tumors and therefore are dispersed in the body. Examples of hematological cancers are leukemia, lymphoma or multiple myeloma. There are two major types of solid tumors, sarcomas and carcinomas. Sarcomas are for example tumors of the blood vessel, bone, fat tissue, ligament, lymph vessel, muscle or tendon.

In one embodiment, the cancer is selected from the group consisting of sarcoma, prostate cancer, uterine cancer, thyroid cancer, testicular cancer, renal cancer, pancreatic cancer, ovarian cancer, esophageal cancer, non-small-cell lung cancer, (NSCLC) small-cell lung cancer (SCLC), non-Hodgkin's lymphoma, multiple myeloma, melanoma, hepatocellular carcinoma, head and neck cancer, gastric cancer, endometrial cancer, colorectal cancer, cholangiocarcinoma, breast cancer, bladder cancer, myeloid leukemia and acute lymphoblastic leukemia. Preferably, the cancer is selected from the group consisting of NSCLC, SCLC, breast, ovarian or colorectal cancer, or sarcoma. More preferably, the cancer is selected from urothelial (bladder) cancers, melanoma, head and neck cancer, ovarian cancer, NSCLC, esophageal cancer, gastric cancers, synovial sarcoma, and Myxoid Round Cell Liposarcoma (MRCLS).

In one embodiment, the TCR recognize lung cancer cell lines, such as the NSCLC cell line NCI-H1703 and the liver metastases cell line of NSCLC, NCI-H1755.

Also contemplated herein are pharmaceutical compositions and kits containing one or more of (i) an isolated TCR as described herein; (ii) viral particles comprising a nucleic acid encoding a recombinant TCR; (iii) immune cells, such as T cells or NK cells, modified to express a recombinant TCR as described herein; (iv) nucleic acids encoding a recombinant TCR as described herein. In some embodiments, the present disclosure provides compositions comprising lentiviral vector particles comprising a nucleotide sequence encoding a recombinant TCR described herein (or T cells that have been modified using the vector particles described herein to express a recombinant TCR). Such compositions can be administered to subjects in the methods of the present disclosure as described further herein.

Compositions comprising the modified T cells as described herein can be utilized in methods and compositions for adoptive immunotherapy in accordance with known techniques, or variations thereof that will be apparent to those skilled in the art based on the instant disclosure.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

The number of cells for an effective treatment in the composition is typically greater than 10 cells, and up to $10^6$, up to and including $10^8$ or $10^9$ cells and can be more than $10^{10}$ cells. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 ml or less, even 250 ml or 100 ml or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^9$, $10^{10}$ or $10^{11}$ cells.

Pharmaceutical compositions provided herein can be in various forms, e.g., in solid, liquid, powder, aqueous, or lyophilized form. Examples of suitable pharmaceutical carriers are known in the art. Such carriers and/or additives can be formulated by conventional methods and can be administered to the subject at a suitable dose. Stabilizing agents such as lipids, nuclease inhibitors, polymers, and chelating agents can preserve the compositions from degradation within the body. In a composition intended to be administered by injection, one or more of a surfactant, preservative, wetting agent, dispersing agent, suspending agent, buffer, stabilizer and isotonic agent may be included.

The recombinant TCRs as described herein, or the viral vector particles comprising a nucleotide sequence encoding a recombinant TCR provided herein, can be packaged as kits. Kits can optionally include one or more components such as instructions for use, devices, and additional reagents, and components, such as tubes, containers and syringes for practice of the methods. Exemplary kits can include the nucleic acids encoding the recombinant TCRs, the recombinant TCR polypeptides, or viruses provided herein, and can optionally include instructions for use, a device for detecting a virus in a subject, a device for administering the compositions to a subject, and a device for administering the compositions to a subject.

Kits comprising polynucleotides encoding a gene of interest (e.g., a recombinant TCR) are also contemplated herein. Kits comprising a viral vector encoding a sequence of interest (e.g., a recombinant TCR) and optionally, a polynucleotide sequence encoding an immune checkpoint inhibitor are also contemplated herein.

Kits contemplated herein also include kits for carrying out the methods for detecting the presence of polynucleotides encoding any one or more of the TCRs disclosed herein. In particular, such diagnostic kits may include sets of appropriate amplification and detection primers and other associated reagents for performing deep sequencing to detect the polynucleotides encoding TCRs disclosed herein. In further embodiments, the kits herein may comprise reagents for detecting the TCRs disclosed herein, such as antibodies or other binding molecules. Diagnostic kits may also contain instructions for determining the presence of the polynucleotides encoding the TCRs disclosed herein or for determining the presence of the TCRs disclosed herein. A kit may also contain instructions. Instructions typically include a tangible expression describing the components included in the kit, and methods for administration, including methods for determining the proper state of the subject, the proper dosage amount, and the proper administration method. Instructions can also include guidance for monitoring the subject over the duration of the treatment time.

Kits provided herein also can include a device for administering a composition described herein to a subject. Any of a variety of devices known in the art for administering medications or vaccines can be included in the kits provided herein. Exemplary devices include, but are not limited to, a hypodermic needle, an intravenous needle, a catheter, a needle-less injection device, an inhaler, and a liquid dispenser, such as an eyedropper. Typically, the device for administering a virus of the kit will be compatible with the virus of the kit; for example, a needle-less injection device such as a high-pressure injection device can be included in kits with viruses not damaged by high-pressure injection, but is typically not included in kits with viruses damaged by high pressure injection.

Kits provided herein also can include a device for administering a compound, such as a T cell activator or stimulator, or a TLR agonist, such as a TLR4 agonist to a subject. Any of a variety of devices known in the art for administering medications to a subject can be included in the kits provided herein. Exemplary devices include a hypodermic needle, an intravenous needle, a catheter, a needle-less injection, but are not limited to, a hypodermic needle, an intravenous needle, a catheter, a needle-less injection device, an inhaler, and a liquid dispenser such as an eyedropper. Typically, the device for administering the compound of the kit will be compatible with the desired method of administration of the compound.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intrarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II 22$^{nd}$ Edition. Edited by Loyd V. Allen Jr. Philadelphia, PA: Pharmaceutical Press; 2012, which is incorporated by reference herein, in its entirety.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

MAGE-A4-TCR-Transgenic T Cells Bind MAGE-A4$_{GVY}$-MHC-Multimers

An in vitro priming approach was used to isolate MAGE-A4-reactive T-cell clones. The priming system used mature dendritic cells (mDCs) of HLA-A*02:01-positive as well as HLA-A*02:01-negative donors as antigen-presenting cells and autologous CD8$^{+}$-enriched T cells as responding cells. In vitro transcribed RNA (ivtRNA) encoding the human MAGEA4 gene served as the source of specific antigen. After electroporation into the mDCs, the MAGE-A4-encoding ivtRNA was translated into protein, and subsequently processed and presented as peptides by HLA-A*02:01 encoded molecules on the mDCs. For HLA-A*02:01-negative donors, ivtRNA coding for HLA-A*02:01 was used in addition to MAGE-A4 ivtRNA to transgenically express the respective HLA allele in the antigen-presenting cells (allogeneic approach). In vitro co-cultures of T cells with the ivtRNA-transfected mDCs from the same donor lead to de novo induction of antigen-specific T cells that served as the source of corresponding TCRs. Antigen-specific T cells can be enriched by a variety of methods and are cloned by limiting dilution or FACS-based single cell sorting. Sequences of TCR alpha and TCR beta chains of MAGE-A4-reactive T-cell clones were identified by Next Generation Sequencing and after exchanging the constant TCR regions by their murine counterparts cloned into the retroviral vector pES.12-6. PBMCs of a healthy donor were isolated by ficoll gradient centrifugation. CD8$^{+}$ T-cells were enriched by negative magnetic selection (Miltenyi) and stimulated in non-tissue culture 24-well plates, pre-coated with anti-CD3 (5 µg/ml) and anti-CD28 (1 µg/ml) mAb (BD Pharmingen, Heidelberg, Germany). Amphotropic retroviral particles were produced by transfection of HEK293T cells with the respective TCR encoding retroviral plasmid and two expression plasmids. On day two after stimulation, CD8$^{+}$ T cells were transduced and on day twelve enriched for transduced CD8$^{+}$ cells by FACS using the murine constant beta region as a marker for transduction and then expanded by rapid expansion protocol (Riddell S R, *Science*, 1992 Jul. 10; 257(5067):238-41).

In the experiments described in Examples 2-5, TCRs containing murinized Cα and Cβ regions were used (i.e., TCR-1 comprising the α chain of SEQ ID NO:57 and the β chain of SEQ ID NO:58, TCR-2 comprising the α chain of SEQ ID NO:59 and the β chain of SEQ ID NO:60, TCR-3 comprising the α chain of SEQ ID NO:61 and the β chain of SEQ ID NO:62). The same types of experiments described in examples 2-5 could also be carried out using TCRs containing minimal murinized Cα and Cβ regions as described above.

Results:

CD8$^{+}$ T cells were transduced with three different TCRs isolated from MAGE-A4-reactive T-cell clones and one control TCR that did not recognize MAGE-A4. They were stained with a MAGE-A4$_{GVY}$-MHC-multimer (MAGE-A4$^{230\text{-}239}$, GVYDGREHTV; immuneAware) and antibodies against CD8 and the murine constant beta region. All MAGE-A4-TCR-transgenic T cell populations bound the MAGE-A4$_{GVY}$-MHC-multimer very efficiently (>70%). No MAGE-A4$_{GVY}$-MHC-multimer-staining was observed with the control TCR. These results show that TCRs isolated from MAGE-A4-reactive T-cell clones can be transgenically expressed in T cells of a healthy donor (FIG. 1).

Example 2

MAGE-A4-TCR-Transgenic T Cells Recognize MAGE-A4$_{GVY}$-Peptide

MAGE-A4 specificity of TCR-transgenic T cells was confirmed according to the following protocol:

As target cells, T2 cells (HLA-A*02pos) were loaded with saturating amounts ($10^{-5}$ M) of MAGE-A4$_{GVY}$-peptide (SEQ ID NO: 1) or an irrelevant control peptide. In addition, K562 cells were transduced with HLA-A*02:01 and the MAGE-A4 gene (K562/A2/MAGE-A4). K562 cells transduced only with HLA-A*02:01 were used as a control (K562/A2). Each target cell line was co-cultured with TCR-transgenic T cells at a ratio of 2:1 using 20,000 T cells and 10,000 target cells. After 20-24 h, IFN-γ concentrations in co-culture supernatants were analyzed by standard sandwich ELISA (BD human IFN-γ ELISA set).

Figure 2:
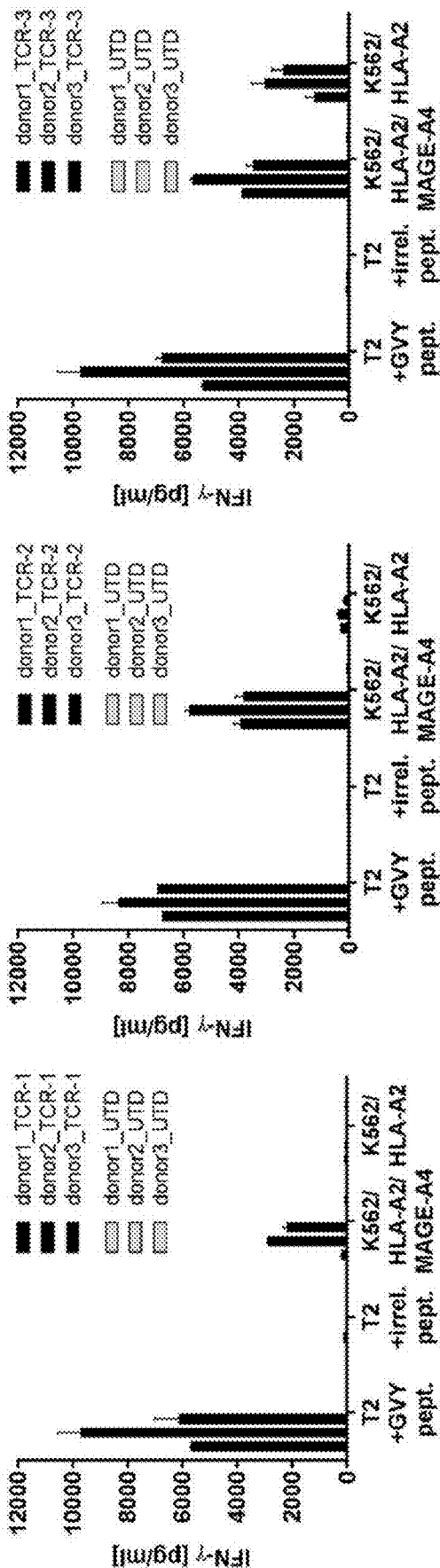
FIG. 2 shows that MAGE-A4-TCR-transgenic T cells recognize MAGE-A4$_{GVY}$-peptide presented on HLA-A2. Transgenic T cells were co-cultured with T2 cells externally loaded with MAGE-A4$_{GVY}$-peptide or K562/HLA-A2 cells that had been transduced with the MAGE-A4 gene. As negative controls, T2 cells loaded with a control peptide and untransduced K562/HLA-A2 cells were used, respectively. Recognition of target cells was analyzed by measuring the IFN-γ concentration in co-culture supernatants by a standard ELISA.

Results:

MAGE-A4-TCR-transgenic T cells recognized MAGE-A4$_{GVY}$-loaded T2 and MAGE-A4-transduced K562 cells but none of the control target cells. TCR-3-transduced T cells showed recognition of the K562/A2 control. These results show that TCRs isolated from MAGE-A4-reactive T-cell clones are functional when transferred to T cells of a healthy donor (FIG. 2).

Example 3

MAGE-A4-TCR-Transgenic T Cells Show High Functional Avidity

T2 cells loaded with MAGE-A4$_{GVY}$-peptide were used to analyze differences in the functional avidity of MAGE-A4-TCR-transgenic T cells:

T2 cells were externally loaded with graded concentrations ($10^{-11}$ M-$10^{-5}$ M) of the MAGE-A4$_{GVY}$-peptide and co-cultured with TCR-transgenic T cells at a ratio of 1:2 using 10,000 T2 cells and 20,000 T cells. After 20-24 h, IFN-γ concentrations in co-culture supernatants were analyzed by standard sandwich ELISA (BD human IFN-γ ELISA set).

Figure 3:
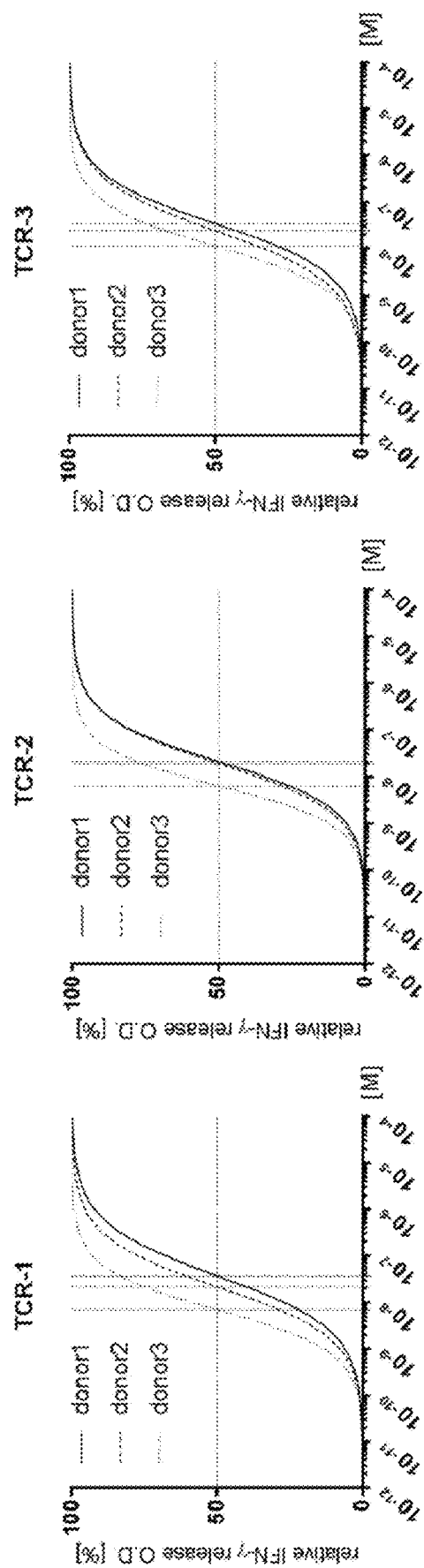
FIG. 3 shows the functional avidity of MAGE-A4-TCR-transgenic T cells. Transgenic T cells were co-cultured with T2 cells externally loaded with graded concentrations of MAGE-A4$_{GVY}$-peptide (10-12 M-10-4 M). IFN-γ concentration in co-culture supernatants was measured by a standard ELISA.

Results:

Integrated over multiple donors, the highest functional avidity against MAGE-A4$_{GVY}$-peptide loaded on HLA-A*02 was shown by TCR-2. TCR-1 and TCR-3 showed slightly reduced functional avidity compared to TCR-2 (FIG. 3).

Example 4

MAGE-A4-TCR-Transgenic T Cells Lyse MAGE-A4-Positive Tumor Cell Lines

MAGE-A4-positive HLA-A2-positive tumor cell lines (NCI-H1703, NCI-H1755), a MAGE-A4-negative HLA-A2-positive tumor cell line (Saos-2) and a MAGE-A4-negative HLA-A2-negative tumor cell line (A549) were used as target cells. For cytotoxicity assays, the co-cultures were set-up at an effector-to-target ratio of about 8-16:1 (depending on the target cell size), with 40,000 TCR-transgenic T cells and 5,000 (NCI-H1755, NCI-H1703, A549) and 2,500 (Saos-2) tumor cells respectively, that have been transduced with a fluorescent marker gene. Tumor cells loaded with saturated concentrations of MAGE-A4$_{GVY}$-peptide ($10^{-5}$ M) were used as internal positive control. The decrease of fluorescent target cells (cell count per well) was measured every three hours over a total time period of 172 hours using live-cell monitoring (IncuCyte® ZOOM, Essen Bioscience). To analyze cytokine release, co-culture supernatants were harvested after 24 h and respective IFN-γ concentrations were analyzed by standard sandwich ELISA (BD human IFN-γ ELISA set).

Figure 4A:
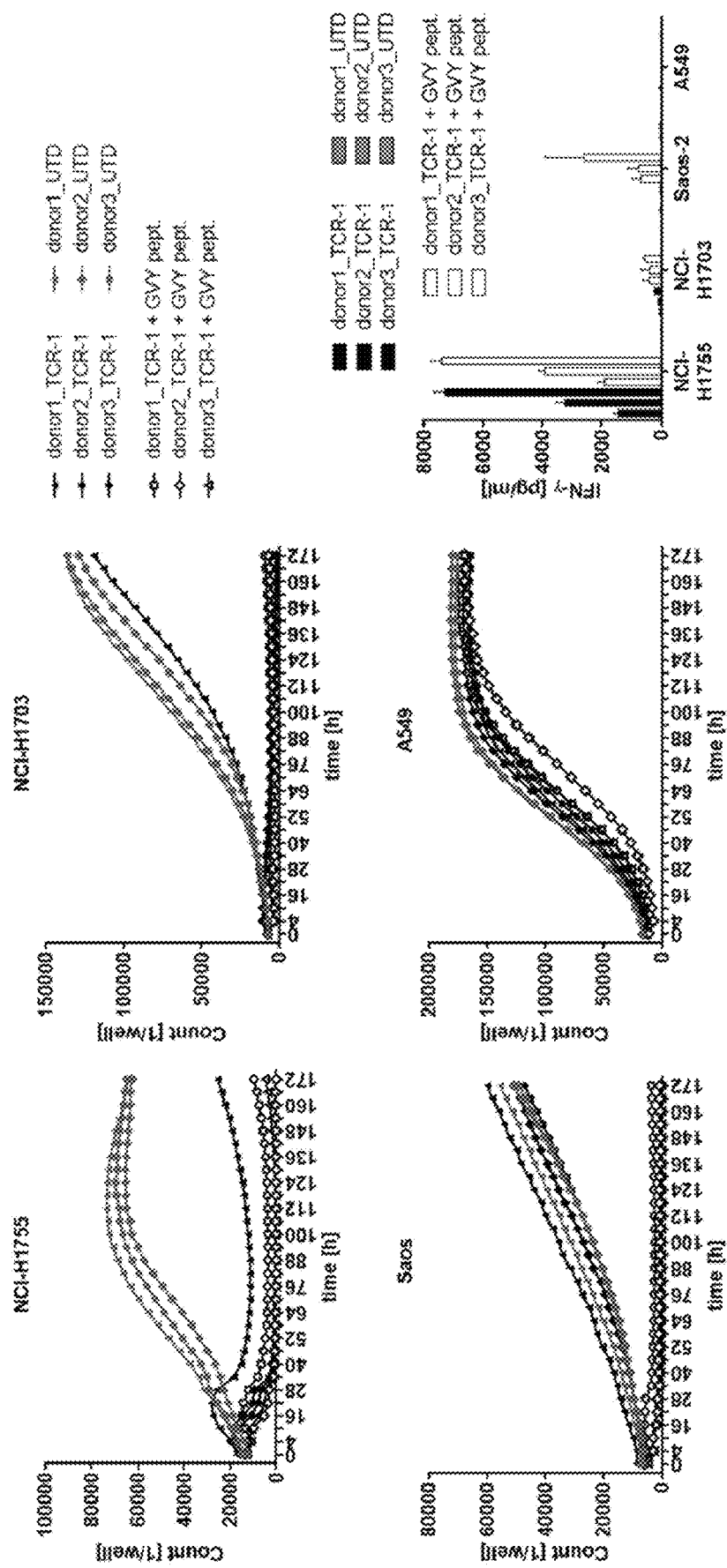
FIGS. 4A-C show the ability of MAGE-A4-TCR-transgenic T cells (TCR-1, TCR-2 and TCR-3) to lyse MAGE-A4-positive tumor cell lines in a HLA-A2-dependent manner. Transgenic T cells were co-cultured with different MAGE-A4-positive HLA-A2-positive tumor cell lines (NCI-H1703, NCI-H1755), a MAGE-A4-negative HLA-A2-positive tumor cell line (Saos-2) and a MAGE-A4-negative HLA-A2-negative tumor cell line (A549). Tumor cells loaded with MAGE-A4$_{GVY}$-peptide are used as positive control. Cytotoxicity against the tumor cell lines stably transduced with a fluorescence marker was measured with an IncuCyte® ZOOM device (Essen Bioscience) by taking pictures every two hours. To analyze cytokine release, co-culture supernatants were harvested after 24 hrs. and IFN-γ concentrations analyzed by standard sandwich ELISA (BD human IFN-γ ELISA set).
Figure 4B:
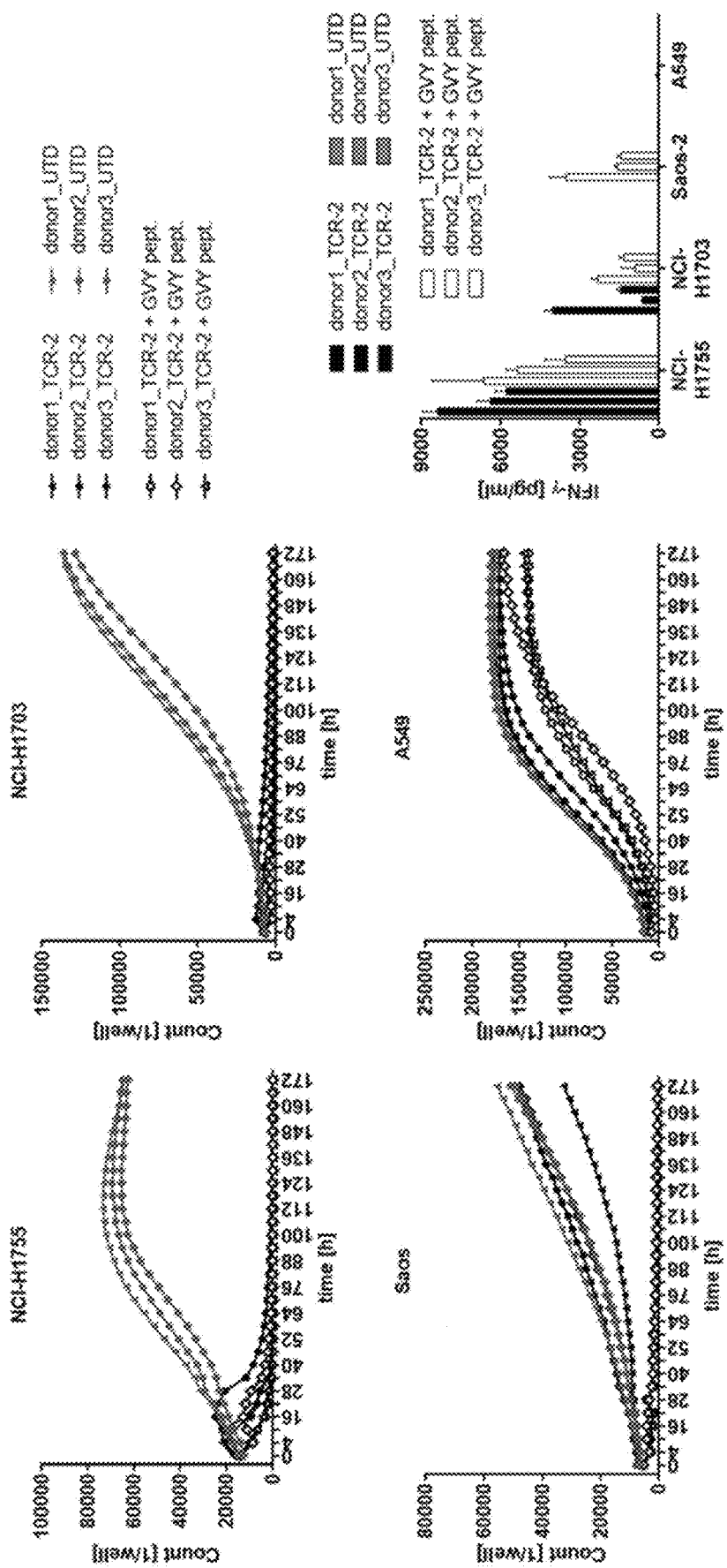
Figure 4C:
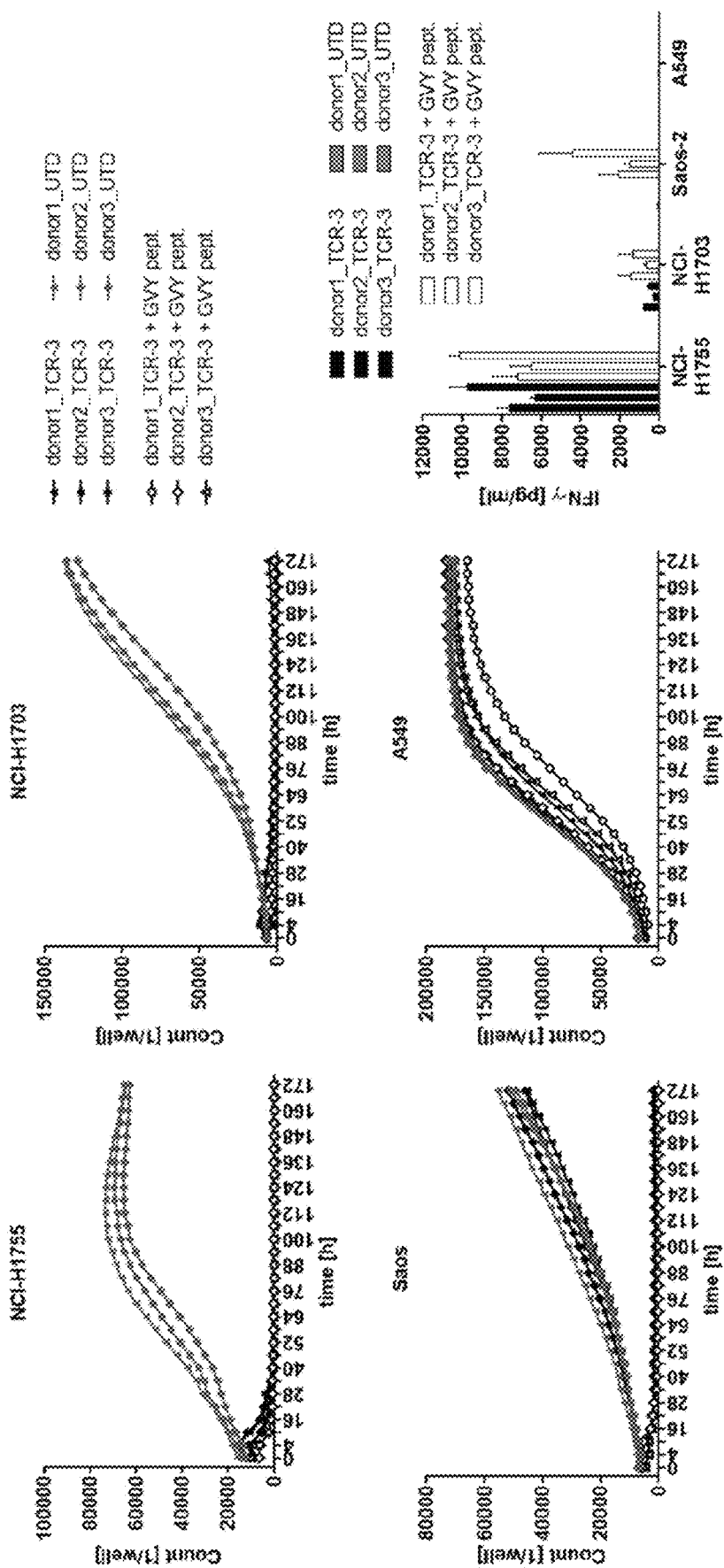

Results:

The two endogenously MAGE-A4-positive HLA-A2 positive tumor cell lines (NCI-H1703, NCI-H1755) were recognized and lysed by all MAGE-A4-TCR-transgenic T cells. The MAGE-A4-negative but HLA-A2 positive tumor cell line (Saos-2) was only recognized and lysed when the cells were externally loaded with saturated concentrations of MAGE-A4$_{GVY}$-peptide. The negative control cell line (A549) was neither recognized nor lysed by one of the MAGE-A4-TCRs. These results show that MAGE-A4-TCR-transgenic T cells can efficiently lyse endogenously MAGE-A4-positive tumor cells in a highly selective manner (FIGS. 4a, 4b and 4c).

Example 5

MAGE-A4-TCR-Transgenic T Cells do not Recognize Normal Human Cells

A panel of normal human cells was used to analyze potential on-target/off-tumor and off-target toxicities that could be caused by MAGE-A4-TCR-transgenic T cells.

Primary cells and induced pluripotent stem cell (iPS)-derived cells representing essential tissues or organs were tested for recognition by MAGE-A4-TCR-transduced T cells. HLA-A*02:01-negative NHBE cells were transfected with HLA-A2-ivtRNA via electroporation to transiently express HLA-A2. iCell Neurons were treated with IFN-γ for 72 h prior to start of the co-culture to induce cell surface HLA-A2 expression. HLA-A2 expression of all cell types was confirmed via flow cytometry. For toxicity assays, co-cultures were set-up with 20,000 TCR transgenic T cells and cell type specific amounts of target cells. As an internal positive control, all normal human cells were loaded with a final concentration of $10^5$ M of MAGE-A4$_{GVY}$-peptide. To analyze cytokine release, co-culture supernatants were harvested after 24 h and IFN-γ or IL-2 concentrations were analyzed by standard sandwich ELISA (BD human IFN-γ or IL-2 ELISA set). IL-2 release was determined for co-culture with iCell Neurons, which have been pre-treated with IFN-γ to induce HLA-A2 surface expression.

Figure 5A:
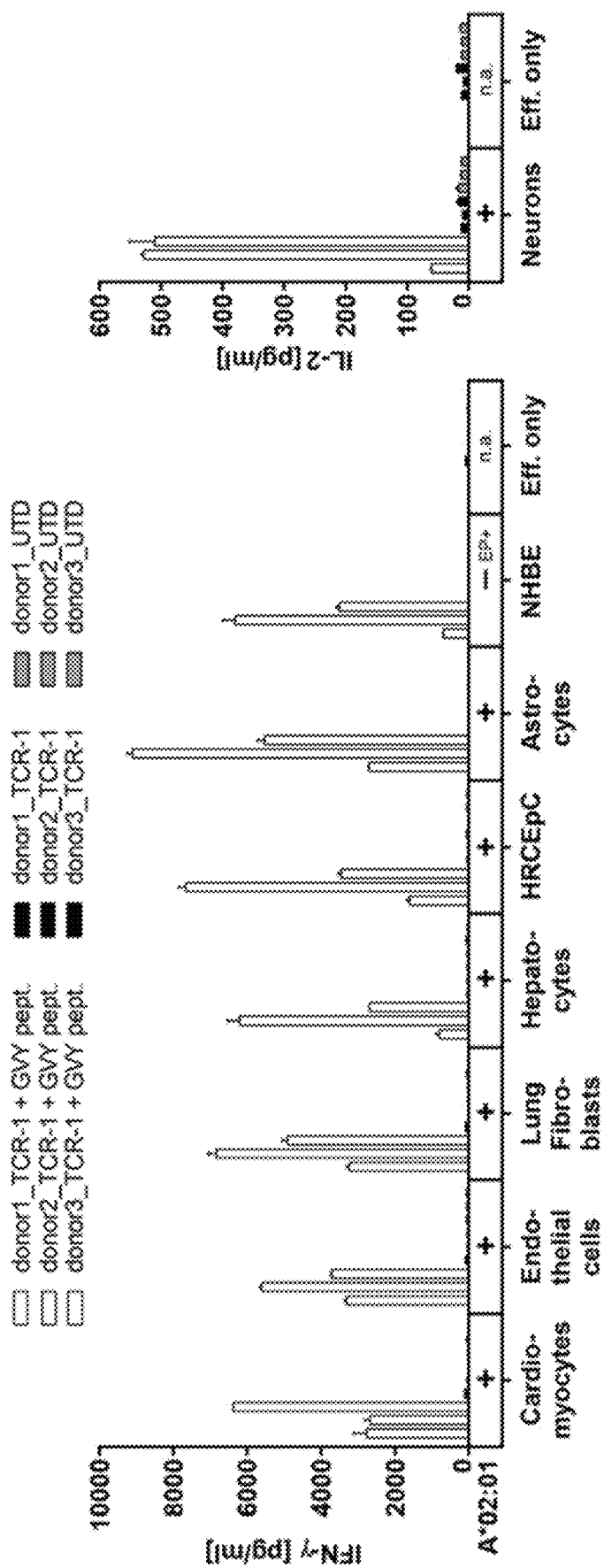
FIGS. 5A-C show that MAGE-A4-TCR-transgenic T cells (TCR-1, TCR-2 and TCR-3) do not recognize normal human cells. Transgenic T cells were co-cultured with different primary cells and induced pluripotent stem cell (iPS)-derived cells representing essential tissues or organs. Normal cells loaded with MAGE-A4$_{GVY}$-peptide are used as positive control. HLA-A2 expression was induced on neurons by pre-incubation with IFN-γ. The HLA-A2-negative NHBE cells were electroporated with HLA-A2-ivtRNA and HLA-A2 expression of all cells was confirmed via flow cytometry. To analyze cytokine release, co-culture supernatants were harvested after 24 h and IFN-γ as well as IL-2 concentrations were analyzed by standard sandwich ELISA (BD human IFN-γ or IL-2 ELISA set).
Figure 5B:
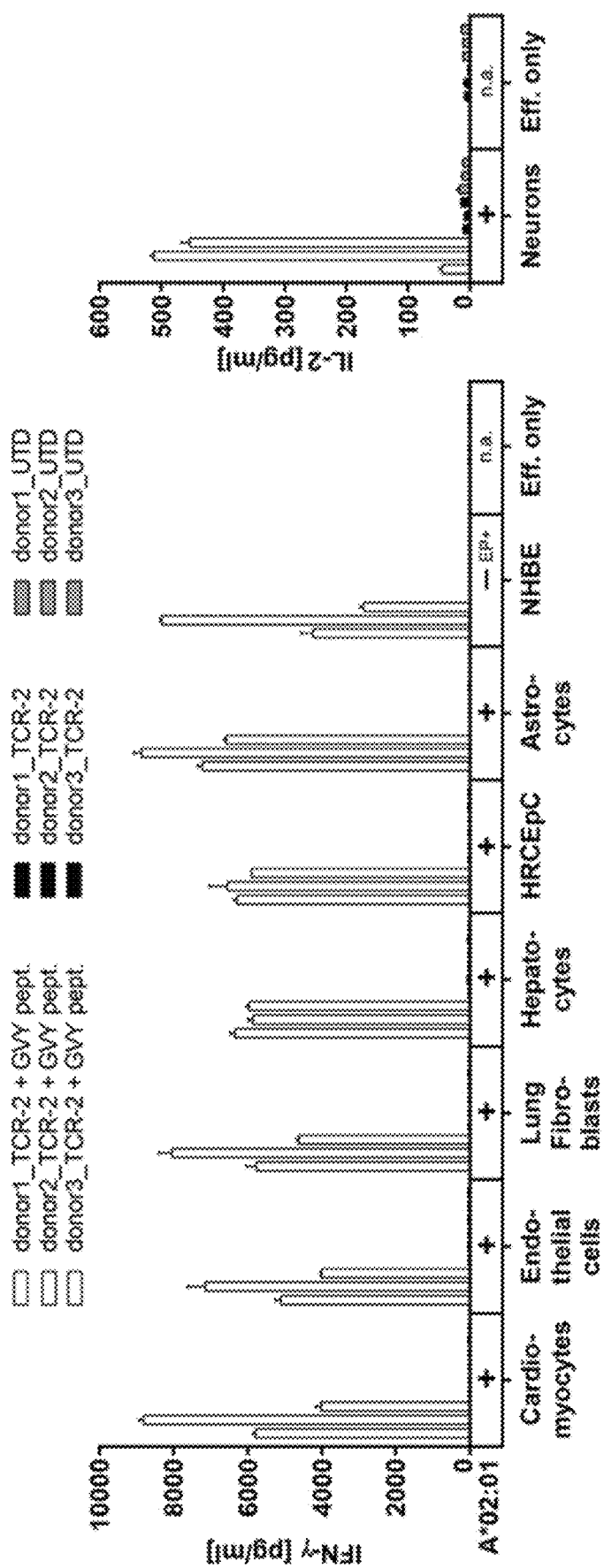
Figure 5C:
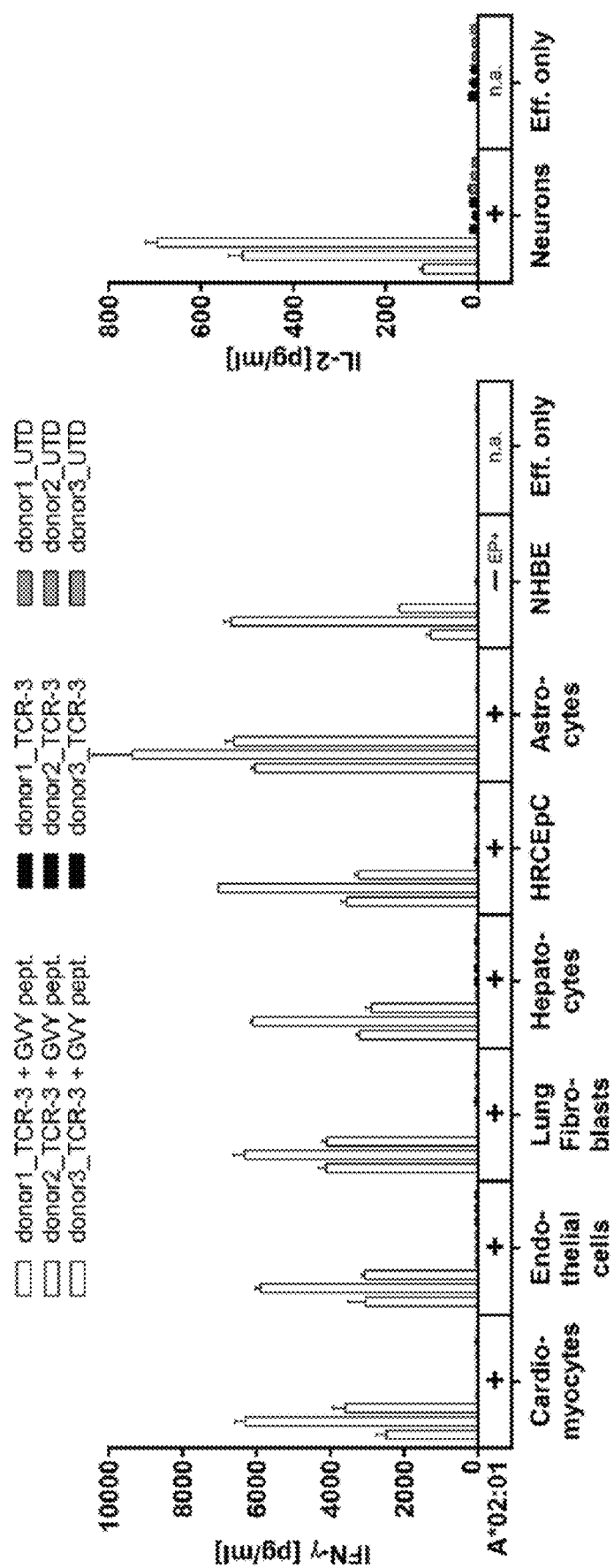

Results:

All primary cells and induced pluripotent stem cell (iPS)-derived cells were HLA-A2 positive at the beginning of co-cultivation with the MAGE-A4-TCR-transgenic T cells. Furthermore, the MAGE-A4-TCR-transgenic T cells were able to efficiently recognize all normal cells, when the individual target cells were loaded with the MAGE-A4$_{GVY}$-peptide. Unloaded normal cells were not recognized by any of the MAGE-A4-transgenic T cells. The MAGE-A4-transgenic T cells show no sign of on-target/off-tumor and off-target toxicities (FIGS. 5a, 5b and 5c).

Example 6

Lentiviral Vectors Encoding Fully Human MAGE-A4 TCRs

The TCR polynucleotide sequences identified in Example 1 were optimized for expression. Lentiviral vectors encoding polycistronic TCR constructs were used to express the TCRs. The polycistronic TCR constructs contain a TCR α or β chain, an optional furin cleavage site, a P2A ribosomal skipping sequence, and the corresponding TCR α or β chain. Lentiviral vectors were produced according to known methods. See e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot.2009.22.

The polycistronic polynucleotide (SEQ ID NO: 93) encoding the MAGE-A4 TCR-4 polyprotein (SEQ ID NO: 94) contains a β chain encoded by SEQ ID NO: 70, a polynucleotide encoding a ribosomal skip sequence, and an α chain encoded by SEQ ID NO: 69.

The polycistronic polynucleotide (SEQ ID NO: 95) encoding the MAGE-A4 TCR-5 polyprotein (SEQ ID NO: 96) contains a β chain encoded by SEQ ID NO: 78, a polynucleotide encoding a furin cleavage site, a polynucleotide encoding a ribosomal skip sequence, and an α chain encoded by SEQ ID NO: 77.

The polycistronic polynucleotide (SEQ ID NO: 97) encoding the MAGE-A4 TCR-6 polyprotein (SEQ ID NO: 98) contains a β chain encoded by SEQ ID NO: 86, a polynucleotide encoding a furin cleavage site, a polynucleotide encoding a ribosomal skip sequence, and an α chain encoded by SEQ ID NO: 85.

Example 7

T Cells Expressing MAGE-A4 Fully Human TCRs Bind MAGE-A4$_{GVY}$-MHC-Multimers

Figure 6:
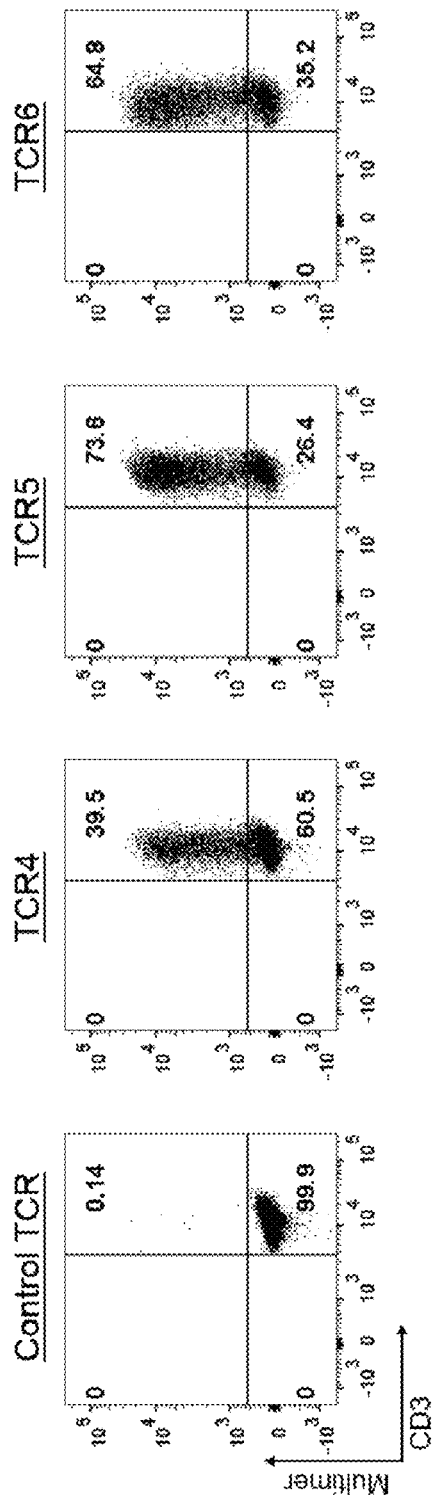
FIG. 6 shows the MAGE-A4$_{GVY}$-MHC-multimer binding of CD3+ T cells transduced with different MAGE-A4-reactive fully human TCRs. CD3+ T cells were isolated from PBMCs of a healthy donor and transduced with three different MAGE-A4-TCRs and one control TCR that did not recognize MAGE-A4. After expansion of these cells, they were stained with a MAGE-A4$_{GVY}$-MHC-multimer and antibody against CD3 and analyzed by flow cytometry. Populations were gated on live CD3+ cells and multimer staining.

CD3$^+$ T cells were isolated from PBMCs of a healthy donor and transduced with lentiviral vectors encoding three different full human MAGE-A4 TCRs and a control TCR that did not recognize MAGE-A4. After expansion, the transduced T cells were stained with a MAGE-A4$_{GVY}$-MHC-multimer (MAGE-A4$^{230-239}$, GVYDGREHTV; immuneAware) and antibodies against CD3. Populations were gated on live CD3$^+$ cells and multimer staining. All MAGE-A4-TCR-transgenic T cell populations bound the MAGE-A4$_{GVY}$-MHC-multimer very efficiently (>70%). No MAGE-A4$_{GVY}$-MHC-multimer-staining was observed with the control TCR.
Results:
These results show that TCRs isolated from MAGE-A4-reactive T-cell clones can be transgenically expressed in T cells of a healthy donor (FIG. 6).

Example 8

T Cells Expressing MAGE-A4 Fully Human TCRs Recognize MAGE-A4$_{GVY}$-Peptide

Figure 7:
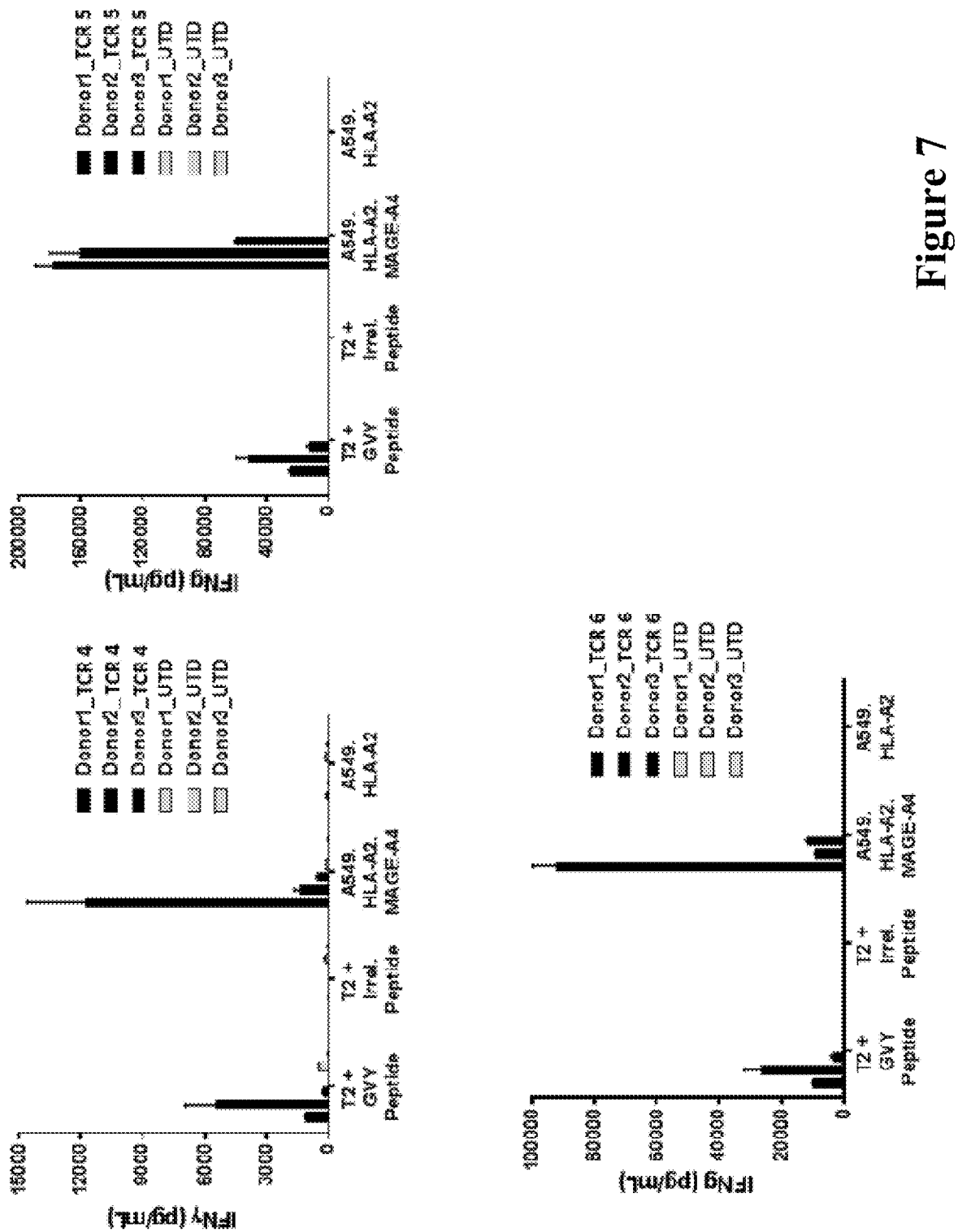
FIG. 7 shows that MAGE-A4 fully human TCR-transgenic T cells recognize MAGE-A4$_{GVY}$-peptide presented on HLA-A2. Transgenic T cells were co-cultured with T2 cells externally loaded with MAGE-A4$_{GVY}$-peptide or A549/HLA-A2 cells that had been transduced with the MAGE-A4 gene. As negative controls, T2 cells loaded with a control peptide and untransduced A549/HLA-A2 cells were used, respectively. Recognition of target cells was analyzed by measuring the IFN-γ concentration in co-culture supernatants by a Luminex assay.

MAGE-A4 specificity of TCR-transgenic T cells was confirmed using antigen dependent cytokine expression. T cells transduced with lentiviral vectors encoding the fully human MAGE-A4 TCRs described in Example 6 were co-cultured at an effector to target cell ratio of 2:1 with T2 cells (HLA-A*02pos) pulsed with 10 ng/mL of MAGE-A4$_{GVY}$-peptide or an irrelevant control peptide and with untransduced A549/HLA-A2 cells or A549/HLA-A2 transduced with the MAGE-A4 gene. After 20-24 hrs., IFN-γ concentrations in co-culture supernatants were analyzed using a Luminex assay.
Results:
MAGE-A4-TCR-transgenic T cells recognized MAGE-A4$_{GVY}$-loaded T2 and MAGE-A4-transduced A549 cells but did not recognize the control target cells. These results show that healthy human donor T cells expressing fully human MAGE-A4 TCRs specifically react with target cells that display the MAGE-A4$_{GVY}$ peptide (FIG. 7).

Example 9

T Cells Expressing MAGE-A4 Fully Human TCRs Show High Functional Avidity

Figure 8:
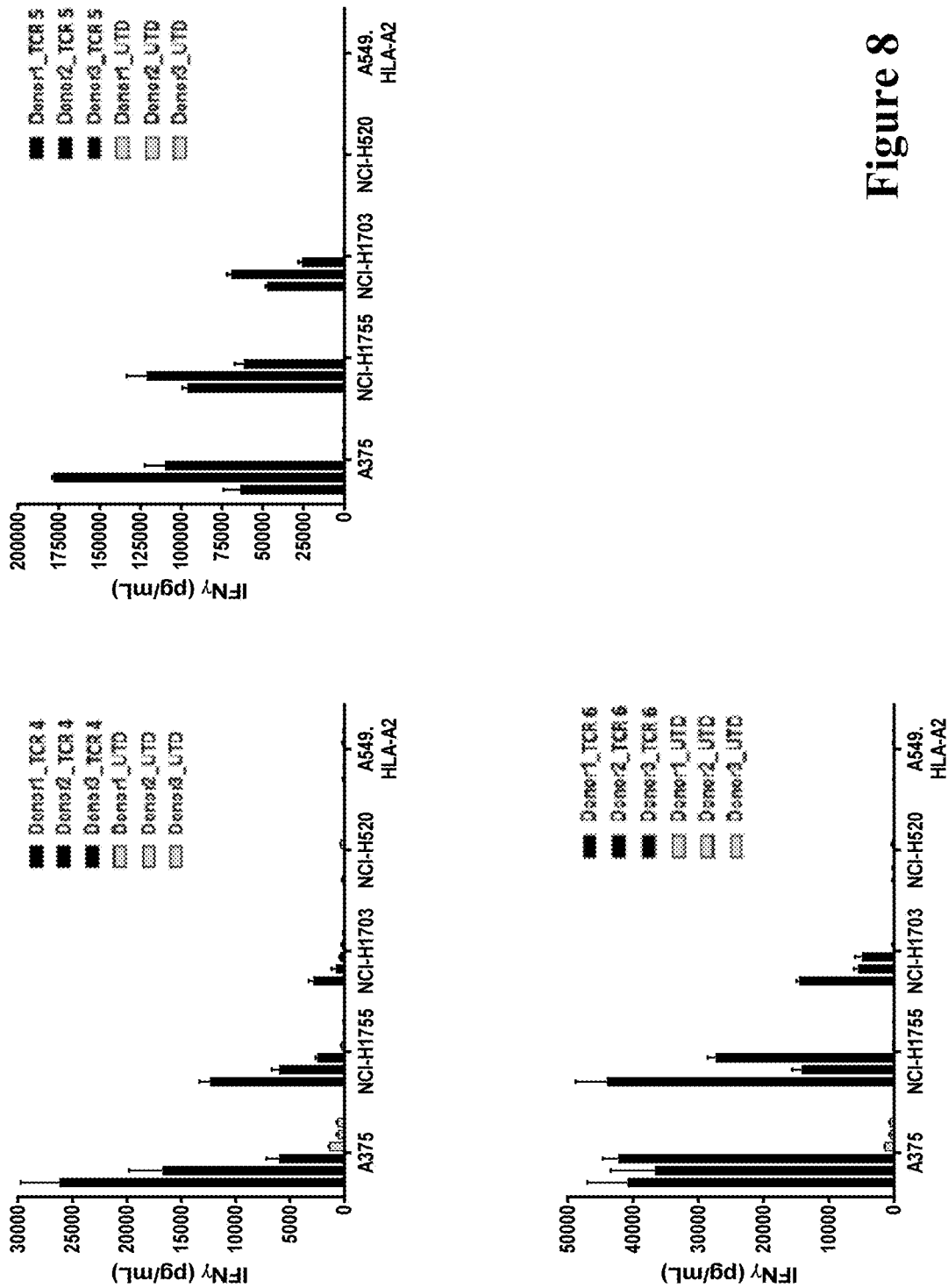
FIG. 8 shows the ability of MAGE-A4 fully human TCR-transgenic T cells to specifically react to MAGE-A4-positive tumor cell lines in an HLA-A2-dependent manner. Transgenic T cells were co-cultured with different MAGE-A4-positive HLA-A2-positive tumor cell lines (A375, NCI-H1703, NCI-H1755), a MAGE-A4-positive HLA-A2-negative tumor cell line (NCI-H520), and a MAGE-A4-negative HLA-A2-positive tumor cell line (A549). To analyze cytokine release, co-culture supernatants were harvested after 24 hrs. and IFN-γ concentrations analyzed by Luminex assay.

Tumor cell lines that display the MAGE-A4$_{GVY}$ peptide were used to analyze differences in the functional avidity of T cells expressing fully human MAGE-A4-TCRs. T cells transduced with lentiviral vectors encoding the fully human MAGE-A4 TCRs described in Example 6 were co-cultured at an effector to target cell ratio of 5:1 with MAGE-A4-positive HLA-A2-positive tumor cell lines (A375, NCI-H1703, NCI-H1755), a MAGE-A4-positive HLA-A2-negative tumor cell line (NCI-H520), and a MAGE-A4-negative HLA-A2-positive tumor cell line (A549). After 20-24 hrs., IFN-γ concentrations in co-culture supernatants were analyzed using a Luminex assay.
Results:
Integrated over multiple donors, MAGE-A4 TCR5 showed the highest functional avidity MAGE-A4-positive HLA-A2-positive tumor cell lines. MAGE-A4 TCR1 and MAGE-A4 TCR-6 showed reduced functional avidity compared to MAGE-A4 TCR-5 (FIG. 8).

Example 10

Figure 9:
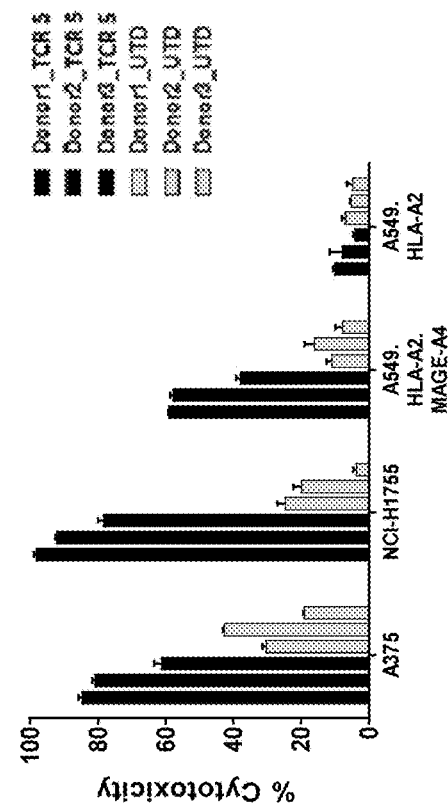
FIG. 9 shows the ability of MAGE-A4 fully human TCR-transgenic T cells to lyse MAGE-A4-positive tumor cell lines in a HLA-A2-dependent manner. Transgenic T cells were co-cultured with different MAGE-A4-positive HLA-A2-positive tumor cell lines (A375, NCI-H1755, A549-HLA-A2-MAGE-A4) and a MAGE-A4-negative HLA-A2-positive tumor cell line (A549-HLA-A2). Cytotoxicity against the tumor cell lines was measured by an impedance assay beginning 6 hours after co-culture initiation.
Figure 9:
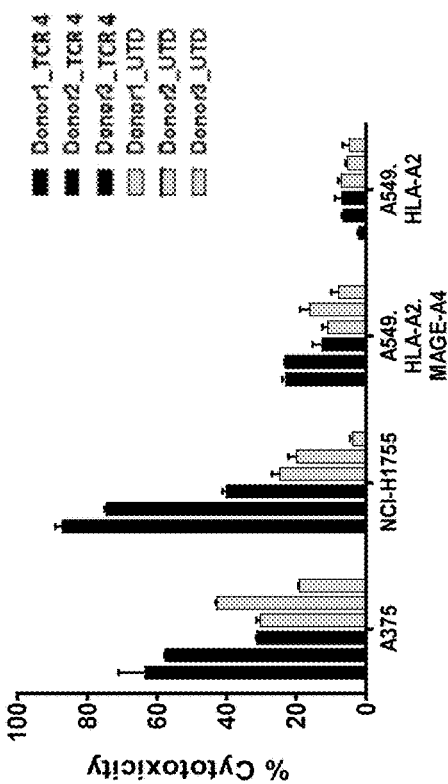
Figure 9:
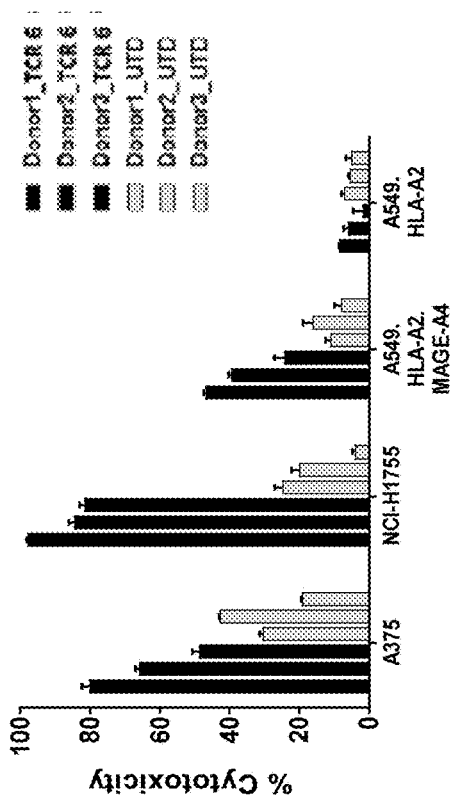

T Cells Expressing MAGE-A4 Fully Human TCRs Lyse MAGE-A4-Positive HLA-A2-Positive Tumor Cell Lines T cells transduced with lentiviral vectors encoding the fully human MAGE-A4 TCRs described in Example 6 were co-cultured at an effector to target cell ratio of 5:1 with MAGE-A4-positive HLA-A2-positive tumor cell lines (A375, NCI-H1703, A549-HLA-A2-MAGE-A4) and a MAGE-A4-negative HLA-A2-positive tumor cell line (A549-HLA-A2). After 6 hrs. of co-culture, cytotoxicity against the tumor cell lines was measured by impedance assay.
Results:
The MAGE-A4-positive HLA-A2 positive tumor cell lines (A375, NCI-H1703, A549-HLA-A2-MAGE-A4) were recognized and lysed by all MAGE-A4-TCR-transgenic T cells. Lysis of the MAGE-A4-negative HLA-A2-positive tumor cell line (A549-HLA-A2) MAGE-A4-TCR-transgenic T cells was not significantly different from the lysis observed using untransduced control T cells (FIG. 9).

Example 11

Figure 10:
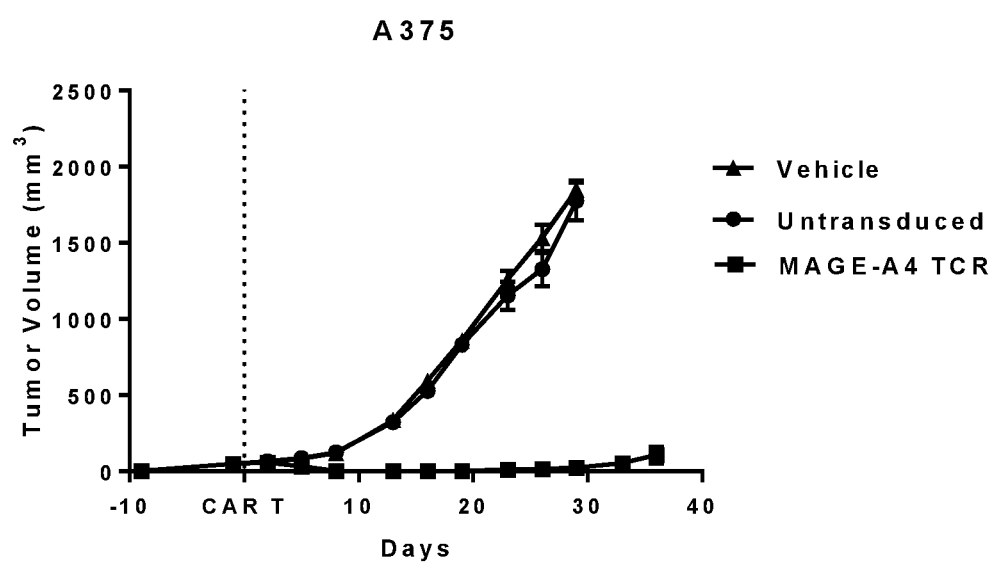
FIG. 10 shows the ability of a MAGE-A4 fully human TCR-transgenic T cells to control MAGE-A4-positive tumors engrafted in NSG mice.

T Cells Expressing MAGE-A4 Fully Human TCRs Control MAGE-A4-Positive Tumors In Vivo 5×10$^6$ MAGE-A4 positive A375 tumor cells were injected in each flank of 10 NSG mice. Ten days after tumor engraftment, 3.5×10$^7$ MAGE-A4-TCR-transgenic T cells, 3.5×10$^7$ control untransduced T cells or vehicle PBS were administered to the mice. After treatment, all mice had their tumor volumes measured twice a week by a caliper.
Results:
Untransduced T cell and vehicle-PBS treated mice failed to control tumor growth and were sacrificed once tumors reached maximum size permitted per protocol. MAGE-A4-TCR transgenic T cell treated mice controlled tumor growth for up to 35 days post T cell infusions (FIG. 10).

Example 12

Enhanced Human MAGE-A4 TCRs

The TCR polynucleotide sequences identified in Example 1 were modified to enhance expression and functional avidity. The TCR α and β chain constant regions were minimally murinized and hydrophobic amino acid substitutions were introduced into the transmembrane domain of TCR α chain constant region. Exemplary polynucleotide sequences for the enhanced MAGE-A4 TCRs are set forth in SEQ ID NOs: 97-99, 103-105, and 109-111. Exemplary polypeptide sequences for the enhanced MAGE-A4 TCRs are set forth in SEQ ID NOs: 100-102, 106-108, and 112-114.

Lentiviral vectors encoding polycistronic TCR constructs were used to express the enhanced MAGE-A4 TCRs (TCR-7, TCR-8, and TCR-9). The polycistronic TCR constructs contain a TCR α or β chain, an optional furin cleavage site, a P2A ribosomal skipping sequence, and the corresponding TCR α or β chain. Lentiviral vectors were produced according to known methods. See e.g., Kutner et al., BMC Biotechnol. 2009; 9:10. doi: 10.1186/1472-6750-9-10; Kutner et al. Nat. Protoc. 2009; 4(4):495-505. doi: 10.1038/nprot.2009.22.

The polycistronic polynucleotide (SEQ ID NO: 99) encoding the MAGE-A4 TCR-7 polyprotein (SEQ ID NO: 102) contains a β chain encoded by SEQ ID NO: 98, a polynucleotide encoding a ribosomal skip sequence, and an α chain encoded by SEQ ID NO: 97.

The polycistronic polynucleotide (SEQ ID NO: 105) encoding the MAGE-A4 TCR-8 polyprotein (SEQ ID NO: 108) contains a β chain encoded by SEQ ID NO: 104, a polynucleotide encoding a furin cleavage site, a polynucleotide encoding a ribosomal skip sequence, and an α chain encoded by SEQ ID NO: 103.

The polycistronic polynucleotide (SEQ ID NO: 111) encoding the MAGE-A4 TCR-9 polyprotein (SEQ ID NO: 114) contains a β chain encoded by SEQ ID NO: 110, a polynucleotide encoding a furin cleavage site, a polynucleotide encoding a ribosomal skip sequence, and an α chain encoded by SEQ ID NO: 109.

Example 13

T Cells Expressing MAGE-A4 Fully Human TCRs or Enhanced MAGE-A4 TCRs can be Efficiently Expressed on Human T Cells Peripheral blood mononuclear cells (PBMCs) were isolated from three independent healthy donors, activated, and transduced with lentiviral vectors encoding a fully human MAGE-A4 TCR (TCR-5) or an enhanced MAGE-A4 TCR (TCR-8) or not transduced as a negative control. The cells were cultured for expansion in vitro and analyzed for vector integration by measuring vector copy number (VCN) and for expression by using flow cytometry against cells stained with a MAGE-A4$_{GVY}$-MHC-multimer (MAGE-A4$^{230-239}$, GVYDGREHTV; immuneAware) and antibodies against CD3.

Figure 11:
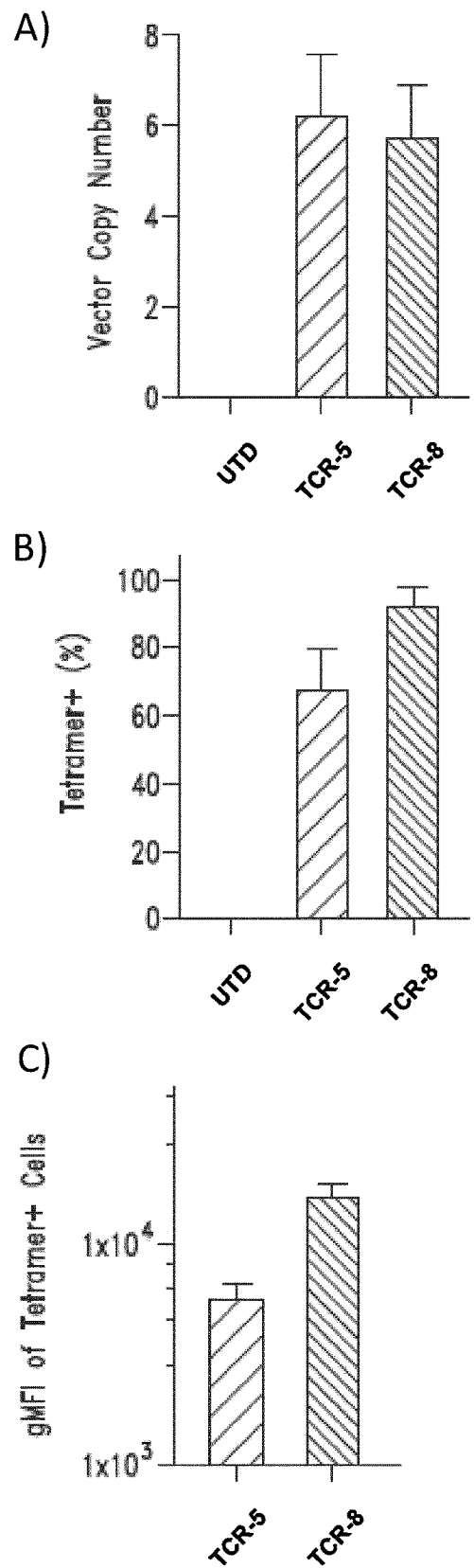
FIGS. 11A-C show the vector copy number (VCN) and expression of MAGE-A4 TCRs. Peripheral blood mononuclear cells (PBMCs) were transduced with lentiviral vectors encoding a fully human MAGE-A4 TCR (TCR-5) or enhanced variant (TCR-8). A) VCN measurements in TCR-5 and TCR-8 T cells were comparable. B) TCR expression on the T cell surface was evaluated using GVY-specific tetramer detection by flow cytometry and shown as percentage of total CD3+ T cells. TCR-8 expression is increased compared to TCR-5 expression. C) The density of TCR molecules on the T cell surface was evaluated using GVY-specific tetramer detection by flow cytometry and shown as geometric Mean Fluorescence Intensity (gMFI) of total Tetramer+ TCR T cells. Expression density of TCR-8 is increased compared to TCR-5 expression density.

Results:
The VCNs for TCR-5 and TCR-8 were comparable, whereas TCR surface expression and density was higher in cells transduced with TCR-8 and with TCR-5. FIG. 11A-C.

Example 14

T Cells Expressing MAGE-A4 Fully Human TCRs or Enhanced MAGE-A4 TCRs Specifically Recognize and Kill MAGE-A4+ Cell Lines In Vitro Peripheral blood mononuclear cells (PBMCs) were isolated from three independent healthy donors, activated, and transduced with lentiviral vectors encoding a fully human MAGE-A4 TCR (TCR-5) or an enhanced MAGE-A4 TCR (TCR-8) or untransduced (UTD) as a negative control. The TCR expressing T cells were evaluated for specific reactivity against MAGEA4 positive (+) and negative (−) tumor cell lines: A549.A2 (A2+, MAGE-A4(−)); NCI-H2023 (A2+, MAGE-A4(+)); A375 (A2+, MAGE-A4(+)); A549.A2.MAGEA4 (A2+, MAGE-A4(+)); and U2OS (A2+, MAGE-A4(low)).

Figure 12:
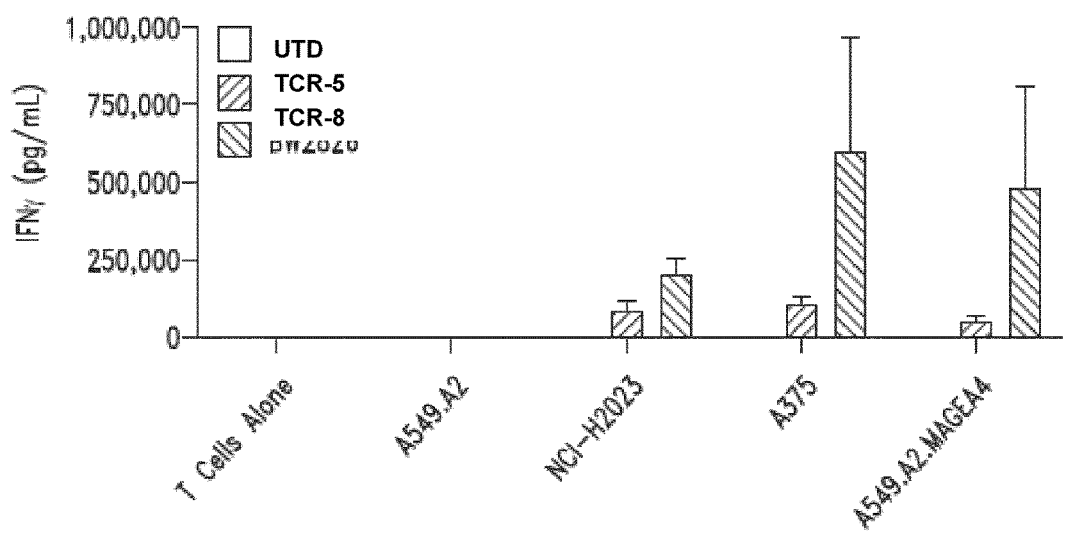
FIGS. 12A-B show that T cells expressing a fully human MAGE-A4 TCR (TCR-5) or enhanced variant (TCR-8) specifically kill MAGE-A4 expressing target cells in vitro. A) TCR-5, TCR-8, or untransduced (UTD) T cells were co-cultured with A549.A2 cells (A2+, MAGE-A4(−)), NCI-H2023 cells (A2+, MAGE-A4(+)), A375 cells (A2+, MAGE-A4(+)), or A549.A2.MAGEA4 cells (A2+, MAGE-A4(+)) at 1:1 E:T ratio. IFNγ release was evaluated as a biomarker for T-cell activity after 24 hrs. TCR-5 and TCR-8 T cells secreted INFγ when co-cultured targets cells expressing MAGE-A4 but not in the presence of MAGE-A4 negative. B) TCR-5, TCR-8, or untransduced (UTD) T cells were co-cultured with A375 cells (A2+, MAGE-A4(+)), A549.A2.MAGEA4 cells (A2+, MAGE-A4(+)), or U2OS cells (A2+, MAGE-A4(low)), at 10:1, 5:1 and 2.5:1 E:T ratios. Cytotoxicity was measured as normalized percentage over tumor cell alone after 6 hours by means of impedance. TCR-5 and TCR-8 T cells mediated comparable cytotoxicity against the three MAGE-A4 expressing cell lines.
Figure 12:
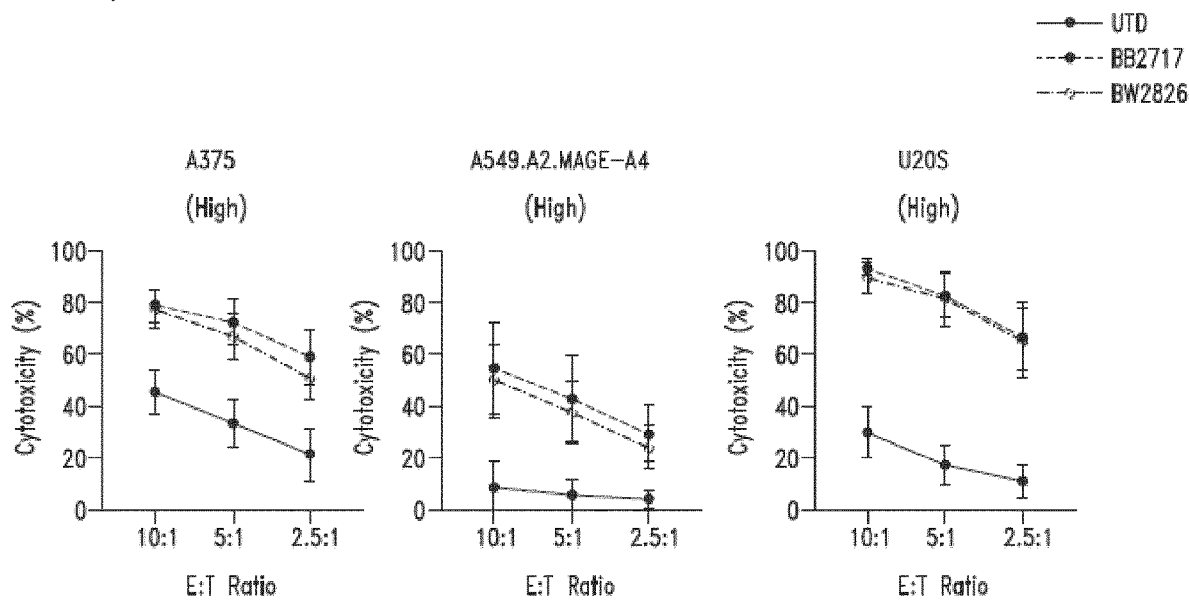
Figure 13:
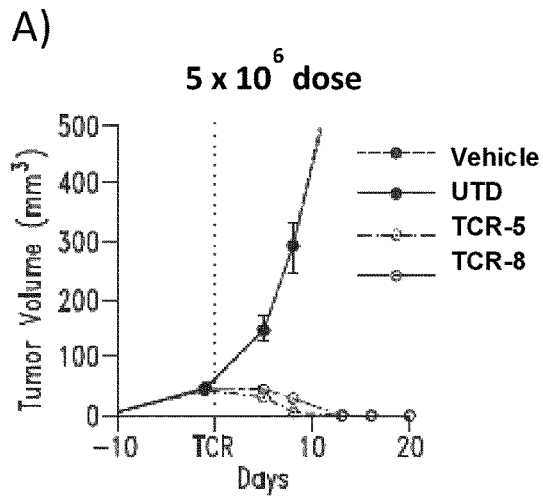
FIGS. 13A-C show that T cells expressing a fully human MAGE-A4 TCR (TCR-5) or enhanced variant (TCR-8) mediate regression in mice with MAGE-A4 expressing tumors. 5 NSG mice (each condition) were injected subcutaneously with MAGEA4(+) A375 tumor cells, and treated with Vehicle, UTD T cells, or T cells expressing a fully human MAGE-A4 TCR (TCR-5) or enhanced variant (TCR-8). Tumor growth was measured twice a week and TCR T cells anti-tumor activity was evaluated in comparison to mice receiving UTD and Vehicle controls. A and B) mice with 50 mm³ A375 tumors received 5×10⁶ (left flank, A) or 1.5×10⁶ (right flank, B) UTD T cells, TCR-5 T cells, or TCR-8 T cells. Both TCR-5 and TCR-8 T cells controlled tumors at a dose of 5×10⁶ T cells, but TCR-8 T cells showed increased control of tumors at the lower dose of 1.5×10⁶ T cells. C) mice with 100 mm³ A375 tumors received 10×10⁶ UTD T cells, TCR-5 T cells, or TCR-8 T cells. TCR-8 T cells mediated increased tumor regression compared to TCR-5 T cells or UTD T cells.
Figure 13:
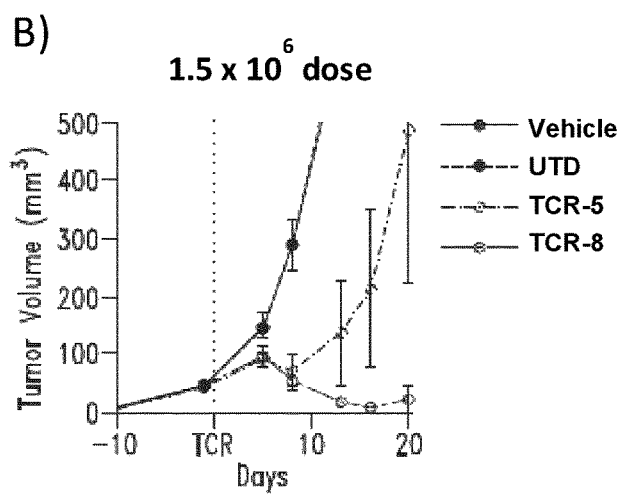
Figure 13:
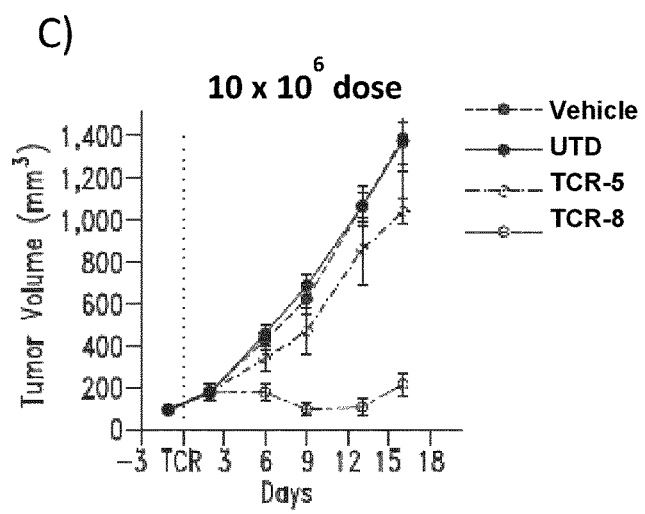

Results:
TCR-5 and TCR-8 T cells released IFNγ when co-cultured with HLA-A2+/MAGEA4(+) tumor cell lines but not when co-cultured with HLA-A2+/MAGEA4(−) cells or when cultured in the absence of target cell. UTD T cells did not release IFNγ in any culture conditions. FIG. 12A.

TCR-5 and TCR-8 T cells effectively killed HLA-A2+/MAGEA4(+) tumor cell lines at E:T ratios of 10:1, 5:1, and 2.5:1. UTD T cells did not kill HLA-A2+/MAGEA4(+) tumor cell lines at any E:T ratio. FIG. 12B.

Example 15

T Cells Expressing MAGE-A4 Fully Human TCRs or Enhanced MAGE-A4 TCRs Mediate Regression of MAGE-A4 Expressing Tumors In Vivo MAGE-A4 positive A375 tumor cells were injected in each flank of 5 NSG mice. Mice with 50 mm³ A375 tumors were administered PBS (Vehicle), untransduced T cells (UTD), 5×10⁶ TCR-5 or TCR-8 T cells (left flank), or 1.5×10⁶ TCR-5 or TCR-8 T cells (right flank). Mice with 100 mm³ A375 tumors were administered PBS (Vehicle), untransduced (UTD) T cells, or 10×10⁶ TCR-5 or TCR-8 T cells. Tumor growth was measured twice a week and TCR T cells anti-tumor activity was evaluated in comparison to mice receiving UTD and Vehicle controls.

Results:
TCR-5 and TCR-8 T cells mediated comparable tumor regression of 50 mm³ A375 tumors at a dose of 5×10⁶ TCR+ T cells. TCR-8 T cells mediated increased tumor regression compared to TCR-5 T cells of 50 mm³ A375 tumors at a dose of 1.5×10⁶ TCR+ T cells and of 100 mm³ A375 tumors at a dose of 10×10⁶ TCR+ T cells. Vehicle and UTD T cells did not mediate regression of A375 tumors in any condition.

The invention is further characterized by the following items:

Item 1: An isolated T cell receptor (TCR) specific for MAGE-A4.

Item 2: An isolated T cell receptor (TCR) specific for MAGE-A4, wherein the TCR comprises:
 a) a variable TCR α region comprising a CDR1 having the amino acid sequence of SEQ ID NO: 2, a CDR2 having the amino acid sequence of SEQ ID NO: 3 and a CDR3 having the amino acid sequence of SEQ ID NO: 4, a variable TCR β region comprising a CDR1 having the amino acid sequence of SEQ ID NO: 5, a CDR2 having the amino acid sequence of SEQ ID NO: 6 and a CDR3 having the amino acid sequence of SEQ ID NO: 7; or
b) a variable TCR α region comprising a CDR1 having the amino acid sequence of SEQ ID NO: 12, a CDR2 having the amino acid sequence of SEQ ID NO: 13 and a CDR3 having the amino acid sequence of SEQ ID NO: 14,
a variable TCR β region comprising a CDR1 having the amino acid sequence of SEQ ID NO: 15, a CDR2 having the amino acid sequence of SEQ ID NO: 16 and a CDR3 having the amino acid sequence of SEQ ID NO: 17; or
c) a variable TCR α region comprising a CDR1 having the amino acid sequence of SEQ ID NO: 22, a CDR2 having the amino acid sequence of SEQ ID NO: 23 and a CDR3 having the amino acid sequence of SEQ ID NO: 24,
a variable TCR β region comprising a CDR1 having the amino acid sequence of SEQ ID NO: 25, a CDR 2 having the amino acid sequence of SEQ ID NO: 26 and a CDR 3 having the amino acid sequence of SEQ ID NO: 27.

Item 3: The isolated TCR according to any of the preceding items, wherein the TCR specifically recognizes the amino acid sequence SEQ ID NO: 1 or a fragment thereof.

Item 4: The isolated TCR according to any of the preceding items, wherein the TCR specifically recognizes the HLA-A2 bound form of the amino acid sequence of SEQ ID NO: 1.

Item 5: The isolated TCR according to any of the preceding items, wherein the TCR specifically recognizes the amino acid sequence of SEQ ID NO: 1, which is presented by the HLA-A*02:01 encoded molecule.

Item 6: The isolated TCR according to any of the preceding items, wherein the TCR comprises a TCR α chain comprising a complementarity-determining region 3 (CDR3) having the sequence selected from the group consisting of SEQ ID NO: 4, SEQ ID NO: 14 and SEQ ID NO: 24.

Item 7: The isolated TCR according to any one of the preceding items, wherein the TCR comprises a TCR β chain comprising a CDR3 having the amino acid sequence selected from the group consisting of SEQ ID NO: 7, SEQ ID NO: 17 and SEQ ID NO: 27.

Item 8: The isolated TCR according to any one of the preceding items, wherein the TCR comprises
a) a variable TCR α region having an amino acid sequence which is at least 80% identical to SEQ ID NO: 8 and a variable TCR β region having an amino acid sequence which is at least 80% identical to SEQ ID NO: 9; or
b) a variable TCR α region having an amino acid sequence which is at least 80% identical to SEQ ID NO: 18 and a variable TCR β region having an amino acid sequence which is at least 80% identical to SEQ ID NO: 19; or
c) a variable TCR α region having an amino acid sequence which is at least 80% identical to SEQ ID NO: 28 and a variable TCR β region having an amino acid sequence which is at least 80% identical to SEQ ID NO: 29

Item 9: The isolated TCR according to any one of the preceding items, wherein the TCR comprises
a) a variable TCR α region having the amino acid sequence of SEQ ID NO: 8 and a variable TCR β region having the amino acid sequence of SEQ ID NO: 9; or
b) a variable TCR α region having the amino acid sequence of SEQ ID NO: 18 and a variable TCR β region having the amino acid sequence of SEQ ID NO: 19; or
c) a variable TCR α region having the amino acid sequence of SEQ ID NO: 28 and a variable TCR β region having the amino acid sequence of SEQ ID NO: 29.

Item 10: The isolated TCR according to any one of the preceding items, wherein the TCR comprises
a) a TCR α chain having an amino acid sequence which is at least 80% identical to SEQ ID NO: 10 and a TCR β chain having an amino acid sequence which is at least 80% identical to SEQ ID NO: 11; or
b) a TCR α chain having an amino acid sequence which is at least 80% identical to SEQ ID NO: 20 and a TCR β chain having an amino acid sequence which is at least 80% identical to SEQ ID NO: 21; or
c) a TCR α chain having an amino acid sequence which is at least 80% identical to SEQ ID NO: 30 and a TCR β chain having an amino acid sequence which is at least 80% identical to SEQ ID NO: 31

Item 11: The isolated TCR according to any one of the preceding items, wherein the TCR comprises
a) a TCR α chain having the amino acid sequence of SEQ ID NO: 10 and a TCR β chain having the amino acid sequence of SEQ ID NO: 11; or
b) a TCR α chain having the amino acid sequence of SEQ ID NO: 20 and a TCR β chain having the amino acid sequence of SEQ ID NO: 21; or
c) a TCR α chain having the amino acid sequence of SEQ ID NO: 30 and a TCR β chain having the amino acid sequence of SEQ ID NO: 31.

Item 12: The isolated TCR according to any one of the preceding items, wherein the TCR comprises a TCR α chain and a TCR β chain, wherein
a)—the variable TCR α region has an amino acid sequence which is at least 80% identical to SEQ ID NO: 8 and comprises a CDR3 encoded by the amino acid sequence set out in SEQ ID NO: 4
the variable TCR β region has an amino acid sequence which is at least 80% identical to SEQ ID NO: 9 and comprises a CDR3 encoded by the amino acid sequence set out in SEQ ID NO: 7; or
b)—the variable TCR α region has an amino acid sequence which is at least 80% identical to SEQ ID NO: 18 and comprises a CDR3 encoded by the amino acid sequence set out in SEQ ID NO: 14; or
the variable TCR β region has an amino acid sequence which is at least 80% identical to SEQ ID NO: 19 and comprises a CDR3 encoded by the amino acid sequence set out in SEQ ID NO: 17; or
c)—the variable TCR α region has an amino acid sequence which is at least 80% identical to SEQ ID NO: 28 and comprises a CDR3 encoded by the amino acid sequence set out in SEQ ID NO: 24; or
the variable TCR β region has an amino acid sequence which is at least 80% identical to SEQ ID NO: 29 and comprises a CDR3 encoded by the amino acid sequence set out in SEQ ID NO: 27.

Item 13: The isolated TCR of any one of items 1 to 5, wherein the TCR comprises:
- a) a TCR α chain having the amino acid sequence of SEQ ID NO: 10 and a TCR β chain having the amino acid sequence of SEQ ID NO: 11;
- b) a TCR α chain having the amino acid sequence of SEQ ID NO: 20 and a TCR β chain having the amino acid sequence of SEQ ID NO: 21; or
- c) a TCR α chain having the amino acid sequence of SEQ ID NO: 30 and a TCR β chain having the amino acid sequence of SEQ ID NO: 31.

Item 14: The isolated TCR of any one of items 1 to 5, wherein the TCR comprises:
- a) a TCR α chain having the amino acid sequence of SEQ ID NO: 87 and a TCR β chain having the amino acid sequence of SEQ ID NO: 88;
- b) a TCR α chain having the amino acid sequence of SEQ ID NO: 89 and a TCR β chain having the amino acid sequence of SEQ ID NO: 90; or
- c) a TCR α chain having the amino acid sequence of SEQ ID NO: 91 and a TCR β chain having the amino acid sequence of SEQ ID NO: 92.

Item 15: The isolated TCR of any one of items 1 to 5, wherein the TCR comprises:
- a) a TCR α chain having the amino acid sequence of SEQ ID NO: 102 and a TCR β chain having the amino acid sequence of SEQ ID NO: 103;
- b) a TCR α chain having the amino acid sequence of SEQ ID NO: 108 and a TCR β chain having the amino acid sequence of SEQ ID NO: 109; or
- c) a TCR α chain having the amino acid sequence of SEQ ID NO: 114 and a TCR β chain having the amino acid sequence of SEQ ID NO: 115.

Item 16: The isolated TCR according to any one of the preceding items, wherein the TCR is purified.

Item 17: The isolated TCR according to any one of the preceding items, wherein its amino acid sequence comprises one or more phenotypically silent substitutions.

Item 18: The isolated TCR according to any one of the preceding items, wherein its amino acid sequence is modified to comprise a detectable label, a therapeutic agent or pharmacokinetic modifying moiety.

Item 19: The isolated TCR according to item 18, wherein the therapeutic agent is selected from the group consisting of an immune effector molecule, a cytotoxic agent and a radionuclide.

Item 20: The isolated TCR according to item 19, wherein the immune effector molecule is a cytokine.

Item 21: The isolated TCR according to any one of the preceding items, wherein the TCR is soluble or membrane bound.

Item 22: The isolated TCR according to item 18, wherein the pharmacokinetic modifying moiety is at least one polyethylene glycol repeating unit, at least one glycol group, at least one sialyl group or a combination thereof.

Item 23: The isolated TCR according to any one of the preceding items, wherein the TCR is of the single chain type, wherein the TCR α chain and the TCR β chain are linked by a linker sequence.

Item 24: The isolated TCR according to any one of items 1 to 23, wherein the TCR α chain or the TCR β chain is modified to comprise an epitope tag.

Item 25: The isolated polypeptide comprising a functional portion of the TCR of any one of items 1 to 24, wherein the functional portion comprises at least one of the amino acid sequences of SEQ ID NOs: 4, 7, 14, 17, 24 and 27.

Item 26: The isolated polypeptide according to item 25, wherein the functional portion comprises the TCR α variable chain and/or the TCR β variable chain.

Item 27: A fusion protein comprising a TCR α chain and a TCR β chain, wherein the fusion protein comprises the amino acid sequence set forth in any one of SEQ ID NOs: 94, 96, 98, 104, 110, and 116.

Item 28: A multivalent TCR complex comprising a least two TCRs as embodied in any one of items 1 to 24.

Item 29: The multivalent TCR complex of item 28, wherein at least one of said TCRs is associated with a therapeutic agent.

Item 30: The isolated TCR according to any one of items 1 to 24, polypeptide according to item 25 or 26, fusion protein according to item 27, multivalent TCR complex according to item 28 or 29, wherein IFN-γ secretion is induced by binding to the amino acid sequence of SEQ ID NO: 1, which is presented by the HLA-A*02:01 encoded molecule.

Item 31: A nucleic acid encoding a TCR according to any one of items 1 to 24, encoding the polypeptide according to item 25 or 26, or encoding the fusion protein according to item 27.

Item 32: The nucleic acid according to item 31, wherein the nucleic acid sequence encoding the TCRα chain is set forth in any one of SEQ ID NOs: 69, 77, 85, 99, 105, and 111.

Item 33: The nucleic acid according to item 31 or item 32, wherein the nucleic acid sequence encoding the TCRβ chain is set forth in any one of SEQ ID NOs: 70, 78, 86, 100, 106, and 112.

Item 34: The nucleic acid according to item 31, wherein the TCR comprises an α chain encoded by SEQ ID NO: 69 and a β chain encoded by SEQ ID NO: 70; an α chain encoded by SEQ ID NO: 77 and a β chain encoded by SEQ ID NO: 78; an α chain encoded by SEQ ID NO: 85 and a β chain encoded by SEQ ID NO: 86; an α chain encoded by SEQ ID NO: 99 and a β chain encoded by SEQ ID NO: 100; an α chain encoded by SEQ ID NO: 105 and a β chain encoded by SEQ ID NO: 106; or an α chain encoded by SEQ ID NO: 111 and a β chain encoded by SEQ ID NO: 112.

Item 35: The nucleic acid according to item 31, wherein the fusion protein is encoded by the nucleic acid sequence set forth in any one of SEQ ID NOs: 93, 95, 97, 101, 107, and 113.

Item 36: A vector comprising the nucleic acid of any one of items 31 to 35.

Item 37: A vector comprising a nucleic acid encoding (a) the polypeptide sequences set forth in SEQ ID NO: 87 and SEQ ID NO: 88; (b) the polypeptide sequences set forth in SEQ ID NO: 89 and SEQ ID NO: 90; (c) the polypeptide sequences set forth in SEQ ID NO: 91 and SEQ ID NO: 92; (d) the polypeptide sequences set forth in SEQ ID NO: 102 and SEQ ID NO: 103; (e) the polypeptide sequences set forth in SEQ ID NO: 108 and SEQ ID NO: 109; or (f) the polypeptide sequences set forth in SEQ ID NO: 114 and SEQ ID NO: 115.

Item 38: The vector according to item 36 or item 37, wherein the vector is an expression vector.

Item 39: The vector according to any one of items 36 to 38, wherein the vector is a retroviral vector.

Item 40: The according to any one of items 36 to 39, wherein the vector is a lentiviral vector.

Item 41: A cell expressing the TCR according to any one of items 1 to 24.

Item 42: A cell comprising the vector according to any one of items 36 to 40.

Item 43: The cell according to item 41 or item 3942 wherein the cell is isolated or non-naturally occurring.

Item 44: A cell comprising the nucleic acid according to any one of items 31 to 35 or the vector according to any one of items 36 to 40.

Item 45: The cell according to items 41 to 44, wherein the cell comprises:
  a) an expression vector which comprises at least one nucleic acid as embodied in any one of items 28 to 32.
  b) a first expression vector which comprises a nucleic acid encoding the alpha chain of the TCR as embodied in any one of the items 1 to 21, and a second expression vector which comprises a nucleic acid encoding the beta chain of a TCR as embodied in any one of the items 1 to 21.

Item 46: The cell according to any one of items 41 to 45, wherein the cell is a peripheral blood lymphocyte (PBL) or a peripheral blood mononuclear cell (PBMC).

Item 49: The cell according to any one of items 41 to 48, wherein the cell is a T cell.

Item 50: The cell according to any one of items 41 to 48, wherein the cell is a T cell.

Item 51: An antibody or antigen binding fragment thereof specifically binding to a portion of the TCR according to any one of items 1 to 24 that mediates specificity for MAGE-A4.

Item 52: The antibody according to item 51, wherein the portion of the TCR that mediates the MAGE-A4 specificity comprises the
  a) CDR3 of the alpha chain of SEQ ID NO: 4 and/or the CDR3 of the beta chain of SEQ ID NO: 7 or;
  b) CDR3 of the alpha chain of SEQ ID NO: 14 and/or the CDR3 of the beta chain of SEQ ID NO: 17 or;
  c) CDR3 of the alpha chain of SEQ ID NO: 24 and/or the CDR3 of the beta chain of SEQ ID NO: 27.

Item 53: A composition comprising the TCR according to any one of items 1 to 24, the polypeptide according to item 25 or 26, the fusion protein according to item 27, the multivalent TCR complex according to item 28 or 29, the nucleic acid according to any one of items 31 to 35, the vector according to any one of items 36 to 40, the cell according to any one of items 41 to 50, or the antibody according to item 51 or 52.

Item 54: A pharmaceutical composition comprising a pharmaceutically acceptable carrier and the TCR according to any one of items 1 to 24, the polypeptide according to item 25 or 26, the fusion protein according to item 27, the multivalent TCR complex according to item 28 or 29, the nucleic acid according to any one of items 31 to 35, the vector according to any one of items 36 to 40, the cell according to any one of items 41 to 50, or the antibody according to item 51 or 52.

Item 55: A pharmaceutical composition comprising at least one pharmaceutically acceptable carrier and the cell according to any one of items 41 to 50.

Item 56: The TCR according to any one of items 1 to 24, the polypeptide according to item 25 or 26, the fusion protein according to item 27, the multivalent TCR complex according to item 28 or 29, the nucleic acid according to any one of items 31 to 35, the vector according to any one of items 36 to 40, the cell according to any one of items 41 to 50, the antibody according to item 51 or 52, the composition of claim 53, or the pharmaceutical composition of claim 54 or claim 55 for use as a medicament.

Item 57: The TCR according to any one of items 1 to 24, the polypeptide according to item 25 or 26, the fusion protein according to item 27, the multivalent TCR complex according to item 28 or 29, the nucleic acid according to any one of items 31 to 35, the vector according to any one of items 36 to 40, the cell according to any one of items 41 to 50, the antibody according to item 51 or 52, the composition of claim 53, or the pharmaceutical composition of claim 54 or claim 55 for use in the treatment of cancer.

Item 58: The TCR, the polypeptide, the fusion protein, the multivalent TCR complex, the nucleic acid, the cell, the antibody, the composition, or the pharmaceutical composition according to item 57, wherein the cancer is a hematological cancer or a solid tumor.

Item 59: The TCR, the polypeptide, the fusion protein, the multivalent TCR complex, the nucleic acid, the cell, the antibody, the composition, or the pharmaceutical composition according to item 57 or 58, wherein the cancer is selected from the group consisting of sarcoma, prostate cancer, uterine cancer, thyroid cancer, testicular cancer, renal cancer, pancreatic cancer, ovarian cancer, esophageal cancer, non-small-cell lung cancer, non-Hodgkin's lymphoma, multiple myeloma, melanoma, hepatocellular carcinoma, head and neck cancer, gastric cancer, endometrial cancer, colorectal cancer, cholangiocarcinoma, breast cancer, bladder cancer, myeloid leukemia and acute lymphoblastic leukemia.

Item 60: The TCR, the polypeptide, the fusion protein, the multivalent TCR complex, the nucleic acid, the cell, the antibody, the composition, or the pharmaceutical composition according to item 50 or 51, wherein the cancer is preferably selected from the group consisting of NSCLC, SCLC, breast, ovarian or colorectal cancer, sarcoma or osteosarcoma.

REFERENCES

Allen, L D (Editor): Remington: The Science and Practice of Pharmacy. Volume I and II. Twenty-second edition. Pharmaceutical Press 2012.

Bhan, S, Chuang, A, Negi, S S, Glazer, C A & Califano, J A: MAGEA4 induces growth in normal oral keratinocytes by inhibiting growth arrest and apoptosis. Oncol. Rep. 2012 28, 1498-1502.

Brichard V G, Louahed J, Clay T M: Cancer regression and neurological toxicity cases after anti-MAGE-A3 TCR gene therapy. J Immunother 2013 36:79-81.

Cameron B J, Gerry A B, Dukes J, Harper J V, Kannan V, Bianchi F C, et al.: Identification of a Titin-derived HLA-A1-presented peptide as a cross-reactive target for engineered MAGE A3-directed Tcells. Sci Transl Med 2013 5:197ra103.

Cribbs A P, Kennedy A, Gregory B, Brennan F M: Simplified production and concentration of lentiviral vectors to achieve high transduction in primary human T cells. BMC Biotechnol. 2013; 13:98.

Daudi S, Eng K H, Mhawech-Fauceglia P, Morrison C, Miliotto A, Beck A, Matsuzaki J, Tsuji T, Groman A, Gnjatic S et al.: Expression and immune responses to MAGE antigens predict survival in epithelial ovarian cancer. PLoS One 2014, 9:e104099.

Duffour M T, Chaux P, Lurquin C, Cornelis G, Boon T, van der Bruggen P:
A MAGE-A4 peptide presented by HLA-A2 is recognized by cytolytic T lymphocytes. Eur J Immunol. 1999 October; 29(10):3329-37.

Engels B, Engelhard V H, Sidney J, Sette A, Binder D C, Liu R B, Kranz D M, Meredith S C, Rowley D A, Schreiber H: Relapse or eradication of cancer is predicted by peptide-major histocompatibility complex affinity. Cancer Cell 2013; 23(4):516-526.

Flynn J K and Gorry P R. Stem memory T cells (TSCM)—their role in cancer and HIV immunotherapies. Clin Transl Immunology 2014; 3(7): e20.

Gargett T, Brown M P: The inducible caspase-9 suicide gene system as a "safety switch" to limit on-target, off-tumor toxicities of chimeric antigen receptor T cells. Front Pharmacol. 2014 Oct. 28; 5: 235.

Gattinoni L, Lugli E, Ji Y, Pos Z, Paulos C M, Quigley M F, Almeida J R, Gostick E, Yu Z, Carpenito C, Wang E, Douek D C, Price D A, June C H, Marincola F M, Roederer M, Restifo N P: A human memory T cell subset with stem cell-like properties. Nat Med. 2011; 17(10): 1290-1297.

Giudicelli, V, et al.: IMGT/LIGM-DB, the IMGT® comprehensive database of immunoglobulin and T cell receptor nucleotide sequences, Nucl. Acid Research 2006, 34, D781-D784.

Gure A O, Chua R, Williamson B, Gonen M, Ferrera C A, Gnjatic S, Ritter G, Simpson A J, Chen Y T, Old L J et al.: Cancer-testis genes are coordinately expressed and are markers of poor outcome in non-small cell lung cancer. Clin Cancer Res 2005, 11:8055-8062.

Invitrogen Corporation: Vector NTI Advance™ 10 DNA and protein sequence analysis software. User Manual 2004, 389-662.

Kageyama S, Ikeda H, Miyahara Y, Imai N, Ishihara M, Saito K et al.: Adoptive transfer of MAGE-A4 T-cell receptor gene-transduced lymphocytes in patients with recurrent esophageal cancer. Clin Cancer Res 2015 21:2268-77.

Kieback E, Charo J, Sommermeyer D, Blankenstein T, Uckert W: A safeguard eliminates T cell receptor gene-modified autoreactive T cells after adoptive transfer. PNAS 2008 105 (2) 623-628.

Kim Y D, Park H R, Song M H, Shin D H, Lee C H, Lee M K, Lee S Y: Pattern of cancer/testis antigen expression in lung cancer patients. Int J Mol Med 2012, 29:656-662.

Lefranc and Lefranc: T cell Receptor Factsbook, Academic Press 2001, Elsevier Ltd ISBN 0-12-441352-8.

Li M, Yuan Y H, Han Y, Liu Y X, Yan L, Wang Y, Gu J: Expression profile of cancer-testis genes in 121 human colorectal cancer tissue and adjacent normal tissue. Clin Cancer Res 2005, 11:1809-1814.

Linette G P, Stadtmauer E A, Maus M V, Rapoport A P, Levine B L, Emery L et al.: Cardiovascular toxicity and titin cross-reactivity of affinity-enhanced T cells in myeloma and melanoma. Blood (2013) 122:863-71.

Lugli E, Gattinoni L, Roberto A, Mavilio D, Price D A, Restifo N P, Roederer M: Identification, isolation and in vitro expansion of human and nonhuman primate T stem cell memory cells. Nat Protoc. 2013; 8(1):33-42.

Morgan R A, Chinnasamy N, Abate-Daga D, Gros A, Robbins P F, Zheng Z et al.: Cancer regression and neurological toxicity following anti-MAGE-A3 TCR gene therapy. J Immunother (2013) 36:133-51

Otte M, Zafrakas M, Riethdorf L, Pichlmeier U, Loning T, Janicke F, Pantel K: MAGE-A gene expression pattern in primary breast cancer. Cancer Res 2001, 61:6682-6687.

Riddell S R, Sommermeyer D, Berger C, Liu L S, Balakrishnan A, Salter A, Hudecek M, Maloney D G, Turtle C J: Adoptive therapy with chimeric antigen receptor-modified T cells of defined subset composition. Cancer J. 2014; 20(2):141-144.

Sambrook: Molecular Cloning—4th Edition, Cold Spring Harbor Laboratory Press 2012, ISBN 978-1-936113-42-2.

Sommermeyer D, Uckert W: Minimal amino acid exchange in human TCR constant regions fosters improved function of TCR gene-modified T cells. J Immunol. 2010; 184(11): 6223-6231.

Tajima K, Obata Y, Tamaki H, Yoshida M, Chen Y T, Scanlan M J, Old L J, Kuwano H, Takahashi T, Takahashi T et al.: Expression of cancer/testis (CT) antigens in lung cancer. Lung Cancer 2003, 42:23-33.

Thompson J F, Higgins D G, Gibson T J: CLUSTAL W: improving the sensitivity of progressive multiple sequence alignment through sequence weighting, position-specific gap penalties and weight matrix choice. Nucleic Acids Research 1994, 22: 4673-4680.

Yamada R, Takahashi A, Torigoe T, Morita R, Tamura Y, Tsukahara T, Kanaseki T, Kubo T, Watarai K, Kondo T et al.: Preferential expression of cancer/testis genes in cancer stem-like cells: proposal of a novel sub-category, cancer/testis/stem gene. Tissue Antigens 2013, 81:428-434.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A host cell comprising a T cell receptor (TCR) specific for MAGE-A4, wherein the TCR comprises a TCR α chain comprising a variable TCR α region comprising a CDR1 having the amino acid sequence of SEQ ID NO: 12, a CDR2 having the amino acid sequence of SEQ ID NO: 13 and a CDR3 having the amino acid sequence of SEQ ID NO: 14; and a TCR β chain comprising a variable TCR β region comprising a CDR1 having the amino acid sequence of SEQ ID NO: 15, a CDR2 having the amino acid sequence of SEQ ID NO: 16 and a CDR3 having the amino acid sequence of SEQ ID NO: 17.

2. The host cell of claim 1, wherein the variable TCR α region comprises the amino acid sequence of SEQ ID NO: 18; and the variable TCR β region comprises the amino acid sequence of SEQ ID NO: 19.

3. The host cell of claim 1, wherein the TCR α chain comprises the amino acid sequence of SEQ ID NO: 20; and the TCR β chain comprises the amino acid sequence of SEQ ID NO: 21.

4. The host cell of claim 1, wherein the TCR α chain comprises the amino acid sequence of SEQ ID NO: 89; and the TCR β chain comprises the amino acid sequence of SEQ ID NO: 90.

5. The host cell of claim 1, wherein the TCR α chain comprises the amino acid sequence of SEQ ID NO: 108; and the TCR β chain comprises the amino acid sequence of SEQ ID NO: 109.

6. The host cell of claim 1, wherein the TCR is a fusion protein comprising the TCR α chain and the TCR β chain.

7. The host cell of claim 6, wherein the fusion protein comprises the amino acid sequence of SEQ ID NO: 96.

8. The host cell of claim 6, wherein the fusion protein comprises the amino acid sequence of SEQ ID NO: 110.

9. The host cell of claim 1, wherein the TCR specifically recognizes:
   a) the amino acid sequence SEQ ID NO: 1 or a fragment thereof;
   b) the HLA-A2 bound form of the amino acid sequence of SEQ ID NO: 1; and/or
   c) the amino acid sequence of SEQ ID NO: 1, which is presented by the HLA-A*02:01 encoded molecule.

10. A cell comprising one or more vectors encoding a T cell receptor (TCR) specific for MAGE-A4, wherein the TCR comprises a TCR α chain comprising a variable TCR α region comprising a CDR1 having the amino acid sequence of SEQ ID NO: 12, a CDR2 having the amino acid sequence of SEQ ID NO: 13 and a CDR3 having the amino acid sequence of SEQ ID NO: 14; and a TCR β chain comprising a variable TCR β region comprising a CDR1 having the amino acid sequence of SEQ ID NO: 15, a CDR2 having the amino acid sequence of SEQ ID NO: 16 and a CDR3 having the amino acid sequence of SEQ ID NO: 17.

11. The cell of claim 10, wherein the variable TCR α region comprises the amino acid sequence of SEQ ID NO: 18; and the variable TCR β region comprises the amino acid sequence of SEQ ID NO: 19.

12. The cell of claim 10, wherein the TCR α chain comprises the amino acid sequence of SEQ ID NO: 20; and the TCR β chain comprises the amino acid sequence of SEQ ID NO: 21.

13. The cell of claim 12, wherein the vector comprises a nucleic acid comprising the nucleotide sequences of SEQ ID Nos: 46 and 47.

14. The cell of claim 10, wherein the TCR α chain comprises the amino acid sequence of SEQ ID NO: 89; and the TCR β chain comprises the amino acid sequence of SEQ ID NO: 90.

15. The cell of claim 14, wherein the vector comprises a nucleic acid comprising the nucleotide sequences of SEQ ID Nos: 77 and 78.

16. The cell of claim 10, wherein the TCR α chain comprises the amino acid sequence of SEQ ID NO: 108; and the TCR β chain comprises the amino acid sequence of SEQ ID NO: 109.

17. The cell of claim 16, wherein the vector comprises a nucleic acid comprising the nucleotide sequences of SEQ ID Nos: 105 and 106.

18. The cell of claim 10, wherein the TCR is a fusion protein comprising the TCR α chain and the TCR β chain.

19. The cell of claim 18, wherein the fusion protein comprises the amino acid sequence of SEQ ID NO: 96.

20. The cell of claim 19, wherein the vector comprises a nucleic acid comprising the nucleotide sequence of SEQ ID NO: 95.

21. The cell of claim 18, wherein the fusion protein comprises the amino acid sequence of SEQ ID NO: 110.

22. The cell of claim 21, wherein the vector comprises a nucleic acid comprising the nucleotide sequence of SEQ ID NO: 107.

23. The cell of claim 10, wherein the TCR specifically recognizes:
   a) the amino acid sequence SEQ ID NO: 1 or a fragment thereof;
   b) the HLA-A2 bound form of the amino acid sequence of SEQ ID NO: 1; and/or
   c) the amino acid sequence of SEQ ID NO: 1, which is presented by the HLA-A*02:01 encoded molecule.

24. The cell of claim 10, wherein the vector is a viral vector.

25. The cell of claim 24, wherein the viral vector is a lentiviral vector.

26. The cell of claim 10, wherein the one or more vectors is a single vector.

* * * * *

UNITED STATES PATENT AND TRADEMARK OFFICE
CERTIFICATE OF CORRECTION

PATENT NO. : 12,344,654 B2  
APPLICATION NO. : 17/441861  
DATED : July 1, 2025  
INVENTOR(S) : Christian Ellinger et al.

Page 1 of 2

It is certified that error appears in the above-identified patent and that said Letters Patent is hereby corrected as shown below:

In the Specification

At Column 22, Lines 41-46, please delete

"

| 108 | 102 | TCR-8 α chain complete |
|-----|-----|------------------------|
| 109 | 103 | TCR-8 β chain complete |
| 110 | 104 | TCR-8 fusion protein   |
| 114 | 105 | TCR-9 α chain complete |
| 115 | 106 | TCR-9 β chain complete |
| 116 | 107 | TCR-9 fusion protein   |

" and insert

| 108 | 105 | TCR-8 α chain complete |
|-----|-----|------------------------|
| 109 | 106 | TCR-8 β chain complete |
| 110 | 107 | TCR-8 fusion protein   |
| 114 | 108 | TCR-9 α chain complete |
| 115 | 109 | TCR-9 β chain complete |
| 116 | 110 | TCR-9 fusion protein   |

--

At Column 35, Lines 15-20, please delete "Exemplary polynucleotide sequences for the enhanced MAGE-A4 TCRs are set forth in SEQ ID NOs: 97-99, 103-105, and 109-111. Exemplary polypeptide sequences for the enhanced MAGE-A4 TCRs are set forth in SEQ ID Nos: 100-102, 106-108, and 112-114." and insert -- Exemplary polynucleotide sequences for the enhanced MAGE-A4 TCRs are set forth in SEQ ID NOs: 99-101, 105-107, and 111-113. Exemplary polypeptide sequences for the enhanced MAGE-A4 TCRs are set forth in SEQ ID Nos: 102-104, 108-110, and 114-116. --

At Column 35, Lines 32-35, please delete "The polycistronic polynucleotide (SEQ ID NO: 99) encoding the MAGE-A4 TCR-7 polyprotein (SEQ ID NO: 102) contains a β chain encoded by SEQ ID NO: 98, a polynucleotide encoding a ribosomal skip sequence, and an α chain encoded by SEQ ID NO: 99." and insert -- The polycistronic polynucleotide (SEQ ID NO: 101) encoding the MAGE-A4

Signed and Sealed this  
Second Day of September, 2025

Coke Morgan Stewart  
*Acting Director of the United States Patent and Trademark Office*

TCR-7 polyprotein (SEQ ID NO: 104 ) contains a β chain encoded by SEQ ID NO: 100, a polynucleotide encoding a ribosomal skip sequence, and an α chain encoded by SEQ ID NO: 99. --

At Column 35, Lines 36-41, please delete "The polycistronic polynucleotide (SEQ ID NO: 105) encoding the MAGE-A4 TCR-8 polyprotein (SEQ ID NO: 108) contains a β chain encoded by SEQ ID NO: 104, a polynucleotide encoding a furin cleavage site, a polynucleotide encoding a ribosomal skip sequence, and an α chain encoded by SEQ ID NO: 103." and insert -- The polycistronic polynucleotide (SEQ ID NO: 107) encoding the MAGE-A4 TCR-8 polyprotein (SEQ ID NO: 110) contains a β chain encoded by SEQ ID NO: 106, a polynucleotide encoding a furin cleavage site, a polynucleotide encoding a ribosomal skip sequence, and an α chain encoded by SEQ ID NO: 105. --

At Column 35, Lines 42-47, please delete "The polycistronic polynucleotide (SEQ ID NO: 111) encoding the MAGE-A4 TCR-9 polyprotein (SEQ ID NO: 114) contains a β chain encoded by SEQ ID NO: 110, a polynucleotide encoding a furin cleavage site, a polynucleotide encoding a ribosomal skip sequence, and an α chain encoded by SEQ ID NO: 109." and insert -- The polycistronic polynucleotide (SEQ ID NO: 113) encoding the MAGE-A4 TCR-9 polyprotein (SEQ ID NO: 116) contains a β chain encoded by SEQ ID NO: 112, a polynucleotide encoding a furin cleavage site, a polynucleotide encoding a ribosomal skip sequence, and an α chain encoded by SEQ ID NO: 111. --